US009554909B2

(12) United States Patent
Donner et al.

(10) Patent No.: US 9,554,909 B2
(45) Date of Patent: Jan. 31, 2017

(54) ORTHOPEDIC ANCHORING SYSTEM AND METHODS

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 14/413,318

(22) PCT Filed: Jul. 19, 2013

(86) PCT No.: PCT/US2013/051381
§ 371 (c)(1),
(2) Date: Jan. 7, 2015

(87) PCT Pub. No.: WO2014/015309
PCT Pub. Date: Jan. 23, 2014

(65) Prior Publication Data
US 2015/0150683 A1 Jun. 4, 2015

Related U.S. Application Data

(60) Provisional application No. 61/798,922, filed on Mar. 15, 2013, provisional application No. 61/674,233, filed on Jul. 20, 2012.

(51) Int. Cl.
*A61F 2/30* (2006.01)
*A61B 17/17* (2006.01)
(Continued)

(52) U.S. Cl.
CPC ....... *A61F 2/30749* (2013.01); *A61B 17/1757* (2013.01); *A61B 17/7055* (2013.01);
(Continued)

(58) Field of Classification Search
CPC ............ A61B 17/1757; A61B 17/1742; A61B 17/7055; A61B 17/7076
See application file for complete search history.

(56) References Cited

U.S. PATENT DOCUMENTS 4,488,542 A 12/1984 Helland
4,569,338 A 2/1986 Edwards
(Continued)

FOREIGN PATENT DOCUMENTS

AU 1753200 8/2000
CN 2265765 10/1997
(Continued)

OTHER PUBLICATIONS

Arman et al. The Human Sacrum and Safe Approaches for Screw Placement. *Journal of Clinical Neuroscience* 2008 Elsevier Inc.;16(2009):1046-1049.
(Continued)

*Primary Examiner* — David Bates
*Assistant Examiner* — Olivia C Chang
(74) *Attorney, Agent, or Firm* — Polsinelli PC; Samuel Wade Johnson; Joshua J. Pranckun

(57) ABSTRACT

Systems and methods for performing orthopedic surgical procedures to treat a patient are presented herein. The orthopedic anchoring system may include an implant assembly and a delivery tool to perform the orthopedic surgical procedure. The implant assembly may include an implant outer layer, an implant body situated within the implant outer layer, and a fastener attached to a locking element of the implant body. The delivery tool may include a targeting arm, a fastener guide removably attached at a first end of the targeting arm and an implant guide removably attached to a second end of the targeting arm. The delivery tool may maintain a fixed spatial relationship between a longitudinal (Continued)

axis of the fastener and a longitudinal axis of the implant outer layer and implant body. The orthopedic anchoring system may be used to perform orthopedic surgical procedures related to joint reinforcement or immobilization.

52 Claims, 51 Drawing Sheets

(51) Int. Cl.
  *A61B 17/70* (2006.01)
  *A61F 2/46* (2006.01)
  *A61B 17/15* (2006.01)
  *A61B 17/88* (2006.01)

(52) U.S. Cl.
  CPC ............ *A61B 17/7076* (2013.01); *A61F 2/30* (2013.01); *A61F 2/4637* (2013.01); *A61B 17/15* (2013.01); *A61B 17/8875* (2013.01); *A61F 2002/30332* (2013.01); *A61F 2002/30378* (2013.01); *A61F 2002/30495* (2013.01); *A61F 2002/30617* (2013.01); *A61F 2002/4642* (2013.01)

(56) References Cited

U.S. PATENT DOCUMENTS

| | | |
|---|---|---|
| 4,590,928 A | 5/1986 | Hunt et al. |
| 4,622,959 A | 11/1986 | Marcus |
| 4,714,469 A | 12/1987 | Kenna |
| 4,773,402 A | 9/1988 | Asher et al. |
| 4,794,918 A | 1/1989 | Wolter |
| 4,863,476 A | 9/1989 | Shepperd |
| 4,881,535 A | 11/1989 | Sohngen |
| 4,911,153 A | 3/1990 | Border |
| 4,920,958 A | 5/1990 | Walt et al. |
| 4,950,270 A | 8/1990 | Bowman et al. |
| 5,026,373 A | 6/1991 | Ray et al. |
| 5,052,375 A | 10/1991 | Stark et al. |
| 5,108,397 A | 4/1992 | White |
| 5,112,337 A | 5/1992 | Paulos et al. |
| 5,176,681 A | 1/1993 | Lawes et al. |
| 5,192,327 A | 3/1993 | Brantigan |
| 5,242,444 A | 9/1993 | MacMillan |
| 5,282,861 A | 2/1994 | Kaplan |
| 5,334,192 A | 8/1994 | Behrens |
| 5,334,205 A | 8/1994 | Cain |
| 5,336,225 A | 8/1994 | Zang |
| 5,368,546 A | 11/1994 | Stark et al. |
| 5,368,593 A | 11/1994 | Stark |
| 5,437,674 A | 8/1995 | Worcel et al. |
| 5,443,509 A | 8/1995 | Boucher et al. |
| 5,456,267 A | 10/1995 | Stark |
| 5,480,402 A | 1/1996 | Kim |
| 5,484,389 A | 1/1996 | Stark et al. |
| 5,591,235 A | 1/1997 | Kuslich |
| 5,593,407 A | 1/1997 | Reis |
| 5,607,424 A | 3/1997 | Tropiano |
| 5,609,635 A | 3/1997 | Michelson |
| 5,609,636 A | 3/1997 | Kohrs et al. |
| 5,626,434 A | 5/1997 | Cook |
| 5,658,337 A | 8/1997 | Kohrs et al. |
| 5,669,909 A | 9/1997 | Zdeblick et al. |
| 5,688,284 A | 11/1997 | Chervitz et al. |
| 5,743,914 A | 4/1998 | Skiba |
| 5,772,594 A | 6/1998 | Barrick |
| 5,823,975 A | 10/1998 | Stark et al. |
| 5,888,224 A | 3/1999 | Beckers et al. |
| 5,891,150 A | 4/1999 | Chan |
| 5,919,193 A | 7/1999 | Slavitt |
| 5,928,239 A | 7/1999 | Mirza |
| 5,929,782 A | 7/1999 | Stark et al. |
| 5,993,463 A | 11/1999 | Truwit |
| 6,053,916 A | 4/2000 | Moore |
| 6,056,749 A | 5/2000 | Kuslich |
| 6,063,442 A | 5/2000 | Cohen et al. |
| 6,175,758 B1 | 1/2001 | Kambin |
| 6,184,797 B1 | 2/2001 | Stark et al. |
| 6,236,891 B1 | 5/2001 | Ingle et al. |
| 6,241,771 B1 | 6/2001 | Gresser et al. |
| 6,290,724 B1 | 9/2001 | Marino |
| 6,296,595 B1 | 10/2001 | Stark et al. |
| 6,302,885 B1 | 10/2001 | Essiger |
| 6,322,562 B1 | 11/2001 | Wolter |
| 6,371,123 B1 | 4/2002 | Stark et al. |
| 6,413,278 B1 | 7/2002 | Marchosky |
| 6,432,107 B1 | 8/2002 | Ferree |
| 6,432,140 B1 | 8/2002 | Lin |
| 6,515,593 B1 | 2/2003 | Stark et al. |
| 6,520,990 B1 | 2/2003 | Ray |
| 6,540,707 B1 | 4/2003 | Stark et al. |
| 6,547,795 B2 | 4/2003 | Schneiderman |
| 6,547,823 B2 | 4/2003 | Scarborough et al. |
| 6,558,423 B1 | 5/2003 | Michelson |
| 6,565,605 B2 | 5/2003 | Goble et al. |
| 6,572,622 B1 | 6/2003 | Schäfer et al. |
| 6,579,318 B2 | 6/2003 | Varga et al. |
| 6,607,487 B2 | 8/2003 | Chang et al. |
| 6,635,059 B2 | 10/2003 | Randall et al. |
| 6,641,614 B1 | 11/2003 | Wagner |
| 6,660,224 B2 | 12/2003 | Lefebvre et al. |
| 6,663,669 B1 | 12/2003 | Reiley |
| 6,669,698 B1 | 12/2003 | Tromanhauser et al. |
| 6,682,563 B2 | 1/2004 | Scharf |
| 6,682,567 B1 | 1/2004 | Schroeder |
| 6,716,245 B2 | 4/2004 | Pasquet et al. |
| 6,723,099 B1 | 4/2004 | Goshert |
| 6,743,256 B2 | 6/2004 | Mason |
| 6,746,451 B2 | 6/2004 | Middleton et al. |
| 6,824,564 B2 | 11/2004 | Crozet |
| 6,827,670 B1 | 12/2004 | Stark et al. |
| 6,835,208 B2 | 12/2004 | Marchosky |
| 6,855,166 B2 | 2/2005 | Kohrs |
| 6,855,167 B2 | 2/2005 | Shimp et al. |
| 6,860,902 B2 | 3/2005 | Reiley |
| 6,872,187 B1 | 3/2005 | Stark et al. |
| 6,875,236 B2 | 4/2005 | Reiley |
| 6,902,567 B2 | 6/2005 | Del Medico |
| 6,908,465 B2 | 6/2005 | von Hoffmann et al. |
| 6,945,448 B2 | 9/2005 | Medlin et al. |
| 6,972,019 B2 | 12/2005 | Michelson |
| 6,974,461 B1 | 12/2005 | Wolter |
| 7,011,660 B2 | 3/2006 | Sherman et al. |
| 7,087,056 B2 | 8/2006 | Vaughan |
| 7,087,058 B2 | 8/2006 | Cragg |
| 7,108,828 B2 | 9/2006 | Lefebvre et al. |
| 7,144,399 B2 | 12/2006 | Hayes et al. |
| 7,163,560 B2 | 1/2007 | Mason |
| 7,192,447 B2 | 3/2007 | Rhoda |
| 7,201,775 B2 | 4/2007 | Gorensek et al. |
| 7,208,222 B2 | 4/2007 | Rolfe et al. |
| 7,217,291 B2 | 5/2007 | Zucherman et al. |
| 7,229,448 B2 | 6/2007 | Goble et al. |
| 7,235,101 B2 | 6/2007 | Berry et al. |
| 7,235,105 B2 | 6/2007 | Jackson |
| 7,247,157 B2 | 7/2007 | Prager et al. |
| 7,255,712 B1 | 8/2007 | Steinberg |
| 7,303,563 B2 | 12/2007 | Poyner et al. |
| 7,331,995 B2 | 2/2008 | Eisermann et al. |
| 7,396,360 B2 | 7/2008 | Lieberman |
| 7,410,501 B2 | 8/2008 | Michelson |
| 7,416,537 B1 | 8/2008 | Stark et al. |
| 7,458,991 B2 | 12/2008 | Wang et al. |
| 7,465,317 B2 | 12/2008 | Malberg et al. |
| 7,520,898 B2 | 4/2009 | Re et al. |
| 7,537,616 B1 | 5/2009 | Branch et al. |
| 7,575,600 B2 | 8/2009 | Zucherman et al. |
| 7,621,939 B2 | 11/2009 | Zucherman et al. |
| 7,635,447 B2 | 12/2009 | Hamman et al. |
| 7,637,954 B2 | 12/2009 | Michelson |
| 7,641,697 B2 | 1/2010 | Reiley |
| 7,648,509 B2 | 1/2010 | Stark |
| 7,666,209 B2 | 2/2010 | Zucherman et al. |

(56) References Cited

U.S. PATENT DOCUMENTS

| | | |
|---|---|---|
| 7,670,383 B1 | 3/2010 | Brown et al. |
| 7,704,279 B2 | 4/2010 | Moskowitz et al. |
| 7,713,290 B2 | 5/2010 | Vaughan |
| 7,740,795 B2 | 6/2010 | Wang et al. |
| 7,771,441 B2 | 8/2010 | Cerundolo |
| 7,789,895 B2 | 9/2010 | Heinz |
| 7,794,465 B2 | 9/2010 | Marik et al. |
| 7,799,081 B2 | 9/2010 | McKinley |
| 7,819,869 B2 | 10/2010 | Godara et al. |
| 7,824,404 B2 | 11/2010 | Godara et al. |
| 7,837,732 B2 | 11/2010 | Zucherman et al. |
| 7,837,734 B2 | 11/2010 | Zucherman et al. |
| 7,846,162 B2 | 12/2010 | Nelson et al. |
| 7,850,690 B2 | 12/2010 | Frigg et al. |
| 7,850,719 B2 | 12/2010 | Gournay et al. |
| 7,850,732 B2 | 12/2010 | Heinz |
| 7,909,871 B2 | 3/2011 | Abdou |
| 7,918,891 B1 | 4/2011 | Curran et al. |
| 7,922,765 B2 | 4/2011 | Reiley |
| 7,963,970 B2 | 6/2011 | Marino et al. |
| 7,972,363 B2 | 7/2011 | Moskowitz et al. |
| 7,972,382 B2 | 7/2011 | Foley et al. |
| 7,985,255 B2 | 7/2011 | Bray et al. |
| 8,034,114 B2 | 10/2011 | Reiley |
| 8,034,115 B2 | 10/2011 | Reiley |
| 8,048,164 B2 | 11/2011 | Reiley |
| 8,070,782 B2 | 12/2011 | McKay |
| 8,075,561 B2 | 12/2011 | Wolter |
| 8,083,796 B1 | 12/2011 | Raiszadeh et al. |
| 8,088,163 B1 | 1/2012 | Kleiner |
| 8,128,666 B2 | 3/2012 | Falahee |
| 8,162,981 B2 | 4/2012 | Vestgaarden |
| 8,187,332 B2 | 5/2012 | McLuen |
| 8,202,305 B2 | 6/2012 | Reiley |
| 8,221,428 B2 | 7/2012 | Trieu |
| 8,231,661 B2 | 7/2012 | Carls et al. |
| 8,308,779 B2 | 11/2012 | Reiley |
| 8,308,794 B2 | 11/2012 | Martinson et al. |
| 8,317,862 B2 | 11/2012 | Troger et al. |
| 8,343,189 B2 | 1/2013 | Assell et al. |
| 8,343,219 B2 | 1/2013 | Allain et al. |
| 8,348,950 B2 | 1/2013 | Assell et al. |
| 8,388,667 B2 | 3/2013 | Reiley |
| 8,414,648 B2 | 4/2013 | Reiley |
| 8,425,570 B2 | 4/2013 | Reiley |
| 8,425,603 B2 | 4/2013 | Reichen et al. |
| 8,439,925 B2 | 5/2013 | Marino et al. |
| 8,444,693 B2 | 5/2013 | Reiley |
| 8,454,618 B2 | 6/2013 | Stark |
| 8,470,004 B2 | 6/2013 | Reiley |
| 8,470,037 B2 | 6/2013 | Re et al. |
| 8,480,755 B2 | 7/2013 | Reiley |
| 8,491,572 B2 | 7/2013 | Martinson et al. |
| 8,491,653 B2 | 7/2013 | Zucherman et al. |
| 8,496,712 B2 | 7/2013 | Reiley |
| 8,501,690 B2 | 8/2013 | Stark |
| 8,518,120 B2 | 8/2013 | Glerum |
| 8,551,171 B2 | 10/2013 | Johnson et al. |
| 8,562,651 B2 | 10/2013 | Metcalf et al. |
| 8,579,912 B2 | 11/2013 | Isaza et al. |
| 8,585,744 B2 | 11/2013 | Duggal et al. |
| D697,209 S | 1/2014 | Walthall, Jr. et al. |
| 8,623,062 B2 | 1/2014 | Kondrashov |
| 8,778,026 B2 | 7/2014 | Mauldin |
| 8,808,305 B2 | 8/2014 | Kleiner |
| 8,808,336 B2 | 8/2014 | Duggal et al. |
| 8,808,377 B2 | 8/2014 | Donner |
| 8,808,380 B2 | 8/2014 | Fox et al. |
| 8,808,389 B2 | 8/2014 | Reiley |
| 8,821,546 B2 | 9/2014 | Vaughan |
| 8,840,651 B2 | 9/2014 | Reiley |
| 8,894,708 B2 | 11/2014 | Thalgott et al. |
| 8,945,224 B2 | 2/2015 | Trieu |
| 8,979,928 B2 | 3/2015 | Donner |
| 8,992,579 B1 | 3/2015 | Gustine et al. |
| 9,017,407 B2 | 4/2015 | Donner |
| 9,039,768 B2 | 5/2015 | Voellmicke |
| 9,044,321 B2 | 6/2015 | Mauldin et al. |
| 9,060,815 B1 | 6/2015 | Gustine et al. |
| 2001/0005796 A1 | 6/2001 | Zdeblick et al. |
| 2001/0018616 A1 | 8/2001 | Schwab |
| 2001/0020143 A1 | 9/2001 | Stark et al. |
| 2002/0029784 A1 | 3/2002 | Stark et al. |
| 2002/0032484 A1 | 3/2002 | Hyde, Jr. |
| 2002/0068977 A1 | 6/2002 | Jackson |
| 2002/0082701 A1 | 6/2002 | Zdeblick et al. |
| 2002/0087161 A1 | 7/2002 | Randall et al. |
| 2002/0147461 A1 | 10/2002 | Aldrich et al. |
| 2002/0147496 A1 | 10/2002 | Belef et al. |
| 2002/0183846 A1 | 12/2002 | Kuslich et al. |
| 2003/0114931 A1 | 6/2003 | Lee et al. |
| 2003/0124486 A1 | 7/2003 | McDevitt |
| 2003/0181981 A1 | 9/2003 | Lemaire |
| 2003/0208202 A1 | 11/2003 | Falahee |
| 2004/0073216 A1 | 4/2004 | Lieberman |
| 2004/0127988 A1 | 7/2004 | Goble et al. |
| 2004/0162558 A1 | 8/2004 | Hegde et al. |
| 2004/0162616 A1 | 8/2004 | Simonton |
| 2004/0186482 A1 | 9/2004 | Kolb et al. |
| 2004/0199256 A1 | 10/2004 | Wang |
| 2004/0220668 A1 | 11/2004 | Eisermann et al. |
| 2004/0228901 A1 | 11/2004 | Trieu |
| 2004/0249675 A1 | 12/2004 | Stark et al. |
| 2004/0260286 A1 | 12/2004 | Ferree |
| 2005/0043660 A1 | 2/2005 | Stark et al. |
| 2005/0101887 A1 | 5/2005 | Stark et al. |
| 2005/0113652 A1 | 5/2005 | Stark et al. |
| 2005/0131539 A1 | 6/2005 | Kohrs |
| 2005/0149192 A1 | 7/2005 | Zucherman et al. |
| 2005/0154391 A1 | 7/2005 | Doherty et al. |
| 2005/0203515 A1 | 9/2005 | Doherty et al. |
| 2005/0216088 A1 | 9/2005 | McKinley et al. |
| 2005/0240264 A1 | 10/2005 | Tokish, Jr. et al. |
| 2005/0245925 A1 | 11/2005 | Iki et al. |
| 2005/0267482 A1 | 12/2005 | Hyde, Jr. |
| 2005/0273099 A1 | 12/2005 | Baccelli et al. |
| 2006/0054171 A1 | 3/2006 | Dall |
| 2006/0058876 A1 | 3/2006 | McKinley |
| 2006/0069438 A1 | 3/2006 | Zucherman et al. |
| 2006/0085068 A1 | 4/2006 | Barry |
| 2006/0089716 A1 | 4/2006 | Felix |
| 2006/0095134 A1 | 5/2006 | Trieu et al. |
| 2006/0129244 A1 | 6/2006 | Ensign |
| 2006/0147332 A1 | 7/2006 | Jones et al. |
| 2006/0161154 A1 | 7/2006 | McAfee |
| 2006/0167547 A1 | 7/2006 | Suddaby |
| 2006/0229729 A1 | 10/2006 | Gordon |
| 2007/0027543 A1 | 2/2007 | Gimble et al. |
| 2007/0055374 A1 | 3/2007 | Copf, Jr. et al. |
| 2007/0155588 A1 | 7/2007 | Stark et al. |
| 2007/0156241 A1 | 7/2007 | Reiley et al. |
| 2007/0162134 A1 | 7/2007 | Marnay et al. |
| 2007/0179621 A1 | 8/2007 | McClellan, III et al. |
| 2007/0198093 A1 | 8/2007 | Brodke et al. |
| 2007/0225714 A1* | 9/2007 | Gradl .................. A61B 17/746 |
| | | 606/326 |
| 2007/0239164 A1 | 10/2007 | Prager et al. |
| 2007/0265621 A1 | 11/2007 | Matthis et al. |
| 2007/0270879 A1 | 11/2007 | Isaza et al. |
| 2007/0270968 A1 | 11/2007 | Baynham |
| 2007/0276501 A1 | 11/2007 | Betz et al. |
| 2007/0293949 A1 | 12/2007 | Salerni et al. |
| 2007/0299525 A1 | 12/2007 | Binotto |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0039843 A1 | 2/2008 | Abdou |
| 2008/0045968 A1 | 2/2008 | Yu et al. |
| 2008/0065215 A1 | 3/2008 | Reiley |
| 2008/0140082 A1 | 6/2008 | Erdem et al. |
| 2008/0140207 A1 | 6/2008 | Olmos |
| 2008/0154314 A1 | 6/2008 | McDevitt |
| 2008/0183293 A1 | 7/2008 | Parry et al. |
| 2008/0228276 A1 | 9/2008 | Mathews et al. |

(56) References Cited

U.S. PATENT DOCUMENTS

| | | |
|---|---|---|
| 2008/0262621 A1 | 10/2008 | Gorek |
| 2008/0281425 A1 | 11/2008 | Thalgott et al. |
| 2008/0288081 A1 | 11/2008 | Scrafton et al. |
| 2008/0300685 A1 | 12/2008 | Carls et al. |
| 2009/0018660 A1 | 1/2009 | Roush |
| 2009/0024174 A1 | 1/2009 | Stark |
| 2009/0024217 A1 | 1/2009 | Levy |
| 2009/0043394 A1 | 2/2009 | Zdeblick et al. |
| 2009/0076553 A1 | 3/2009 | Wolter |
| 2009/0088849 A1 | 4/2009 | Armstrong et al. |
| 2009/0105833 A1 | 4/2009 | Hovda et al. |
| 2009/0105834 A1 | 4/2009 | Hovda et al. |
| 2009/0131986 A1 | 5/2009 | Lee et al. |
| 2009/0132035 A1 | 5/2009 | Roth et al. |
| 2009/0149957 A1 | 6/2009 | Burd et al. |
| 2009/0192621 A1 | 7/2009 | Winslow et al. |
| 2009/0216238 A1 | 8/2009 | Stark |
| 2009/0216276 A1 | 8/2009 | Pasquet |
| 2009/0248163 A1 | 10/2009 | King et al. |
| 2009/0259261 A1 | 10/2009 | Reiley |
| 2009/0259316 A1 | 10/2009 | Ginn et al. |
| 2009/0287254 A1 | 11/2009 | Nayet et al. |
| 2009/0306671 A1 | 12/2009 | McCormack et al. |
| 2010/0057204 A1 | 3/2010 | Kadaba |
| 2010/0094290 A1 | 4/2010 | Vaidya |
| 2010/0100135 A1 | 4/2010 | Phan |
| 2010/0106200 A1 | 4/2010 | Stark |
| 2010/0121160 A1 | 5/2010 | Stark et al. |
| 2010/0137910 A1 | 6/2010 | Cawley et al. |
| 2010/0137919 A1 | 6/2010 | Wolter |
| 2010/0152785 A1 | 6/2010 | Forton et al. |
| 2010/0179552 A1 | 7/2010 | Wolter |
| 2010/0185292 A1 | 7/2010 | Hochschuler et al. |
| 2010/0204795 A1 | 8/2010 | Greenhalgh |
| 2010/0211176 A1 | 8/2010 | Greenhalgh |
| 2010/0268228 A1 | 10/2010 | Petersen |
| 2010/0286779 A1 | 11/2010 | Thibodeau |
| 2010/0286785 A1 | 11/2010 | Grayson |
| 2010/0292796 A1 | 11/2010 | Greenhalgh |
| 2010/0292800 A1 | 11/2010 | Zubok |
| 2010/0305702 A1 | 12/2010 | Michelson |
| 2010/0305704 A1 | 12/2010 | Messerli |
| 2010/0324607 A1 | 12/2010 | Davis |
| 2010/0331981 A1 | 12/2010 | Mohammed |
| 2011/0034957 A1 | 2/2011 | Biedermann |
| 2011/0046737 A1 | 2/2011 | Teisen |
| 2011/0071568 A1 | 3/2011 | Ginn et al. |
| 2011/0071635 A1 | 3/2011 | Zhang et al. |
| 2011/0087294 A1 | 4/2011 | Reiley |
| 2011/0093074 A1 | 4/2011 | Glerum |
| 2011/0098816 A1 | 4/2011 | Jacob et al. |
| 2011/0098817 A1 | 4/2011 | Eckhardt et al. |
| 2011/0118796 A1 | 5/2011 | Reiley |
| 2011/0172774 A1 | 7/2011 | Varela |
| 2011/0184518 A1 | 7/2011 | Trieu |
| 2011/0184519 A1 | 7/2011 | Trieu |
| 2011/0184520 A1 | 7/2011 | Trieu |
| 2011/0185306 A1 | 7/2011 | Aravamudan |
| 2011/0238181 A1 | 9/2011 | Trieu |
| 2011/0264233 A1 | 10/2011 | Song |
| 2011/0295272 A1 | 12/2011 | Assell et al. |
| 2012/0010714 A1 | 1/2012 | Moskowitz et al. |
| 2012/0022535 A1 | 1/2012 | Mayer et al. |
| 2012/0022595 A1 | 1/2012 | Pham et al. |
| 2012/0029641 A1 | 2/2012 | Curran et al. |
| 2012/0035729 A1 | 2/2012 | Glerum |
| 2012/0083883 A1 | 4/2012 | Ginn |
| 2012/0116454 A1 | 5/2012 | Edidin et al. |
| 2012/0116806 A1 | 5/2012 | Stark et al. |
| 2012/0150300 A1 | 6/2012 | Nihalani |
| 2012/0185049 A1 | 7/2012 | Varela |
| 2012/0209388 A1 | 8/2012 | Curran et al. |
| 2012/0259370 A1 | 10/2012 | Vaidya |
| 2012/0271200 A1 | 10/2012 | Martinson et al. |
| 2012/0271424 A1 | 10/2012 | Crawford |
| 2012/0296428 A1 | 11/2012 | Donner et al. |
| 2012/0316565 A1 | 12/2012 | Stark |
| 2012/0323285 A1 | 12/2012 | Assell et al. |
| 2013/0006361 A1 | 1/2013 | Glerum |
| 2013/0018427 A1 | 1/2013 | Pham et al. |
| 2013/0023994 A1 | 1/2013 | Glerum |
| 2013/0030456 A1 | 1/2013 | Assell et al. |
| 2013/0035727 A1 | 2/2013 | Datta |
| 2013/0053854 A1 | 2/2013 | Schoenefeld et al. |
| 2013/0053902 A1 | 2/2013 | Trudeau |
| 2013/0053964 A1 | 2/2013 | Talwar |
| 2013/0060337 A1 | 3/2013 | Petersheim et al. |
| 2013/0066426 A1 | 3/2013 | Martinson et al. |
| 2013/0085535 A1 | 4/2013 | Greenhalgh et al. |
| 2013/0090735 A1 | 4/2013 | Mermuys et al. |
| 2013/0116790 A1 | 5/2013 | Seifert |
| 2013/0123850 A1 | 5/2013 | Schoenefeld et al. |
| 2013/0123923 A1 | 5/2013 | Pavlov et al. |
| 2013/0144343 A1 | 6/2013 | Arnett et al. |
| 2013/0158669 A1 | 6/2013 | Sungarian |
| 2013/0197590 A1 | 8/2013 | Assell et al. |
| 2013/0218215 A1 | 8/2013 | Ginn et al. |
| 2013/0226181 A1 | 8/2013 | Assell et al. |
| 2013/0231746 A1 | 9/2013 | Ginn et al. |
| 2013/0245703 A1 | 9/2013 | Warren et al. |
| 2013/0253650 A1 | 9/2013 | Ashley |
| 2013/0282012 A1 | 10/2013 | Stark |
| 2013/0295202 A1 | 11/2013 | Stark |
| 2013/0297035 A1 | 11/2013 | Reiley |
| 2014/0012330 A1 | 1/2014 | Johnson, II et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0039628 A1 | 2/2014 | DeLurio et al. |
| 2014/0046380 A1 | 2/2014 | Asfora |
| 2014/0074175 A1 | 3/2014 | Ehler et al. |
| 2014/0088707 A1 | 3/2014 | Donner et al. |
| 2014/0100662 A1 | 4/2014 | Patterson et al. |
| 2014/0114415 A1 | 4/2014 | Tyber |
| 2014/0135850 A1 | 5/2014 | Parent et al. |
| 2014/0135927 A1 | 5/2014 | Pavlov et al. |
| 2014/0142700 A1 | 5/2014 | Donner et al. |
| 2014/0156007 A1 | 6/2014 | Pabst et al. |
| 2014/0200618 A1 | 7/2014 | Donner et al. |
| 2014/0249581 A1 | 9/2014 | Stachniak |
| 2014/0257294 A1 | 9/2014 | Gedet et al. |
| 2014/0257399 A1 | 9/2014 | Rezach |
| 2014/0257408 A1 | 9/2014 | Trieu et al. |
| 2014/0257411 A1 | 9/2014 | Rezach |
| 2014/0257486 A1 | 9/2014 | Alheidt |
| 2014/0277460 A1 | 9/2014 | Schifano et al. |
| 2014/0277478 A1 | 9/2014 | Moore |
| 2014/0277504 A1 | 9/2014 | Forton et al. |
| 2014/0288601 A1 | 9/2014 | Baynham |
| 2014/0336763 A1 | 11/2014 | Donner et al. |
| 2014/0336775 A1 | 11/2014 | Reiley |
| 2014/0343678 A1 | 11/2014 | Suddaby et al. |
| 2015/0039037 A1 | 2/2015 | Donner et al. |
| 2015/0094765 A1 | 4/2015 | Donner et al. |
| 2015/0173805 A1 | 6/2015 | Donner et al. |
| 2015/0182268 A1 | 7/2015 | Donner et al. |
| 2015/0209087 A1 | 7/2015 | Donner et al. |
| 2015/0250612 A1 | 9/2015 | Schifano et al. |
| 2015/0342753 A1 | 12/2015 | Donner et al. |
| 2016/0184105 A1 | 6/2016 | Donner et al. |

FOREIGN PATENT DOCUMENTS

| | | |
|---|---|---|
| CN | 201073333 Y | 6/2008 |
| CN | 201139628 | 10/2008 |
| CN | 201275132 | 7/2009 |
| CN | 201275133 | 7/2009 |
| CN | 201275134 | 7/2009 |
| CN | 202235633 U | 5/2012 |
| DE | 102013011322 A1 | 5/2014 |
| EP | 1663037 B1 | 6/2006 |
| JP | 2007-275592 | 10/2007 |
| KR | 10-1037206 | 5/2011 |
| RU | 2364359 C1 | 8/2009 |

(56) References Cited

FOREIGN PATENT DOCUMENTS

| | | |
|---|---|---|
| WO | WO 93/08745 A1 | 5/1993 |
| WO | WO 95/23559 | 9/1995 |
| WO | WO 95/31947 | 11/1995 |
| WO | WO 98/48717 | 11/1998 |
| WO | WO 01/30264 A2 | 5/2001 |
| WO | WO 01/95823 A1 | 12/2001 |
| WO | WO 02/067759 A2 | 9/2002 |
| WO | WO 2006/020463 A1 | 2/2006 |
| WO | WO 2006/099270 | 9/2006 |
| WO | WO 2007/022790 A1 | 3/2007 |
| WO | WO 2007/115295 A2 | 10/2007 |
| WO | WO 2008/011410 A2 | 1/2008 |
| WO | WO 2008/088685 A2 | 7/2008 |
| WO | WO 2008/089537 A1 | 7/2008 |
| WO | WO 2009/011774 A2 | 1/2009 |
| WO | WO 2009/029074 A1 | 3/2009 |
| WO | WO 2009/108318 A2 | 9/2009 |
| WO | WO 2010/045749 A1 | 4/2010 |
| WO | WO 2010/065015 A1 | 6/2010 |
| WO | WO 2010/108166 A1 | 9/2010 |
| WO | WO 2011014135 A2 | 2/2011 |
| WO | WO 2011/056690 A2 | 5/2011 |
| WO | WO 2011/066053 A2 | 6/2011 |
| WO | WO 2011/087912 A1 | 7/2011 |
| WO | WO 2011/091349 A2 | 7/2011 |
| WO | WO 2012/015976 A1 | 2/2012 |
| WO | WO 2013/020123 A2 | 2/2013 |
| WO | WO 2013/166496 A1 | 11/2013 |
| WO | WO 2014/055529 A2 | 4/2014 |
| WO | WO 2014/074853 A1 | 5/2014 |

OTHER PUBLICATIONS

Atlihan et al. Anatomy of the Posterior Illiac Crest as a Reference to Sacral Bar Insertion. *Clin Orthop* 2004;418:141-145.

Baria, Dinah, "Sacroiliac Joint Biomechanics and Effects of Fusion" (2010). Open Access Dissertations. Paper 466. http://scholarlyrepository.miami.edu/oa_dissertations, 179 pages.

Belanger, et al. "Sacroiliac Arthrodesis Using a Posterior Midline Fascial Splitting Approach and Pedicle Screw Instrumentation: A New Technique." Journal of Spinal Disorders, vol. 14 No. 2, pp. 118-124, 2001.

Buchowski, et al. "Functional and Radiographic Outcome of Sacroiliac Arthrodesis for the Disorders of the Sacroiliac Joint." The Spine Journal, 5, 2005, pp. 520-528.

Cecil et al. Projection of the S2 Pedicle Onto the Posterolateral Surface of the Ilium: A Technique for Lag Screw Fixation, Sacral Fractures or Sacroiliac Joint Dislocations. *Spine* 1996;21(7):875-878.

Chang et al. Low Profile Pelvic Fixation. *Spine* 2009;34(5):436-440.

Dall et al., *Surgery for the Painful, Dysfunctional Sacroiliac Joint*, Springer International Publishing, Switzerland, 2015.

Dayer R. et al. Pelvic fixation for neuromuscular scoliosis deformity correction. *Curr Rev Musculoskelet Med* (2012) 5:91-101.

DePuy Spine. ISOLA® Spinopelvic System, Surgical Technique. c. 2003 DePuy Spine, Inc., 28 pages.

Ebraheim, et al. "A Posterior Approach for Inspection of Reduction of Sacroiliac Joint Disruption." Surg. Radiol. Anat., 1999, 21(5), pp. 305-307.

Ebraheim, et al. "Anatomic considerations for Posterior Approach to the Sacroiliac Joint." Spine, 21(23), Dec. 1, 1996, pp. 2709-2712.

Garrido B.J. et al. Navigated placement of iliac bolts: description of a new technique. *The Spine Journal* 11 (2011) 331-335.

Giannikas, et al. "Sacroiliac Joint Fusion for Chronic Pain: A Simple Technique Avoiding the Use of Metalwork." Eur. Spine J, 13, 2004, pp. 253-256.

Globus Medical. REVERE® ADDITION® Sacroiliac Components, Surgical Technique. c. 2012 Globus Medical, 64 pages.

Globus Medical. SI-LOK™ Sacroiliac Joint Fixation System, Surgical Technique. c. 2011 Globus Medical, 44 pages.

Guner, et al. "Anterior Sacroiliac Fusion. A New Video-Assisted Endoscopic Technique." Surgical Laparoscopy & Endoscopy, 8(3), pp. 233-236.

LDR. Avenue® L Lateral Lumbar Cage. Sep. 2011, 3 pages.

LDR. ROI-A™ Anterior Approach Implant. Apr. 2008, 2 pages.

LDR. Surgical Technique ROI-C™ Anterior Cervical Cage. Apr. 2010, 15 pages.

Lee et al. Trajectory of Transsacral Iliac Screw for Lumbopelvic Fixation. *J Spinal Disord Tech* 2011;24(3):151-156.

Lehman, Jr. et al. Advantage of Pedicle Screw Fixation Directed Into the Apex of the Sacral Promontory Over Bicortical Fixation. *Spine* 2002;27(8):806-811.

Liebergall, Meir (Iri) M.D., *Lumbosacral and Spinopelvic Fixation*, Lippincott-Raven, Philadelphia, PA, 1996, Chap. 48, "Sacroiliac Joint Fusion," pp. 611-618.

Luk et al. A Stronger Bicortical Sacral Pedicle Screw Fixation Through the S1 Endplate. *Spine* 2005;30(5):525-529.

Margulies, J.Y. et al., *Movement, Stability & Low Back Pain, The essential role of the pelvis*, Churchill Livingstone, London, 1997, Chapters 44-47, "Surgical Fusion of the Spine to the Sacrum, etc.," pp. 555-593.

Marotta N. et al. A novel minimally invasive presacral approach and instrumentation technique for anterior L5-S1 intervertebral disectomy and fusion. *Neurosurg Focus*, vol. 20, Jan. 2006, 8 pages.

Martin et al. Sacropelvic Fixation: Two Case Reports of a New Percutaneous Technique. *Spine* 2011;36(9):E618-21.

McLauchlan, et al. "Sacral and Iliac Articular Cartilage Thickness and Cellularity: Relationship to Subchrondral Bone End-Plate Thickness and Cancellous Bone Density." Rheumatology 2002; 41:375-380.

Medtronic Sofamor Danek. Colorado 2™ Sacro-Iliac Fixation, Surgical Technique. © 2003 Medtronic Sofamor Danek USA, Inc.

Medtronic Sofamor Danek. Colorado 2™ The New Revolution, Surgical Technique. ©2000 Medtronic Sofamor Danek, Inc.

Mendel et al. The Lateral Sacral Triangle—A Decision Support for Secure Transverse Sacroiliac Screw Insertion. *Injury J. Care Injured* 2010;42(2011):1164-1170.

Moshirfar et al. Pelvic Fixation in Spine Surgery. *The Journal of Bone & Joint Surgery* 2005;87-A(2 Suppl):89-106.

O'Brien et al. An Anatomic Study of the S2 Iliac Technique for Lumbopelvic Screw Placement. *Spine* 2009;34(12):E439-E442.

O'Brien et al. Feasibility of Minimally Invasive Sacropelvic Fixation. *Spine* 2010;35(4):460-464.

O'Brien et al. Sacropelvic Instrumentation: Anatomic and Biomechanical Zones of Fixation. *Seminars in Spine Surgery* 2004;16(2):76-90.

Ouellet et al. Surgical Anatomy of the Pelvis, Sacrum, and Lumbar Spine Relevant to Spinal Surgery. *Seminars in Spine Surgery* 2004 Elsevier Inc.;16:91-100.

Pan W. et al. The invention of an iliosacral screw fixation guide and its preliminary clinical application. *Orthopaedic Surgery* (2012), vol. 4, No. 1, pp. 55-59.

Puhakka, et al. "MR Imaging of the Normal Sacroiliac Joint with Correlation to Histology." Skeletal Radiol., 33, 2004, pp. 15-28.

SI-Bone iFuse Implant System, Surgical Technique Manual. c. 2011 SI-Bone, Inc., 35 pages.

SI-Bone iFuse Implant System™. SI-Bone, Inc. 2010, 4 pages.

Signus Medizintechnik GmbH. Diana Operationstechnik. Rev. 2010-05/01, 20 pages.

Sponseller P.D. et al. Low profile pelvic fixation with the sacral alar iliac technique in the pediatric population improves results at two-year mninimum follow-up. *Spine* vol. 35, No. 20, pp. 1887-1892.

Stark J. G. et al. The history of sacroiliac joint arthrodesis: a critical review and introduction of a new technique. *Current Orthopaedic Practice*, vol. 22, No. 6, Nov./Dec. 2011, pp. 545-557.

Stark. "The Diagnosis and Treatment of Sacroiliac Joint Abnormalities." Current Orthopedic Practice, 21(4), Jul./Aug. 2010, pp. 336-347.

Synthes GmbH. Sacral Bars. Fixation of the posterior pelvis in cases of fractures or sacroiliac joint dislocations. © Apr. 2009 Synthes, Inc.

(56) References Cited

OTHER PUBLICATIONS

Synthes Spine. ProDisc-C Total Disc Replacement. Product Information. © 2008 Synthes, Inc., 14 pages.
Synthes Spine. SynFix-LR System. Instruments and implants for stand-alone anterior lumbar interbody fusion (ALIF). Technique Guide. © 2008 Synthes, Inc., 45 pages.
Synthes Spine. Universal Spinal System (USS) Polyaxial and Iliosacral Spine Fixation. A versatile system for posterior stabilization of spinal segments. Technique Guide, c. 2009 Synthes, Inc., 61 pages.
Szadek, et al. "Possible Nociceptive Structures in the Sacroiliac Joint Cartilage: An Immunohistochemical Study." Clinical Anatomy, 23, 2010, pp. 192-198.
Tenon Medical, *Catamaran SI Joint Implant*, http://tctig.com/projects (last visited Nov. 19, 2014).
tifix® Technology Pressure Plate Technology: Multidirectional Locking Technology Titanium Plate and Screw Systems, General & Specific Instructions. litos/GmbH & Co. KG, Rev: Sep. 9, 2008.
Tobler W.D. et al. The presacral retroperitoneal approach for axial lumbar interbody fusion. *J Bone Joint Surg* [Br], vol. 93-B, No. 7, Jul. 2011, pp. 955-60.
Ugur, et al. "New Needle Holder Facilitates Percutaneous Fluoroscopy-Guided Sacroiliac Puncture." Acta Radiologica, 2006, 47(5), pp. 481-483.
Vanelderen, et al. "Evidence-Based Medicine. Evidence-Based Interventional Pain Medicine According to Clinical Diagnoses. 13. Sacroiliac Joint Pain." Pain Practice, 10(5), 2010, pp. 470-478.
Waisbrod, et al. "Sacroiliac Joint Arthrodesis for Chronic Lower Back Pain." Arch. Orthop. Trauma Surg., 106, 1987, pp. 238-240.
Wise, et al. "Minimally Invasive Sacroiliac Arthrodesis. Outcomes of a New Technique." Spinal Disord. Tech., 21(8), Dec. 2008, pp. 579-584.
Yin, et al. "Sensory Stimulation-Guided Sacroiliac Joint Radiofrequency Neurotomy: Technique Based on Neuroanatomy of the Dorsal Sacral Plexus." Spine, 28(20), pp. 2419-2425.
Zyga Technology, Inc. SImmetry Sacroiliac Joint Fusion System, Surgeon Didactic, c. 2012 Zyga Technology, Inc., 45 pages.
Zyga Technology, Inc. SImmetry Sacroiliac Joint Fusion System, Technique Guide, known at least as early as Mar. 1, 2013, 20 pages.
Advisory Action, U.S. Appl. No. 12/998,712, dated Jan. 28, 2014, 4 pages.
Advisory Action, U.S. Appl. No. 13/135,381, mailed Jul. 23, 2013, 3 pages.
Amendment Under 1.312, U.S. Appl. No. 13/475,695, dated Mar. 25, 2016.
Amendment Under 1.312, U.S. Appl. No. 13/946,790, dated Dec. 14, 2015.
Appeal Brief, U.S. Appl. No. 13/135,381, dated Dec. 23, 2013, 20 pages.
Australian Examination Report, AU2014204494, dated May 15, 2015.
Chinese Office Action, CN201180001537.4, dated Mar. 19, 2015.
EP Examination Report, EP11733183.5, dated Sep. 9, 2015.
European Search Report, EP Appl. No. 11733183.5, dated Dec. 18, 2013, 4 pages.
European Search Report, EP Appl. No. 12799773.2, dated Oct. 29, 2014.
European Search Report, EP12834000.7, dated Jul. 13, 2015.
Examination Report, SG Application No. 201205104-1, dated Jul. 17, 2014, Intellectual Property Office of Singapore.
Final Rejection, U.S. Appl. No. 12/998,712, mailed Nov. 7, 2013, 24 pages.
Final Rejection, U.S. Appl. No. 13/135,381, mailed May 9, 2013, 14 pages.
Final Rejection, U.S. Appl. No. 13/236,411, dated Jan. 2, 2015.
Final Rejection, U.S. Appl. No. 13/945,053, dated Dec. 22, 2015.
International Search Report and Written Opinion, PCT application No. PCT/US2012/042823, dated Nov. 5, 2012, 16 pages.
International Search Report and Written Opinion, PCT Application No. PCT/US2012/055892, dated Mar. 25, 2013, 22 pages.
International Search Report and Written Opinion, PCT application No. PCT/US2011/000070, dated Mar. 21, 2011, 13 pages.
International Search Report and Written Opinion, PCT/US2014/030889, dated Jul. 16, 2014.
International Search Report and Written Opinion, PCT/US2014/048990, dated Nov. 18, 2014.
Japanese Office Action, JP2012-548960, dated Oct. 7, 2014.
Japanese Office Action, JP2015-042238, dated Dec. 22, 2015.
Non-Final Office Action, U.S. Appl. No. 13/945,053, dated Apr. 3, 2015.
Non-Final Office Action, U.S. Appl. No. 12/998,712, mailed May 31, 2013, 44 pages.
Non-Final Office Action, U.S. Appl. No. 12/998,712, dated Aug. 1, 2014.
Non-Final Office Action, U.S. Appl. No. 13/135,381, mailed Nov. 5, 2012, 19 pages.
Non-Final Office Action, U.S. Appl. No. 13/236,411, dated Apr. 11, 2014.
Non-Final Office Action, U.S. Appl. No. 13/475,695, dated Jul. 30, 2015.
Non-Final Office Action, U.S. Appl. No. 14/567,956, dated Feb. 12, 2016.
Notice of Allowance, U.S. Appl. No. 13/236,411, dated Mar. 16, 2015.
Notice of Allowance, U.S. Appl. No. 12/998,712, dated Dec. 23, 2014.
Notice of Allowance, U.S. Appl. No. 13/135,381, dated Apr. 17, 2014.
Notice of Allowance, U.S. Appl. No. 13/475,695, dated Feb. 18, 2016.
Notice of Allowance, U.S. Appl. No. 13/945,053, dated Mar. 28, 2016.
Notice of Allowance, U.S. Appl. No. 13/946,790, dated Nov. 20, 2015.
Notice of Allowance, U.S. Appl. No. 13/946,790, dated Feb. 16, 2016.
Response to Advisory Action, U.S. Appl. No. 13/135,381, filed Aug. 20, 2013, 12 pages.
Response to Final Office Action, U.S. Appl. No. 13/236,411, dated Mar. 4, 2015.
Response to Final Office Action, U.S. Appl. No. 12/998,712, dated Jan. 7, 2014, 16 pages.
Response to Final Office Action, U.S. Appl. No. 13/135,381, filed Jul. 9, 2013, 11 pages.
Response to Non-Final Office Action, U.S. Appl. No. 13/135,381, filed Feb. 4, 2013, 7 pages.
Response to Non-Final Office Action, U.S. Appl. No. 12/998,712, filed Aug. 28, 2013, 17 pages.
Response to Non-Final Office Action, U.S. Appl. No. 12/998,712, dated Sep. 4, 2014.
Response to Non-Final Office Action, U.S. Appl. No. 13/236,411, dated Sep. 11, 2014.
Response to Non-Final Office Action, U.S. Appl. No. 13/475,695, dated Oct. 30, 2015.
Response to Non-Final Office Action, U.S. Appl. No. 13/945,053, dated Aug. 31, 2015.
Response to Restriction, U.S. Appl. No. 13/946,790, dated Sep. 14, 2015.
Response to Restriction, U.S. Appl. No. 13/236,411, filed Jun. 10, 2013, 13 pages.
Response to Restriction, U.S. Appl. No. 13/236,411, filed Nov. 12, 2013, 14 pages.
Response to Restriction, U.S. Appl. No. 13/945,053, dated Nov. 19, 2014.
Response to Restriction, U.S. Appl. No. 13/475,695, dated Jun. 30, 2015.
Response to Restriction, U.S. Appl. No. 14/216,975, dated Jan. 22, 2016.
Response to Restriction, U.S. Appl. No. 14/567,956, dated Jan. 19, 2016.
Restriction Requirement, U.S. Appl. No. 13/475,695, dated Mar. 30, 2015.

(56) References Cited

OTHER PUBLICATIONS

Restriction Requirement, U.S. Appl. No. 13/946,790, dated Jul. 14, 2015.
Restriction Requirement, U.S. Appl. No. 13/236,411, mailed May 10, 2013, 5 pages.
Restriction Requirement, U.S. Appl. No. 13/236,411, mailed Oct. 16, 2013, 7 pages.
Restriction Requirement, U.S. Appl. No. 13/945,053, dated Sep. 25, 2014.
Restriction Requirement, U.S. Appl. No. 14/216,975, dated Oct. 23, 2015.
Restriction Requirement, U.S. Appl. No. 14/567,956, dated Nov. 20, 2015.
Singapore Search Report and Written Opinion, SG Appl. No. 201205104-1, dated Oct. 31, 2013, 29 pages.
Supplemental Amendment, U.S. Appl. No. 12/998,712, dated Apr. 14, 2014, 14 pages.
Taiwan Examination Report, TW100114376, dated Oct. 5, 2015.
Amendment Under 1.312, U.S. Appl. No. 13/945,053, dated May 19, 2016.
AU Patent Examination Report No. 1, AU2012312658, dated Jul. 18, 2016.
Non-Final Office Action, U.S. Appl. No. 14/216,975, dated Jun. 20, 2016.
Notice of Allowance, U.S. Appl. No. 13/945,053, dated Jul. 5, 2016.
Response to Non-Final Office Action, U.S. Appl. No. 14/567,956, dated May 10, 2016.
Response to Restriction, U.S. Appl. No. 14/127,119, dated Jun. 6, 2016.
Restriction Requirement, U.S. Appl. No. 14/127,119, dated Apr. 5, 2016.
Restriction Requirement, U.S. Appl. No. 14/447,612, dated Jul. 6, 2016.
International Search Report and Written Opinion, PCT/US2013/051381, dated Nov. 4, 2013.
Amendment and Response to Restriction, U.S. Appl. No. 14/447,612, dated Sep. 2, 2016.
Non-Final Office Action, U.S. Appl. No. 14/127,119, dated Sep. 8, 2016.
Non-Final Office Action, U.S. Appl. No. 14/681,882, dated Oct. 6, 2016.
Notice of Allowance, U.S. Appl. No. 14/567,956, dated Sep. 13, 2016.
Response to Restriction, U.S. Appl. No. 14/344,876, dated Aug. 29, 2016.
Response to Restriction, U.S. Appl. No. 14/514,221, dated Oct. 24, 2016.
Restriction Requirement, U.S. Appl. No. 14/514,221, dated Aug. 25, 2016.

* cited by examiner

ORTHOPEDIC ANCHORING SYSTEM AND METHODS

CROSS REFERENCE TO RELATED APPLICATIONS

This application claims priority to U.S. Provisional Application No. 61/798,922 filed Mar. 15, 2013, which is entitled "Orthopedic Anchoring System and Methods", and also claims priority to U.S. Provisional Application No. 61/674,233, which is entitled "Orthopedic Anchoring System and Methods" filed Jul. 20, 2012.

All of the aforementioned applications are hereby incorporated by reference in their entireties into the present application.

FIELD OF THE INVENTION

Aspects of the present invention relate to systems and methods related to a medical apparatus. More specifically, the present invention relates to devices and methods for joint, vertebral or intervertebral joint reinforcement or immobilization.

BACKGROUND OF THE INVENTION

Reinforcement, stabilization, or fusion of a joint or vertebrae may be indicated as a treatment of an afflicted region of a patient. Examples of specific treatments include spinal stabilization, spinal fusion, posterolateral spinal fusion, vertebral immobilization or reinforcement, intervertebral joint immobilization or reinforcement, degenerative disk stabilization, repair of traumatic fracture or dislocation of the pelvis, treatment of degenerative arthritis, treatment of sacroiliitis (an inflammation or degenerative condition of the sacroiliac joint), osteitis condensans ilii, and treatments of other degenerative conditions of joints or vertebrae.

This reinforcement of intervertebral joints, sacroiliac joints, or other joint stabilizations may be accomplished by one or more existing methods, including inserting rods and/or other implants into the afflicted regions. These rods and/or other implants may be anchored in place using existing orthopedic fasteners such as pedicle screws. One limitation of many existing fusion procedures involves the challenge of situating a fusion implant in suitably close alignment with the removed tissues of the patient to achieve a stable fixation of the joint or vertebrae. Existing implant structures may have insufficient engagement with the articular surfaces or cortical bone of the joint for adequate fixation or fusion. This failure to sufficiently stabilize and fuse the joint with the conventional implant structures and methods may result in a failure to relieve the condition being treated.

It may be desirable to limit the movement and/or loosening over time of the anchoring implant and/or associated fasteners to enhance the long-term effectiveness of a fusion implant. Existing pedicle screws and/or implants may loosen, back out, or otherwise functionally degrade due to the cumulative effect of forces and torques experienced as a result of normal posture and/or movements including bending, sitting, walking, and any other typical movements. Therefore, there exists a need for a stabilized anchor that is resistant to these forces for applications in vertebral immobilization/stabilization, intervertebral immobilization/stabilization, sacroiliac joint immobilization, and other surgical interventions.

The inventive fusion system described herein addresses the problems associated with conventional methods and apparatuses used in fixation and fusion.

BRIEF SUMMARY OF THE INVENTION

Disclosed herein is an implant assembly for providing an anchor attached to a bone of a patient, the assembly comprising: a hollow elongate implant outer layer comprising a lumen wall defining a lumen; an elongate implant body comprising a locking element, wherein at least a portion of the implant body is situated within the lumen; and a fastener comprising an attachment fitting, wherein the attachment fitting is attached to the locking element in a locked mechanical engagement. The lumen opens to an outer layer proximal end opposite to an outer layer distal end of the implant outer layer. The outer layer is situated within a bore formed within the bone of the patient. The locking element is situated outside of the lumen of the implant outer layer. The locking element is situated within the lumen and the implant outer layer further includes a fastener opening aligned with the locking element, wherein the lumen opens to the fastener opening to provide access to the locking element through the lumen wall. The fastener opening may further includes an additional locking element that engages in cooperation with the locking element of the implant body to form the locked mechanical engagement with the attachment fitting of the fastener. The fastener fitting may be chosen from: a ball fitting, a rounded fitting, a cone fitting, and a divoted fitting. The locking element may be chosen from: a self-locking retaining ring, a slot, a threaded fitting, a divoted fitting, one or more projections forming a slot. The fastener may be chosen from a screw, a nail, a pin, and a staple. The lumen may include a cross-sectional profile that is essentially matched to an external cross-sectional profile of the implant body.

Also disclosed herein is a delivery tool for performing an orthopedic surgical procedure, including: an elongate targeting arm including a first arm end and a second arm end; a fastener guide releasably attached to the first arm end, wherein the fastener guide includes a fastener guide longitudinal axis and a fastener guide distal end; and an implant guide releasably attached to the second arm end, wherein the implant guide includes an implant guide longitudinal axis and an implant guide distal end. The targeting arm maintains a fixed arrangement of the fastener guide longitudinal axis and the implant guide longitudinal axis during the orthopedic surgical procedure. The targeting arm may include a single rigid element formed into an elongate shape chosen from: a curved arcuate shape, a polygonal shape, a right-angle shape. The fixed arrangement maintained by the targeting arm may include a coplanar alignment of the fastener guide longitudinal axis and the implant guide longitudinal axis and a non-adjustable angle ranging from about 60° to 90° between the fastener guide longitudinal axis and the implant guide longitudinal axis. The targeting arm may also include a first element and a second element, wherein the first element and the second element are formed into elongate shapes chosen from: a linear shape, a curved arcuate shape, and a polygonal shape. The first element may include the first end and an opposite first joined end, the second element may include the second end and an opposite second joined end, and the first joined end and the second joined end are joined in an adjustable locked mechanical engagement. The fixed arrangement may include a coplanar alignment of the fastener guide longitudinal axis and the implant guide longitudinal axis and an adjustable angle ranging from about 60° to 90° between the fastener guide longitudinal axis and the implant guide longitudinal axis. The targeting arm may include a first element and a second element, wherein the adjustable locked mechanical engagement is chosen from: a hinged engagement wherein a lockable hinged joint joins the first joined end and the second joined end; a clamped engagement wherein a first attachment device attached to the first joined end is removably attached to the second element at any position between the second end and the second joined end; and a telescoping arrangement wherein the first joined end is nested within the second joined end and the first joined end may be inserted into the second joined end or extended from the second joined end and then reversibly locked in place. The fastener guide may further include a tool releasably attached at the fastener guide distal end, wherein the tool is chosen from: a screwdriver head, a socket driver, a drill, a bone cutter, a fiber optic camera, a laser, a conduit, and any combination thereof. The implant guide may further include a tool releasably attached at the implant guide distal end, wherein the tool is chosen from: a screwdriver head, a drill, a bone cutter, a fiber optic camera, a laser, a conduit, and any combination thereof.

Also disclosed herein is an orthopedic anchoring system for providing a stable anchor attached to a bone of a patient, including an implant assembly. The implant assembly may further include a hollow elongate implant outer layer including an outer layer proximal end, an outer layer distal end opposite to the outer layer proximal end, and a lumen wall defining a lumen. The implant assembly may further include an elongate implant body including a body proximal end, and a locking element at a body distal end opposite to the body proximal end, wherein at least a portion of the implant body is situated within the lumen. The implant assembly may further include an elongate fastener including a fastener head at a fastener proximal end and an attachment fitting at a fastener distal end opposite to the fastener proximal end, wherein the attachment fitting is attached to the locking element in a locked mechanical engagement. The orthopedic anchoring system may further include a delivery tool including: an elongate targeting arm including a first arm end and a second arm end; a fastener guide releasably attached to the first arm end, wherein the fastener guide comprises a fastener guide longitudinal axis and a fastener guide distal end releasably attached to the fastener head; and an implant guide releasably attached to the second arm end, wherein the implant guide includes an implant guide longitudinal axis and an implant guide distal end releasably attached to the outer layer proximal end and/or the body proximal end. The targeting arm maintains a fixed arrangement of the fastener guide longitudinal axis and the implant guide longitudinal axis during the orthopedic surgical procedure. The lumen may open to the outer layer proximal end. The implant outer layer may be situated within a bore formed within the bone of the patient. The locking element may be situated outside of the lumen of the implant outer layer. The locking element may be situated within the lumen and the implant outer layer may further include a fastener opening aligned with the locking element, wherein the lumen opens to the fastener opening to provide access to the locking element through the lumen wall. The fastener opening may further include an additional locking element that engages in cooperation with the locking element of the implant body to form the locked mechanical engagement with the attachment fitting of the fastener. The fastener fitting may be chosen from: a ball fitting, a rounded fitting, a cone fitting, and a divoted fitting.

The locking element may be chosen from: a self-locking retaining ring, a slot, a threaded fitting, a divoted fitting, and one or more projections forming a slot. The fastener may be chosen from: a screw, a nail, a pin, and a staple. The fixed arrangement may include a coplanar alignment of the fastener guide longitudinal axis and the implant guide longitudinal axis and a fixed angle ranging from about 60° to 90° between the fastener guide longitudinal axis and the implant guide longitudinal axis. The fastener guide may further include a tool releasably attached at the fastener guide distal end, wherein the tool is chosen from: a screwdriver head, a socket driver, a drill, a bone cutter, a fiber optic camera, a laser, a conduit, and any combination thereof. The implant guide may further include a tool releasably attached at the implant guide distal end, wherein the tool is chosen from: a screwdriver head, a drill, a bone cutter, a fiber optic camera, a laser, a conduit, and any combination thereof.

Also disclosed herein is a method for performing an orthopedic surgical procedure to treat an afflicted region of a patient, including providing a delivery tool including an elongate targeting arm comprising a first arm end and a second arm end, a fastener guide releasably attached to the first arm end, wherein the fastener guide includes a fastener guide longitudinal axis and a fastener guide distal end, and an implant guide releasably attached to the second arm end, wherein the implant guide includes an implant guide longitudinal axis and an implant guide distal end. The targeting arm maintains a fixed arrangement of the fastener guide longitudinal axis and the implant guide longitudinal axis during the orthopedic surgical procedure. The method also includes: forming a bore within a bone within the afflicted region by removing a portion of the bone using a bone removal tool reversibly attached to the implant guide distal end and reversibly attaching an outer layer proximal end of an implant outer layer to the implant guide distal end, wherein the implant outer layer further includes a lumen wall defining a lumen, the lumen opening to the outer layer proximal end situated opposite to an outer layer distal end. The method also comprises inserting the outer layer distal end into the bore to situate at least a portion of the implant outer layer within the bore and reversibly attaching a body proximal end of an implant body to the implant guide distal end, wherein the implant body further includes a locking element and a body distal end situated opposite to the body proximal end. The method also includes inserting the body proximal end into the lumen to situate at least a portion of the implant body within the lumen and reversibly attaching a fastener head of a fastener situated at a fastener proximal end to the fastener guide distal end, wherein the fastener further includes an attachment fitting situated at a fastener distal end opposite to the fastener proximal end. The method also includes engaging the attachment fitting of the fastener with the locking element of the implant body to form a locked mechanical engagement. The method may further include forming a fastener channel within the bone using a second bone removal tool reversibly attached to the fastener guide distal end. The bone removal tool and the second bone removal tool may be chosen from: a drill, a bone cutter, a fiber optic camera, a laser, a conduit, and any combination thereof.

Also disclosed herein is an orthopedic anchoring system including an implant assembly including: i) an implant body including at least a portion of a locking element; and ii) a fastener including an attachment feature configured to mechanically interlock with the locking element. The system also includes a delivery tool including: i) an implant guide configured to releasably couple to the implant body;

and a fastener guide operably coupled to the implant guide and configured to deliver the attachment feature of the fastener to the locking element. A final manufactured configuration of the delivery tool and a final manufactured configuration of the implant assembly are such that, when the system is assembled such that the implant guide is releasably coupled to the implant body, a delivery arrangement automatically exists such that the fastener guide is correctly oriented to deliver the attachment feature to the locking element. The system may further include an implant outer layer including a longitudinal axis and a lumen extending parallel to the longitudinal axis, wherein the lumen is configured to receive at least a portion of the implant body within the lumen. In being coupled together, the implant guide and fastener guide may form an angle relative to each other, and the angle is non-adjustable. The attachment feature may be configured to mechanically interlock with the locking element in a force-fit mechanical engagement. The locking element may be a self-locking retaining ring and the attachment feature may be a fastener distal end selected from a ball end, a rounded end, and a cone end attached to the fastener by a contracted neck region. The fastener distal end may be configured to be forced through the self-locking retaining ring to produce the force-fit mechanical engagement. The locking element may be situated near a distal end of the implant body. The distal end of the implant body may be configured to protrude from the lumen of the implant outer layer to expose the locking element. The implant outer layer may further include a fastener opening configured to provide a path through which the attachment feature passes to engage the locking element on a force-fit mechanical engagement. The attachment feature may be configured to mechanically interlock with the locking element in an interference mechanical engagement. The attachment feature may include a fastener distal end selected from a ball end, a rounded end, and a cone end attached to the fastener by contracted neck region; the locking element may include a slot formed within the implant body and extending from a distal end of the implant body in a direction parallel with the longitudinal axis, wherein the slot comprises a slot width between the diameter of the neck region and the diameter of the ball end; and the slot may be configured to receive the neck region of the attachment feature to retain the fastener distal end and to produce the interference mechanical engagement. The fastener may be situated in a final fastener position and the implant body may be advanced in a distal direction to form the interference mechanical engagement. The implant outer layer may further include a second locking element including a fastener opening configured to receive the attachment feature and to produce the interference mechanical engagement cooperatively with the locking element of the implant body when the implant body is advanced distally within the lumen of the implant outer layer. The implant outer layer may further include a first alignment feature and the implant body may further include a second alignment feature, wherein the first alignment feature is configured to operatively connect to the second alignment feature, resulting in a predetermined angular alignment of the implant body within the lumen about a rotational axis aligned parallel to the longitudinal axis and situated along a centerline of the implant body. The first alignment feature may include a first non-circular cross-sectional profile, the second alignment feature may include a second non-circular cross-sectional profile corresponding to the first non-circular cross-sectional profile, and the first cross-sectional profile and the second non-circular cross-sectional profile may be aligned only at the predetermined angular alignment. The first alignment feature may be chosen from a longitudinal ridge or groove formed on an outer surface of the implant body and aligned with the longitudinal axis, the second alignment feature may be chosen from a corresponding longitudinal groove or ridge formed on an inner surface defining the lumen of the implant outer layer and aligned with the longitudinal axis; and the longitudinal ridge or groove may meshes with the corresponding longitudinal groove or ridge as the implant body is advanced distally into the lumen only at the predetermined angular alignment. The implant guide may be further configured to releasably couple with the implant outer layer. The delivery tool may further include a targeting arm including a first arm end and an opposite second arm end, wherein the first arm end is configured to releasably attach the fastener guide and the second arm end is configured to releasably attach the implant guide to operatively couple the fastener guide and the implant guide. The targeting arm may include a fixed structural element configured to operatively couple the fastener guide and the implant guide at a non-adjustable angle relative to each other. The targeting arm may include two or more linked structural elements configured to operatively couple the fastener guide and the implant guide at an adjustable angle relative to each other.

Also disclosed herein is a method of implanting an orthopedic anchor, including: a) approaching a bore formed within a bone tissue with an implant body including at least comprising at least a portion of a locking element; b) delivering the joint implant body into the bore, the joint implant body being oriented in the bore such that the locking element is aligned opposite to an opening of the bore at a surface of the bone tissue; and c) causing an attachment feature of a fastener to mechanically interlock with the locking element. The method may further include approaching a bore formed within the bone tissue with an implant outer body and situating the implant body within a lumen formed within the implant outer layer. The method may further include: a) releasably coupling the implant outer layer to an implant guide of a delivery tool prior to approaching the bore; b) releasably coupling the implant inner layer to the implant guide prior to situating the implant within the lumen; and c) releasably coupling the fastener to a fastener guide of the delivery tool to cause the attachment feature of the fastener to mechanically interlock with the locking element; wherein the implant guide and the fastener guide are operably coupled such that, when the implant guide is releasably coupled to the implant body, a delivery arrangement automatically exists such that the fastener guide is correctly oriented to mechanically interlock the attachment feature with the locking element.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The following figures illustrate various aspects of the disclosure.

Corresponding reference characters and labels indicate corresponding elements among the views of the drawings. The headings used in the figures should not be interpreted to limit the scope of the claims.

DETAILED DESCRIPTION

Disclosed herein is an orthopedic anchoring system and method for providing structural support, reinforcement, and/or anchoring for a variety of orthopedic appliances. Non-limiting examples of orthopedic devices compatible with aspects of the orthopedic anchoring system include: vertebral reinforcement or immobilization devices; intervertebral joint reinforcement or immobilization devices; internal fixation devices; and any other orthopedic appliances or orthopedic applications known in the art.

Figure 1:
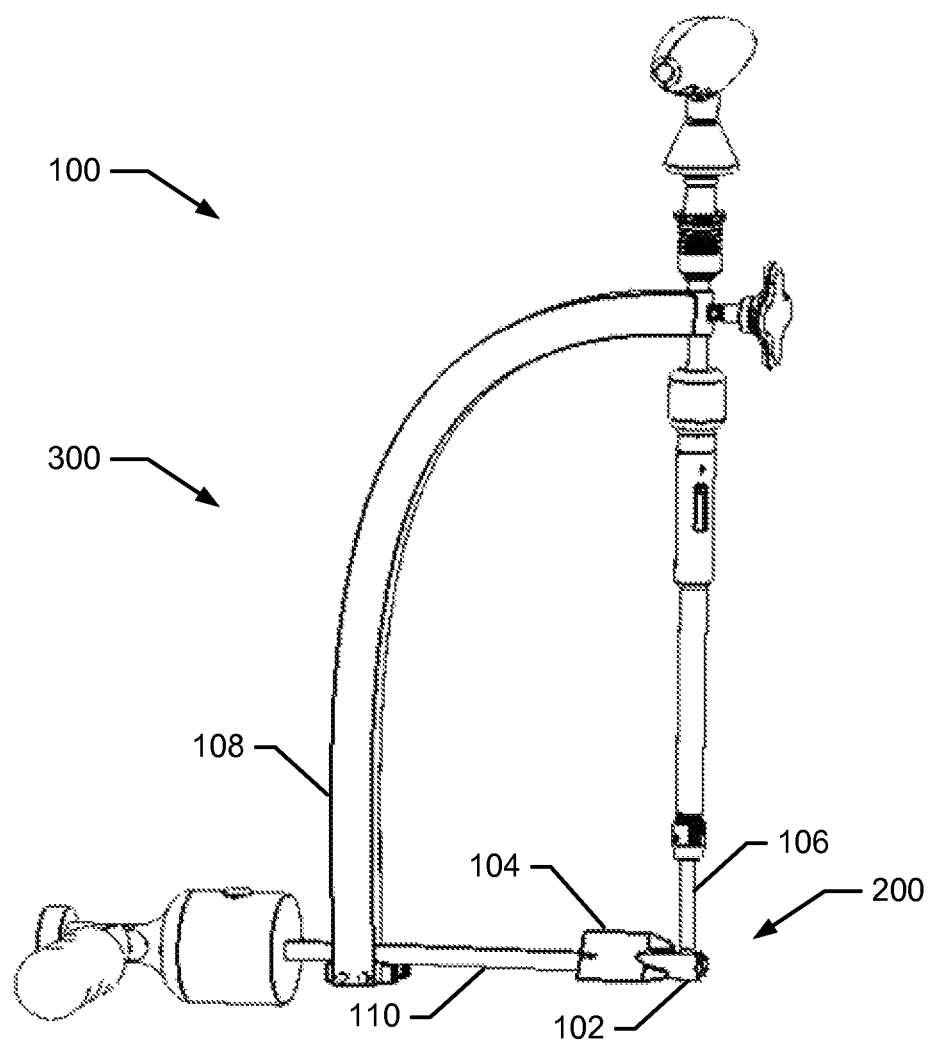
FIG. 1 is a side view of an orthopedic anchoring system.

A side view of the elements of an orthopedic anchoring system 100 is illustrated in FIG. 1. In an aspect, the system 100 includes an implant assembly 200 and a delivery tool 300. The implant assembly 200 may be situated and installed within a selected afflicted region of a patient, such as an intervertebral joint, using the delivery tool 300. In an aspect, the implant assembly 200 may include an implant body 102, an implant outer layer 104 and a fastener 106. The implant assembly 200 may provide a highly stable anchor that is resistant to loosening, backing out or otherwise functionally degrading due to the cumulative effect of forces and torques. In an aspect, the forces and torques may be experienced by the implant assembly 200 as a result of normal posture and/or movements including, but not limited to, bending, sitting, walking, and any other typical movements or postures. This stabilized orthopedic fastener 106 and other elements of the implant assembly 200 are particularly well-suited for a variety of orthopedic applications such as intervertebral joint immobilization, intervertebral joint stabilization, and other such surgical interventions.

The delivery tool 300 may facilitate the alignment and mechanical attachment of the fastener 106 to the implant body 102 in a safe and reliable manner. In an aspect, the delivery tool 300 may include a targeting arm 108 and a retaining rod 110. The retaining rod 110 may be releasably secured to the implant body 102 and/or the implant outer layer 104 when situating the implant assembly 200 within the afflicted region of the patient. The targeting arm 108 may situate and maintain the fastener 106 in precise alignment with the implant body 102 and/or implant outer layer 104 during insertion of the fastener 106 and the attachment of the fastener 106 to the implant body 102 and/or implant outer layer 104.

The implant body 102 may include additional features to provide additional functions to the implant body 102. Non-limiting examples of enhanced functions of the implant body 102 include: providing a receptacle and/or other means of mechanical attachment for the fastener 106; providing a means of detachably fastening a component of the delivery tool 300 such as the retaining rod 110 to the implant body 102 during the placement of the implant body 102; and facilitating the alignment and/or orientation of the implant body 102 within the implant outer layer 104 during the formation of the implant assembly 200.

Aspects of the orthopedic anchoring system 100 described herein provide a robust anchoring element for orthopedic appliances and devices. Various elements of the implant assembly 200, including the implant outer layer 104, may facilitate the integration of surrounding bone tissue into the peripheral margins of the implant assembly 200, further stabilizing the implant assembly 200.

Detailed descriptions of various embodiments of the implant assembly 200, delivery tool 300, and methods of using the system 100 are provided herein below.

I. Implant Assembly

Figure 2:
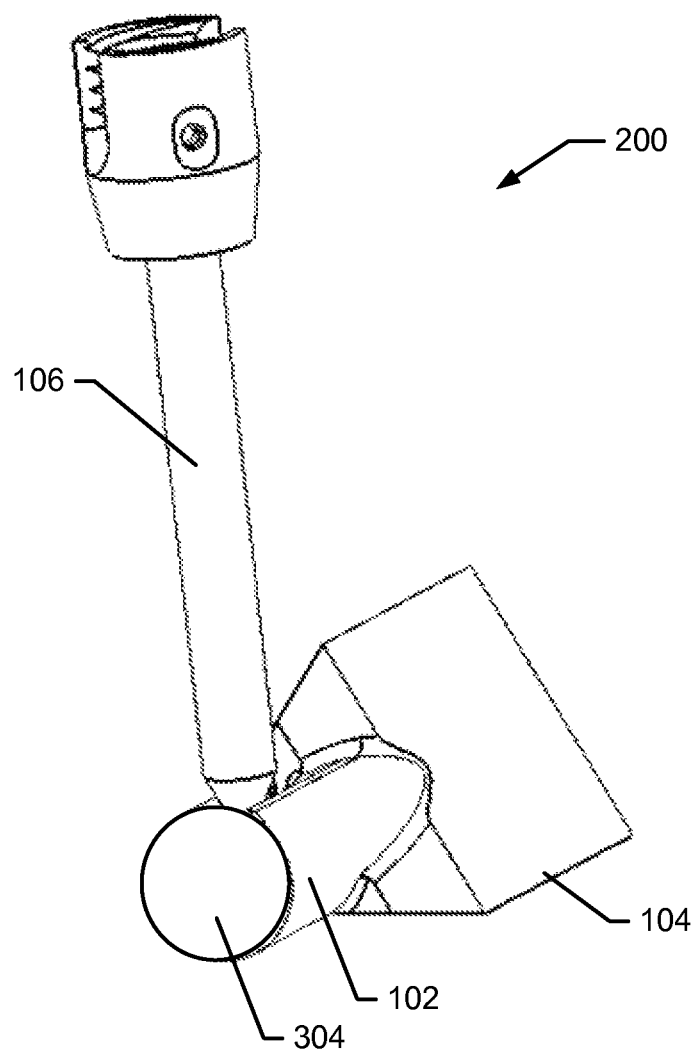
FIG. 2 is side view of an implant assembly.

The elements of an implant assembly 200 in one aspect are illustrated in FIG. 2. In this aspect, the implant assembly 200 may include an implant body 102, an implant outer layer 104 and a fastener 106. The implant outer layer 104 may house at least a portion of the implant body 102; a remaining portion of the implant body 102 may protrude from the implant outer layer 104, as illustrated in FIG. 2. The fastener 106 may mechanically attach to the implant body 102 and/or the implant outer layer 104. The implant outer layer 104 may be inserted within a bore (not shown) formed within bone tissue situated within or adjacent to an afflicted region of the patient to provide a stationary anchor for the implant body 102 and fastener 106. In an aspect, the implant body 102 and/or the implant outer layer 104 may further incorporate additional features to engage the fastener 106 in a locked mechanical attachment.

a. Implant Body

Figure 3:
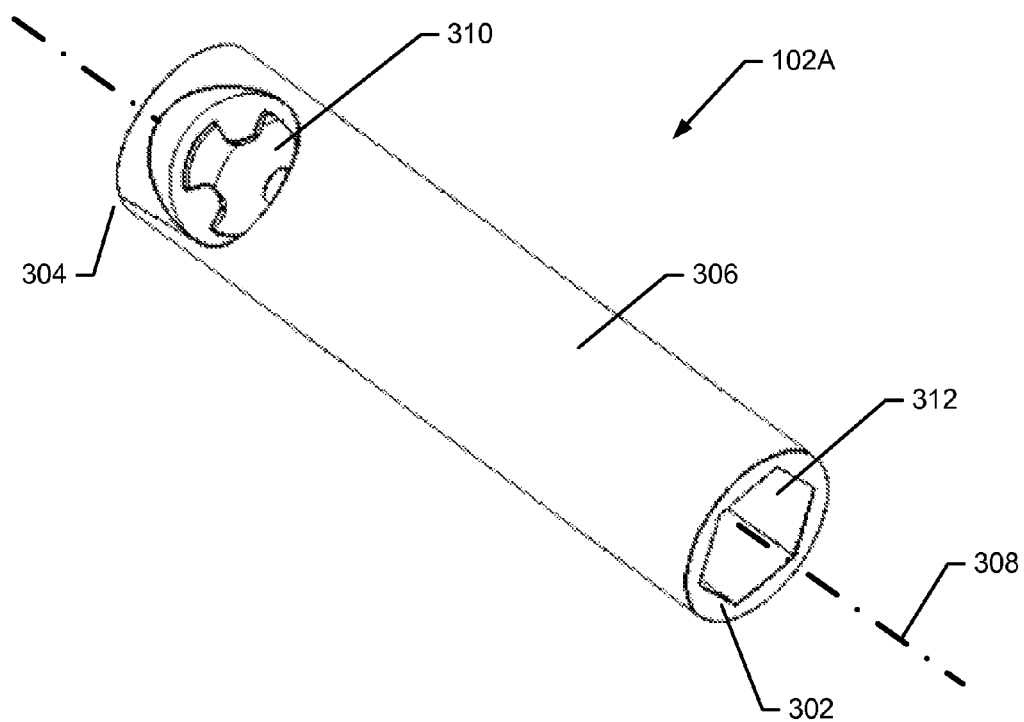
FIG. 3 is a proximal perspective view of a solid cylindrical implant body.

In various aspects, the implant body 102 may provide structural support and anchoring for the fastener 106. FIG. 3 is a drawing illustrating an implant body 102A in one aspect. In this aspect, the implant body 102A includes a body proximal end 302 and a body distal end 304. The implant body 102 may have an elongate cylindrical form, as illustrated in FIG. 3, or any other shape without limitation. Additional implant body 102 shapes in various aspects are described herein below.

The implant body 102 may further include a body external surface 306 and a body central axis 308 extending from the body proximal end 302 to the body distal end 304 of the implant body 102A and aligned with a longitudinal axis of the implant body 102. In various aspects, the implant body 102 may further include at least one locking element 310 for receiving the end of the fastener 106 (not shown), a tool fitting 312 for receiving an end of the retaining rod 110 (not shown) at the body proximal end 302 opposite the locking element 310, as well as ridges and/or grooves associated with the body external surface 306 for alignment of the implant body 102A within the implant outer layer 104 (not shown) during the process of assembling the implant assembly 200.

In one aspect, the implant body 102 may be machined, molded, formed, or otherwise manufactured from stainless steel, titanium, ceramic, polymer, composite, bone or other biocompatible materials.

i. Implant Body External Shape and Cross-sectional Shape

As indicated in FIGS. 3-7, the implant body 102 may have a variety of external shapes and cross-sectional profiles depending upon the desired properties and uses of the implant body 102. For example, different shapes, sizes, and/or cross-sectional profiles of the implant body 102 may be selected to accommodate various orthopedic surgical areas and/or procedures, patient morphologies, shapes and types of orthopedic fasteners, and/or any other relevant criterion.

The implant body 102 may be provided as any external shape without limitation, so long as the implant body 102 is capable of performing all aspects of the implant body's function. For example, the external shape may be selected to fit either partially or entirely within an interior lumen 1402 of the implant outer layer 104 in various aspects. In another example, the external shape may be selected to have a non-circular cross-section in order to inhibit rotation of the implant body 102 within the lumen 1402 of the implant outer layer 104. The external shape may be selected to include one or more longitudinal ridges or other features projecting outward or inward perpendicular to the body external surface 306 in an aspect. For example, the implant body 102 may include one or more longitudinal grooves 506 extending along the length of the implant body 102 and projecting inward relative to the body external surface 306, as illustrated in FIG. 5.

Figure 4:
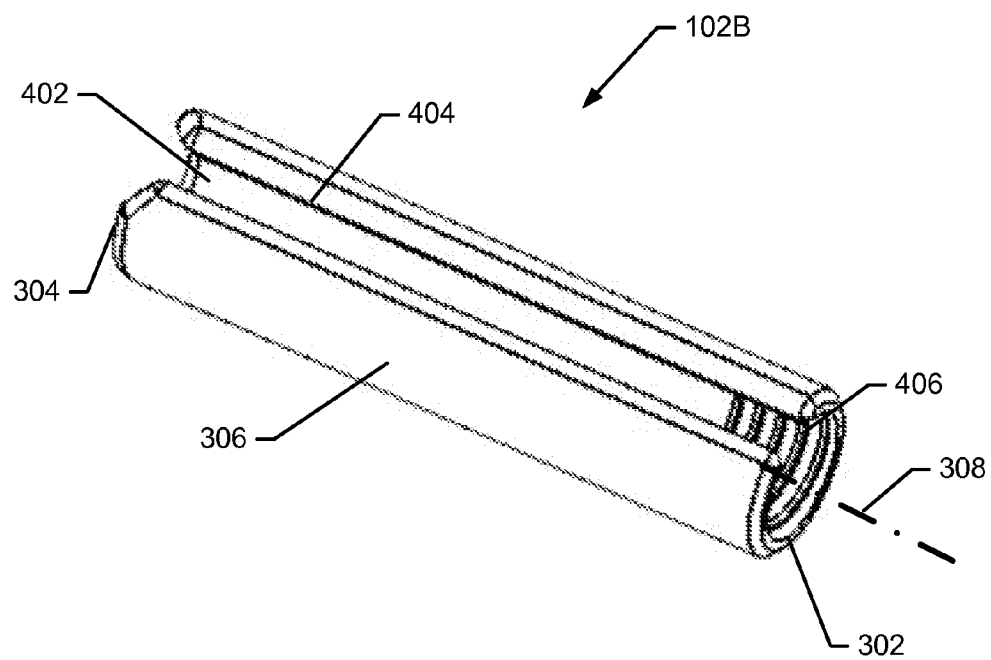
FIG. 4 is proximal perspective view of a hollow cylindrical implant body with a longitudinal groove.
Figure 5:
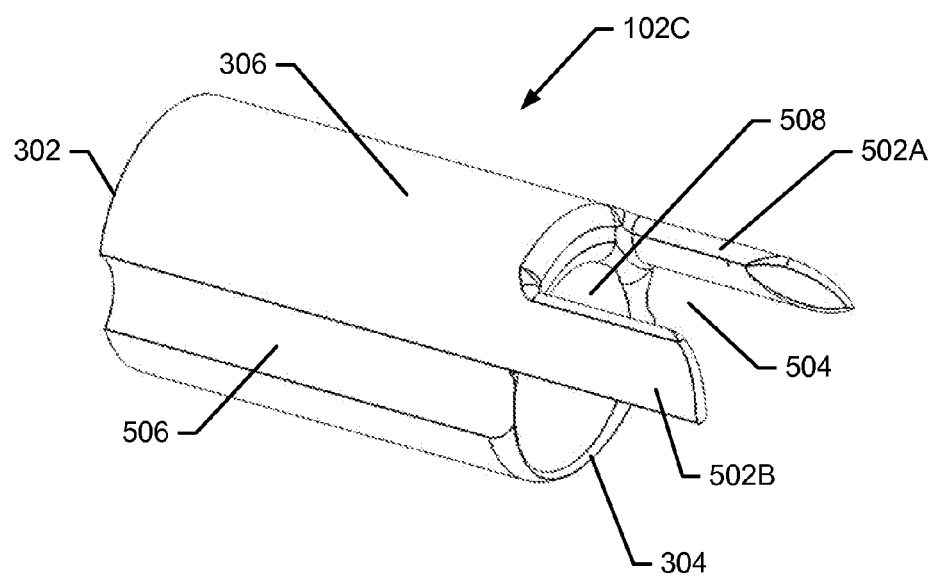
FIG. 5 is a distal perspective view of a solid cylindrical implant body with longitudinal projections.
Figure 6:
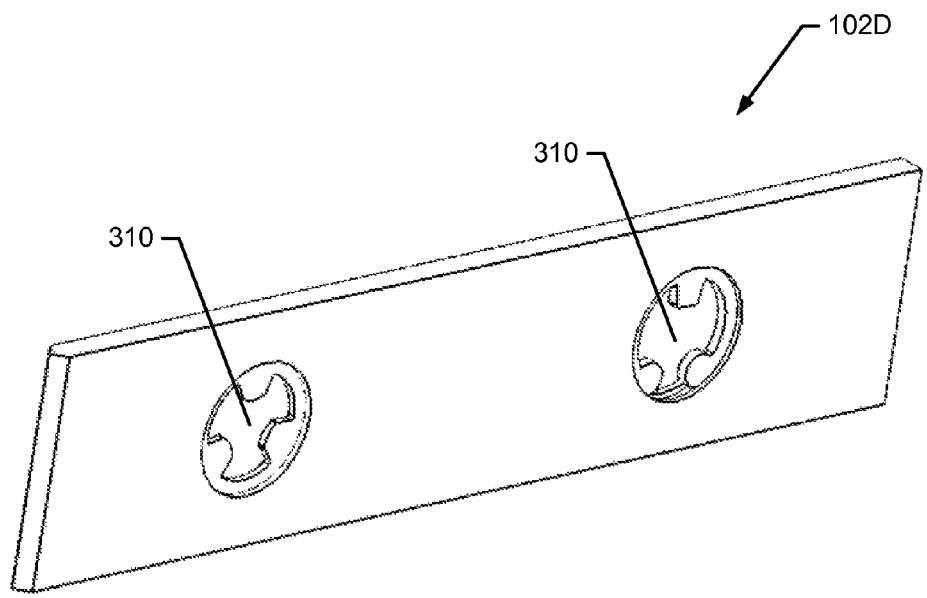
FIG. 6 is a top perspective view of a rectangular flat plate implant body with dual self-locking retaining rings.
Figure 7:
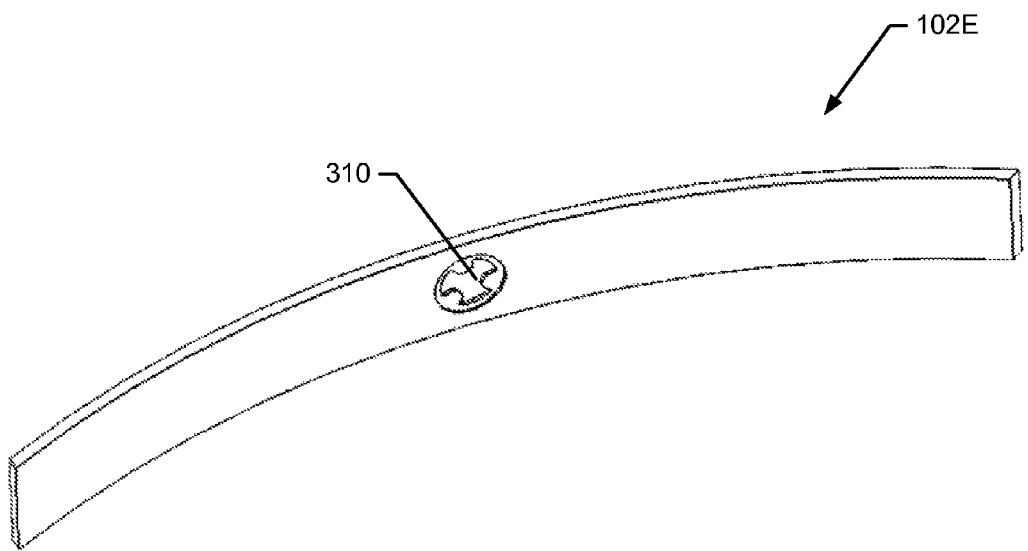
FIG. 7 is a bottom perspective view of a rectangular arcuate plate implant body with a single self-locking retaining ring.

Non-limiting examples of suitable external shapes for the implant body 102 include: a solid cylinder, as illustrated in FIG. 3 and FIG. 5; a hollow cylinder, as illustrated in FIG. 4; a planar flat plate, as illustrated in FIG. 6; or an arcuate flat plate, as illustrated in FIG. 7. In various aspects, the external shapes of the implant body 102 may be generally elongate such that the length of the implant body 102 from the body proximal end 302 to the body distal end 304 is longer than the thickness of the implant body 102. The implant body 102 may also be any length which allows a fastener 106 with a connection fitting to attach to the implant body 102 at the locking element 310.

In another aspect, the cross-sectional shape of the implant body 102 may have any solid or hollow profile, without limitation. Non-limiting examples of suitable cross-sectional shapes of the implant body include circular, elliptical, semi-circular, rectangular, triangular, any other polygonal geometry, and any other non-circular geometry. In an additional aspect, the cross-sectional shape and size may be uniform along the full length of the implant body 102 to facilitate the insertion of the implant body 102 into the lumen 1402 of the implant outer layer 104.

In yet another aspect, the implant body 102 may include a body lumen 402 contained within the interior of the implant body 102. The body lumen 402 may extend the entire length of the implant body 102, as illustrated in FIG. 4. In this aspect, the body lumen 402 extends from the body proximal end 302 to the body distal end 304. In other aspects, the body lumen 402 may extend only a portion of the length of the implant body 102. For example, the body lumen 402 may open outward through the body proximal end 302, but may be bounded somewhere between the body proximal end 302 and the body distal end 304 at a transition from a hollow body cross-section to a solid body cross-section. In another example, the body lumen 402 may open outward through the body distal end 304, but may be similarly bounded somewhere between the body proximal end 302 and the body distal end 304 at a transition from a hollow cross-section to a solid cross-section.

The body lumen 402 may further open laterally through the body external surface 306 in one or more regions along the length of the implant body 102. These one or more lateral openings may be in the form of discrete openings including, but not limited to, holes, slits, or any other discrete opening type. The one or more discrete openings may be arranged in any distribution without limitation. In one aspect, the one or more lateral openings may take the form of a longitudinal groove 404, as illustrated in FIG. 4. The lateral openings may provide various functions to the implant body 102 including, but not limited to: an alignment guide for aligning the implant body 102 within the implant outer layer 104 during the process of assembling the implant assembly 200; a structural feature forming at least a portion of a locking element 310; and/or a structural feature forming at least a portion of a tool fitting 312.

In another aspect, the implant body 102 may include one or more longitudinal projections extending in a direction essentially parallel with the body central axis 308 in a proximal and/or distal direction. For example, the implant body 102 may include a pair of longitudinal projections 502A and 502B as illustrated in FIG. 5. The longitudinal projections 502A and 502B may define the lateral sides of a slot 504 in this aspect. The slot 504 may function in a variety of ways in the implant assembly 200 including, but not limited to, functioning as part of a locking element 310.

Specific examples of the function of the features of the implant body as a tool fitting, a locking element, and other functions are described in further detail herein below.

ii. Tool Fitting

In various aspects, the implant body 102 includes a tool fitting 312 to provide a means of releasably connecting an end of the retaining rod 110 to the body proximal end 302 during insertion of the implant body 102 into the implant outer layer 104 and/or securing the implant body 102 in a fixed alignment while the fastener 106 is mechanically connected to the implant body 102.

Figure 8:
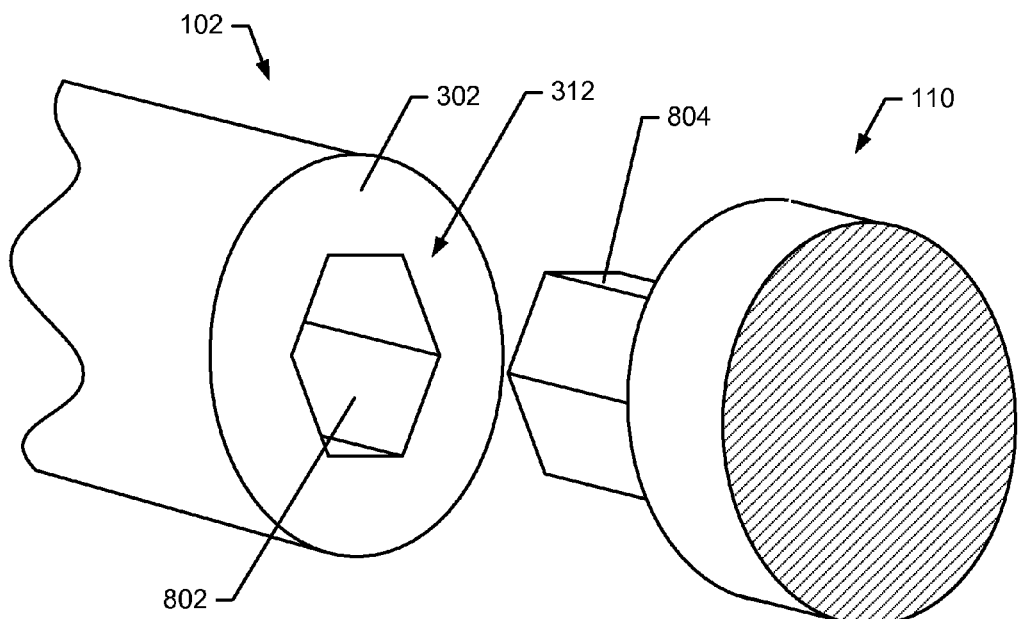
FIG. 8 is an exploded perspective view of a hexagonal tool receptacle and corresponding tool fitting.

The tool fitting 312 may be situated at the body proximal end 302 of the implant body 102 in one aspect, as illustrated in FIG. 3. In this aspect, the tool fitting 312 may be provided in the form of a hexagonal recess within the body proximal end 302. As illustrated in FIG. 8, the hexagonal cross-sectional shape and dimensions of the recess 802 forming the tool fitting 312 are selected such that a corresponding end 804 of the retaining rod 110, which also has a hexagonal cross-section, fits closely within the hexagonal recess 804 in this aspect. Any cross-sectional shape for the recess 802 forming the tool fitting 312 may be selected without limitation, so long as this cross-sectional shape corresponds to the cross-sectional shape of the corresponding end 804 of the retaining rod 110.

In another aspect (not shown), the end 804 of the retaining rod 110 may include a recess within which a tool fitting 312 in the form of a protrusion extending from the body proximal end 302 may fit. In this aspect, any cross-sectional shape for the recess within the end of the retaining rod 110 may be selected without limitation, so long as this cross-sectional shape is matched to the cross-sectional shape of the tool fitting 312 extending from the body proximal end 302. Any non-circular cross-section may be selected for the tool fitting 312 of the retaining rod 110 and corresponding body proximal end 302 including, but not limited to: any non-circular polygonal cross-section such as triangular, square, and hexagonal; other non-circular cross-sections such as elliptical.

Figure 9:
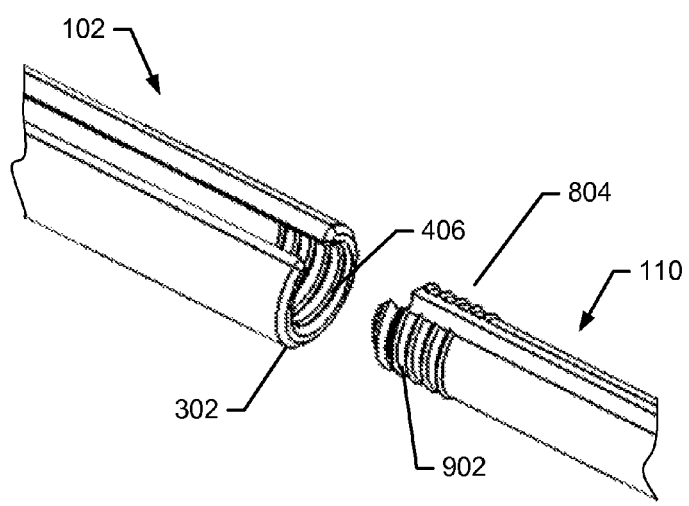
FIG. 9 is an exploded perspective view of a threaded tool receptacle and corresponding tool fitting.

The tool fitting 312 may incorporate other features such as corresponding threaded fittings to releasably connect the end of the retaining rod 110 to the body proximal end 302. Referring to FIG. 9, the body proximal end 302 may include a threaded receptacle 406 that receives a corresponding threaded end 902 of the retaining rod 110. In this aspect, the threaded end 902 may be advanced into the threaded receptacle 406 until the threaded end 902 has advanced the full extent of the threads in the threaded receptacle 406. In another aspect (not shown), the end of the retaining rod 110 may include a threaded recess into which a threaded end of the body proximal end 302 may be advanced to releasably connect the body proximal end 302 to the end of the retaining rod 110.

Figure 10:
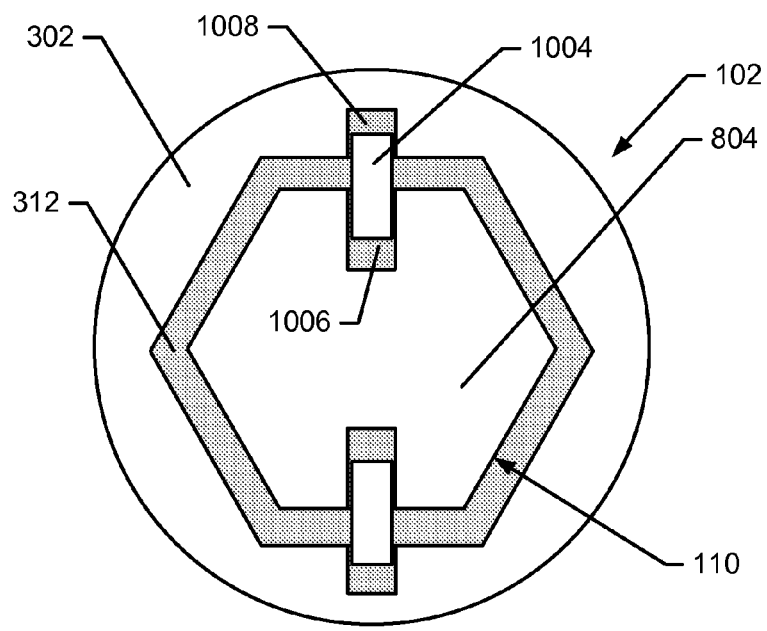
FIG. 10 is a transverse cross-sectional view of a hexagonal retaining rod with retractable pins.
Figure 11:
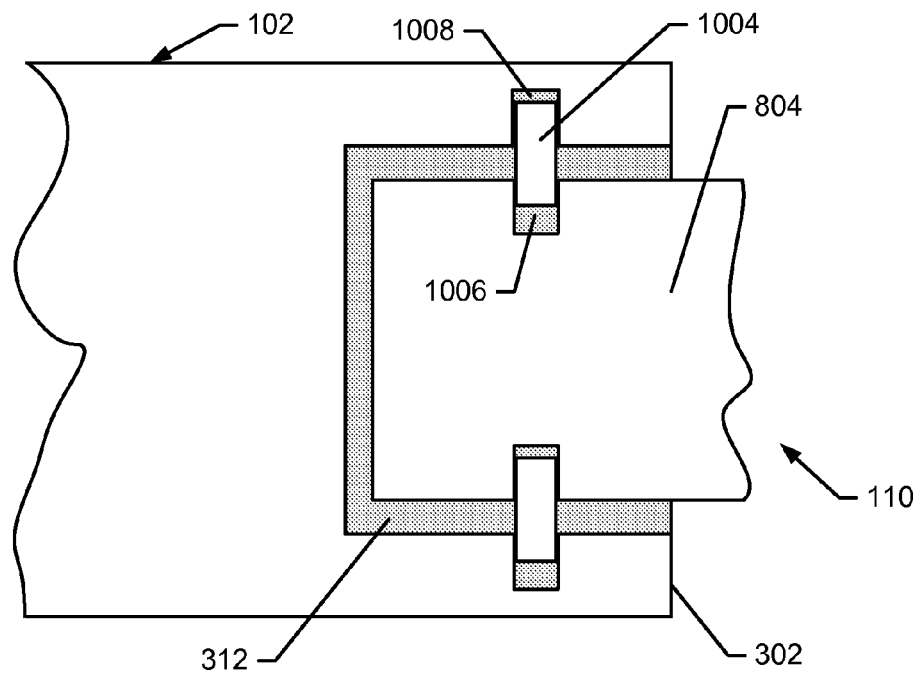
FIG. 11 is a longitudinal cross-sectional view of a retaining rod end inserted within a tool fitting.

In additional aspects, the tool fitting 312 may incorporate features such as retractable pins or fins to releasably connect the end of the retaining rod to the body proximal end. In one additional aspect, illustrated in FIG. 10 as a transverse cross-section, the retaining rod end 1002 may include one or more retractable pins 1004 or fins (not shown) that project laterally outward from the surface of the retaining rod end 1002 in an extended position. These one or more retractable pins 1004 may be retracted into corresponding inner receptacles 1006 formed within the retaining rod end 1002 during the insertion of the retaining rod end 1002 into the tool fitting 312 in the body proximal end 302. Upon insertion, the retaining rod end 1002 may be reversibly locked into place within the tool fitting 312 by extending the retractable pins 1004 radially outward to engage corresponding outer pin receptacles 1008 formed within the wall surrounding the tool fitting 312. After the implant assembly 200 is installed within the afflicted region of the patient, the retaining rod 110 may be removed from the implant body 102 by retracting the one or more retractable pins 1004 and sliding the retaining rod end 1002 from the tool fitting 312. FIG. 11 is a longitudinal cross-section of the retaining rod end 1002 inserted within the tool fitting 312, showing the retractable pins 1004 engaged with the corresponding outer pin receptacles 1008, thereby locking the retaining rod end 1002 in place.

In another additional aspect (not shown) the retractable pins 1004 may retract outward into the corresponding outer pin receptacles 1008 during insertion and/or removal of the retaining rod end 1002 from the tool fitting 312. The retaining rod end 1002 may be locked into the tool fitting 312 by extending the retractable pins 1004 radially inward to engage corresponding inner pin receptacles 1006 formed within the retaining rod end 1002.

iii. Locking Element

The implant body 102 may further include at least one locking element 310 for receiving a fastener 106. In various aspects, the locking element 310 may reversibly or irreversibly engage a corresponding attachment fitting 2810 of the fastener 106 in a locked engagement to form an anchor for an orthopedic appliance, orthopedic procedure, or other treatment of an afflicted region of a patient.

FIG. 3 is a perspective view of an implant body 102 that includes a locking element 310 in one aspect. The location of the locking element 310 on the implant body 102 may include, but is not limited to, any position situated between the body distal end 304 and the body proximal end 302, as well as extending distally away from the body distal end 304. The locking element 310 may extend any portion of the length of the implant body 102 from the body proximal end 302 to body distal end 304 up to the entire length of the implant body 102. For example, the longitudinal groove 404, shown illustrated in the perspective view of an implant body 102B in FIG. 4, may function as a locking element 310 that extends the entire length of the implant body 102B. As an additional example, as illustrated in the perspective view of FIG. 5, a slot 504 formed between a pair of longitudinal projections 502A and 502B may function as the locking element 310.

Any known means of securing a fastener 106 to a locking element 310 may be suitable for use in the implant assembly 200. Due to the limited visibility inherent in many orthopedic surgical procedures, a means of securing a blind fastener 106 may be particularly well-suited for use in the implant assembly 200. The type of locking element 310 may be selected to be compatible with the particular attachment fitting 2810 of the fastener 106 used in the implant assembly 200. The locking element 310 may further be selected to provide for limited movements of the fastener 106 in one or more predefined directions after the fastener is attached in a locked engagement with the locking element 310.

Non-limiting examples of suitable locking elements include: self-locking retaining ring, slots, threaded fittings, divoted fittings, and one or more longitudinal projections forming slots. The locking elements 310 may be situated entirely within or upon the implant body 102 in one aspect. In another aspect, at least one locking element 310 may be situated within or upon the implant body 102 and one or more other locking elements may be situated within or upon the implant outer layer 104. In this aspect, the locking elements of the implant body 102 and the implant outer layer 104 may interact in an interlocking manner to form the locked engagement with attachment fitting 2810 of the fastener 106. In additional aspects, the implant body 102 may include a single locking element 310, as illustrated in FIGS. 3-5 and FIG. 7, or the implant body 102 may include two or more locking elements 310, as illustrated in FIG. 6.

In one aspect, the locking element 310 opens laterally outward in a direction generally perpendicular to the body central axis 308 of the implant body 102. The opening formed by the locking element 310 may extend fully through the entire implant body, as illustrated in FIG. 6 and FIG. 7. In another aspect, the locking element 310 may extend from the body external surface 306 to the interior of the implant body 102, which may be of solid cross-section, as illustrated in FIG. 3. In yet another aspect, illustrated in FIG. 4, the locking element 310, provided in this aspect as a longitudinal groove 404, may extend from the body external surface 306 into the body lumen 402 of the hollow implant body 102B.

Figure 12:
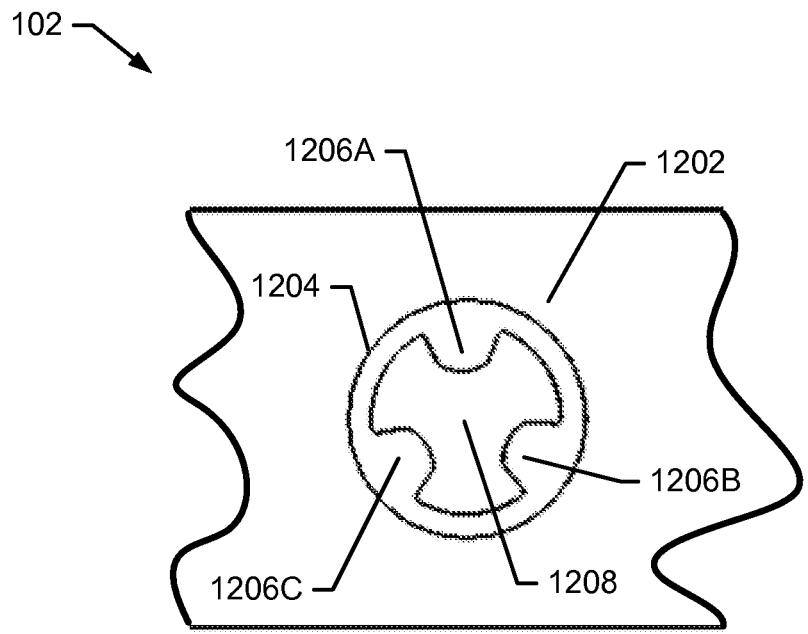
FIG. 12 is a top view of a self-locking retaining ring.

In another aspect, the locking element 310 may be a self-locking retaining ring 1202. A top view of a self-locking retaining ring 1202 is illustrated in FIG. 12. The self-locking retaining ring 1202 may include a planar circular opening 1204 with at least three arcuate members 1206A, 1206B, and 1206C distributed around a circumference of the planar circular opening 1204 and projecting radially inward toward a center 1208 of the planar circular opening 1204. The at least three arcuate members 1206A, 1206B, and 1206C may be separated by a distance corresponding to a narrowed region of the attachment fitting of the fastener 106 (not shown), described in detail herein below. The at least three arcuate members 1206A, 1206B, and 1206C may be flexible to facilitate the deformation of the arcuate members 1206A, 1206B, and 1206C to accommodate larger-diameter elements of the fastener 106 during its insertion into the self-locking retaining ring 1202. The self-locking retaining ring 1202 allows an attachment fitting of a fastener 106 to be inserted into the locking element 310 of the implant body 102 but restricts the movement of the fastener 106 out of the locking element 310 once inserted. A detailed description of the attachment of the fastener 106 to the implant body 102 via the self-locking retaining ring 1202 is provided herein below.

Figure 13:
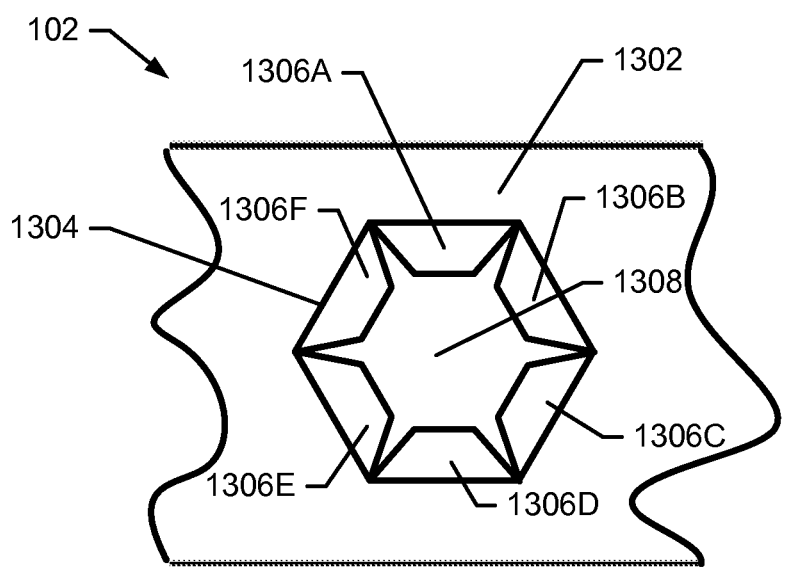
FIG. 13 is a top view of a hexagonal self-locking retaining ring.

In other aspects, the self-locking retaining ring 1202 may include a planar non-circular opening with at least three flexible arcuate or non-arcuate members projecting from a perimeter of the non-circular opening into a center of the non-circular opening. For example, the non-circular opening may be provided as a polygonal shape such as a hexagonal opening 1302, as illustrated in FIG. 13. In this aspect, six flexible non-arcuate members 1306A-1306F project from a perimeter of the hexagonal opening 1304 toward the hexagon center 1308. In other additional aspects, the self-locking retaining ring 1202 may be non-planar. For example, a locking element 310 such as a self-locking retaining ring 1202 may be provided as an arcuate shape to conform to the shape of an arcuate implant body 102E, as illustrated in FIG. 7.

In additional aspects the locking element 310 may be provided in the form of a longitudinal groove 404. Referring to FIG. 4, the longitudinal groove 404 may extend from the body distal end 304 to the body proximal end 302 of the implant body 102 and may be aligned parallel to the body central axis 308. In general, the longitudinal groove 404 may have any intermediate length up to the full length of the implant body 102. The dimensions of the longitudinal groove 404 including, but not limited to, groove width, groove depth, and any other groove dimension may be selected to provide a compatible fit with the corresponding attachment fitting of the fastener 106. For example, the longitudinal groove 404 may have a minimum width corresponding to the narrowest region of the attachment fitting 2810 of the fastener 106. This width may allow the attachment fitting 2810 of the fastener 106 to extend through the longitudinal groove 404 but retain the attachment fitting 2810 within the longitudinal groove 404 once the fastener 106 is inserted through the longitudinal groove 404.

In another aspect, the locking element 310 may be provided in the form of a slot 504 formed between a pair of longitudinal projections 502A and 502B as illustrated in FIG. 5. The longitudinal projections 502A and 502B may have a minimum length that is essentially equal to the cross-sectional diameter of the attachment fitting of the fastener 106. In this aspect, the longitudinal projections 502A and 502B may lock an attachment fitting of a fastener 106 using a meshing engagement with additional locking elements 310 formed within the implant outer layer 104, as described herein below. To facilitate this meshing engagement, the distal end 304 of the implant body 102 may further contain additional features including, but not limited to, a distal body depression 508 contoured to the shape of the attachment fitting 2810 of the fastener 106 that projects through the slot 504 after insertion of the fastener 106.

iv. Alignment Features

In an aspect, the implant body 102 may further include surface features on the body external surface 306 to guide the placement and/or orientation of the implant body 102 within the implant outer layer 104 during the formation of the implant assembly 200. These surface features may facilitate the alignment of the locking element 310 with a corresponding fastener opening 2202 in the implant outer layer 104. The surface features may limit the insertion depth of the implant body 102 through the implant outer layer 104 to ensure that the body distal end 304 protrudes from the implant outer layer 104 by an appropriate amount for purposes of alignment of the fastener 106 with the locking features of the implant outer layer 104 and/or locking element 310. The surface features may ensure an appropriate alignment of the fastener 106 locked within the implant outer layer 104 and/or the implant body 102 for function as an anchor.

Any known method of aligning a pair of nested elements may be selected for use as alignment features for the implant body 102 so long as the alignment features are compatible with corresponding alignment features of the implant outer layer 104. In one aspect, illustrated as a transverse cross-section in FIG. 14, the alignment feature may be provided in the form of a non-circular cross-sectional shape of the implant body 102 that may closely fit within a lumen 1402 of the outer layer 104 with a corresponding non-circular cross-sectional profile. In this aspect, the non-circular cross-sectional profile of the implant body 102 and lumen 1402 inhibit the rotation of the implant body 102 relative to the implant outer layer 104, thereby maintaining a predetermined alignment during the formation of the implant assembly 200.

Figure 15:
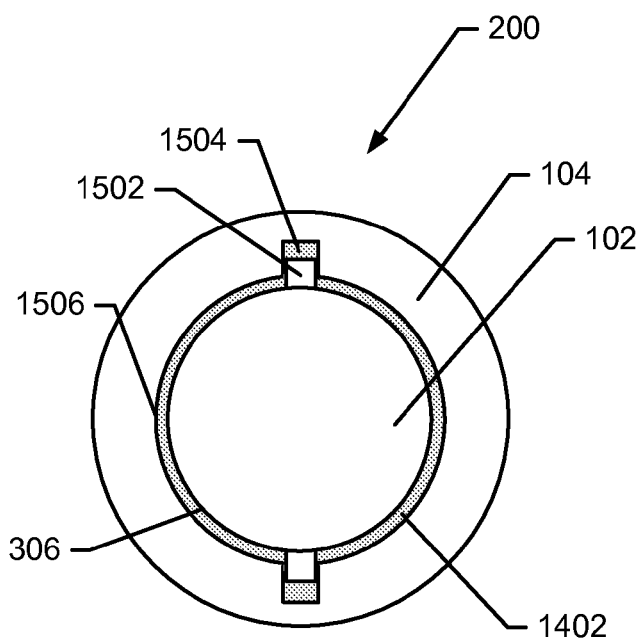
FIG. 15 is a transverse cross-sectional view of a circular cross-sectioned implant body fitted within a circular cross-sectioned lumen of an implant outer layer.

In another aspect, the implant body 102 and implant outer layer 104 may have matching cross-sectional shapes including circular cross-sectional shapes, as illustrated in the transverse cross-sectional view of FIG. 15. In this aspect, the alignment feature may be provided in the form of at least one longitudinal ridge 1502 projecting outward from the body external surface 306 that may be situated within a corresponding groove 1504 formed within a lumen wall 1506 that defines the lumen 1402 of the implant outer layer 104.

Figure 16:
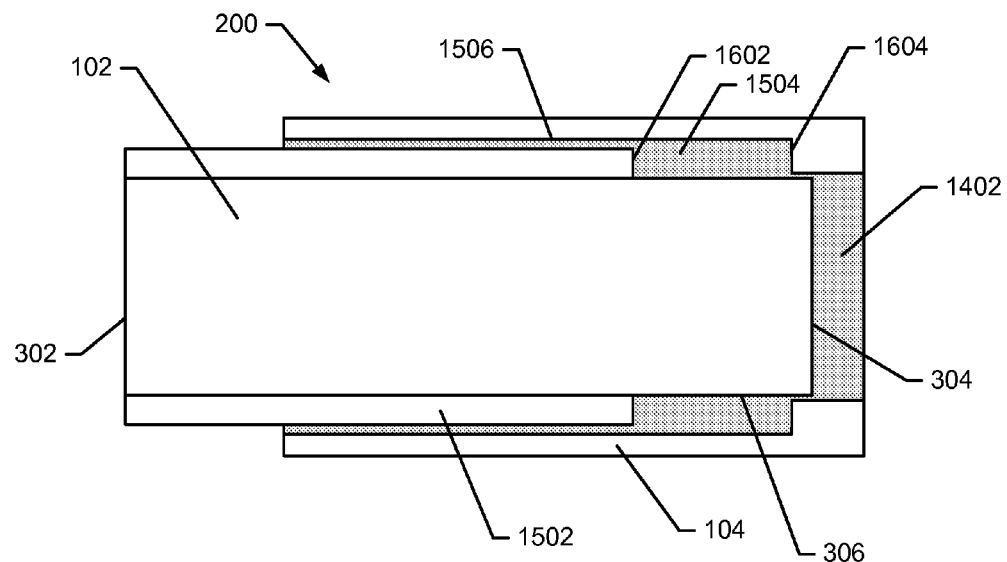
FIG. 16 is a longitudinal cross-sectional view of a circular cross-sectioned implant body fitted within a circular cross-sectioned lumen of an implant outer layer.

A longitudinal cross-section of the implant assembly 200 of FIG. 15 is illustrated in FIG. 16. During the insertion of the implant body 102 within the lumen 1402 of the implant outer layer 104, each longitudinal ridge 1502 may slide within a corresponding groove 1504, ensuring proper alignment of the implant body 102 within the implant outer layer 104. Each longitudinal ridge 1502 and corresponding groove 1504 may extend the entire length of the implant body 102 and outer layer 104, respectively, or each longitudinal ridge 1502 and corresponding groove 1504 may extend only a partial length of the implant outer layer 104, as illustrated in FIG. 16.

Referring again to FIG. 16, each longitudinal ridge 1502 may end in a distal face 1602 and each corresponding groove 1504 may end in a distal stop 1604. In another aspect, illustrated in the longitudinal cross-section of FIG. 17, the distance at which the protruding end 1702 of the implant body 102 extends from the implant outer layer 104 may be limited by the mechanical interference of the distal stop 1604 with the distal face 1602. During the formation of the implant assembly 200, the implant body 102 may be inserted within the lumen 1402 of the implant outer layer 104 until the distal face 1602 contacts the distal stop 1604, preventing further insertion of the implant body 102.

Figure 18:
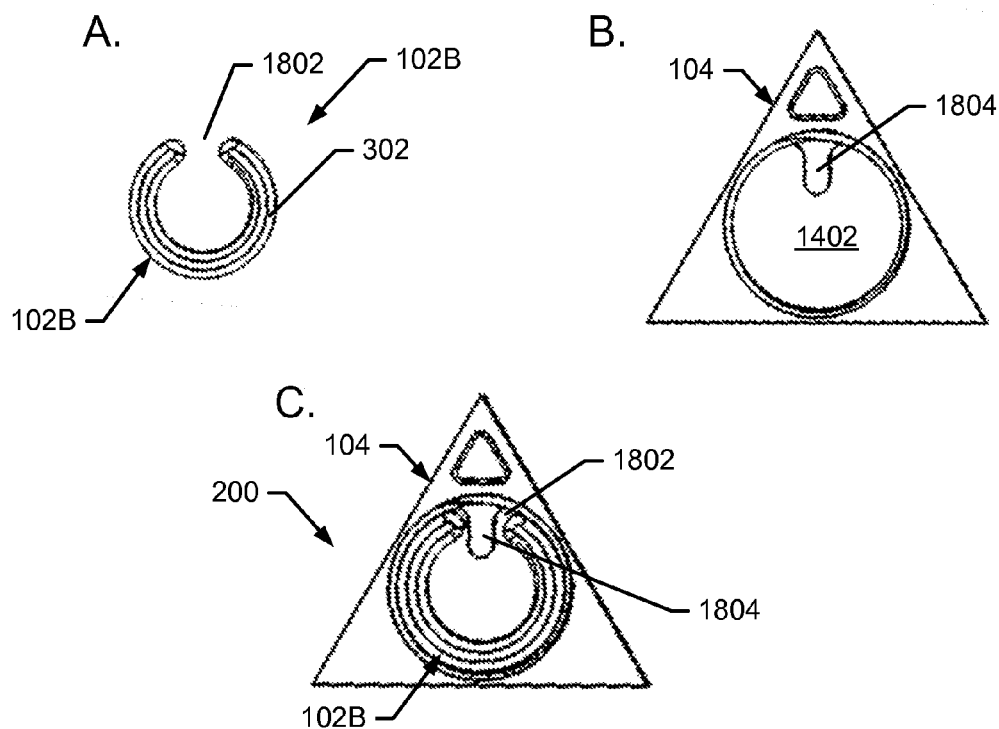
FIG. 18A is a transverse cross-sectional view of a hollow cylindrical implant body with a longitudinal groove.
FIG. 18B is a transverse cross-sectional view of a longitudinal ridge projecting from a lumen of an implant outer layer.
FIG. 18C is a transverse cross-sectional view of an implant body with a longitudinal groove inserted in a lumen with a projecting longitudinal ridge situated within the longitudinal groove.

In another aspect, illustrated in FIG. 18A as a transverse cross-section of the implant body 102B illustrated in FIG. 4, the alignment feature may be provided in the form of a longitudinal groove 1802 formed within the implant body 102B. In this aspect, the longitudinal groove 1802 may fit within a longitudinal ridge 1804 projecting inward toward the lumen 1402 of an implant outer layer 104, as illustrated in the transverse cross-section illustrated in FIG. 18B. When the implant assembly 200 is produced by inserting the implant body 102B into the lumen 1402 as illustrated in the transverse cross-section of FIG. 18C, the meshing of the longitudinal ridge 1804 within the longitudinal groove 1802 maintains the desired alignment of the implant body 102 within the implant outer layer 104.

In an additional aspect (not shown), the alignment feature may be provided in the form of at least one discrete extendable pin projecting from the body external surface 306 of the implant body 102. Each extendable pin may fit within a corresponding pin receptacle formed within the lumen wall 1506 of the implant outer layer 104 when the implant body 102 is situated in a predetermined alignment within the implant outer layer 104. In another additional aspect, the alignment feature may be provided in the form of one or more pin receptacles formed within the body external surface 306 of the implant body 102 that receive corresponding extendable pins projecting inward from the lumen wall 1506 when the implant body 102 is situated in a predetermined alignment within the lumen 1402.

In yet other aspects (not shown), the alignment feature may be provided in the form of circumferential threads formed within the body external surface 306 of the implant body 102. In this aspect, the circumferential threads may extend from the body distal end 304 toward the body proximal end 302 up to the full length of the implant body 102. The circumferential threads may engage mechanically with a circumferential threaded fitting formed within the lumen wall 1506 of the implant outer layer 104. This circumferential threaded fitting may extend from the outer layer proximal end 1902 of the implant outer layer 104 in a distal direction up to the full length of the lumen 1402 of the implant outer layer 104. In this aspect, the length of the circumferential threads and/or circumferential threaded fitting may determine the degree of penetration of the implant body 102 through the lumen 1402 of the implant outer layer 104, thereby controlling the distance at which the implant body 102 projects from the implant outer layer 104.

b. Implant Outer Layer

Figure 19:
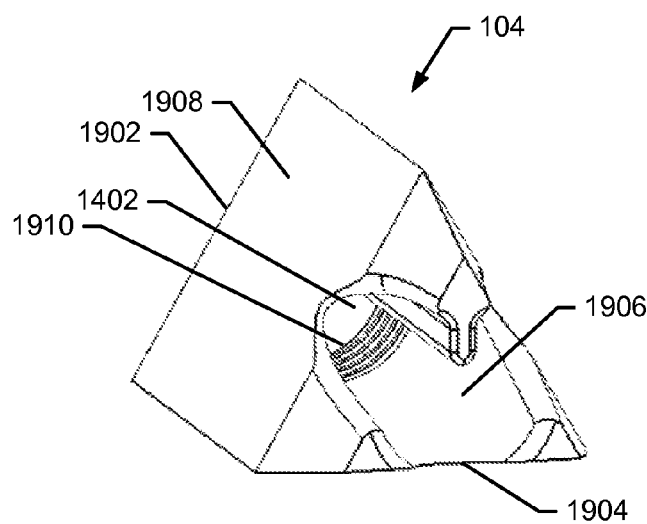
FIG. 19 is a distal perspective view of an implant outer layer with a triangular external cross-sectional profile.

The implant body 102 may be partially or fully contained within an implant outer layer 104 in various aspects. The implant outer layer 104 in one aspect is illustrated in FIG. 19. The implant outer layer 104 may be inserted within a bore (not shown) formed within the afflicted region of the patient to provide a stationary anchor for the implant body 102 and fastener 106 (not shown). The implant outer layer 104 may interact mechanically and/or biologically with the bone tissue within the bore and may provide features that may encourage bone growth, prevent migration and/or loosening of the implant assembly 200 within the bore, and/or otherwise stabilize the position of the implant assembly 200.

In an aspect, the implant outer layer 104 may include an outer layer proximal end 1902 and an outer layer distal end 1904. The implant outer layer 104 further contains a lumen 1402 bounded by a lumen wall 1906; the lumen 1402 extends from the outer layer proximal end 1902 to the outer layer distal end 1904. During the formation of the implant assembly 200, the implant body 102 may be inserted into the lumen 1402. In various aspects, the implant body 102 may be contained completely within the lumen 1402, or the body distal end 304 may protrude from the outer layer distal end 1904. In some aspects, the implant outer layer 104 may include one or more locking elements 310 that may help to secure the fastener 106 in a locked attachment during the formation of the implant assembly 200. In other additional aspects, the implant outer layer 104 may further include an external surface 1908 that contacts the inner surface of the bore formed in the bone tissue of the patient within an afflicted area. In these other additional aspects, the external surface 1908 of the implant outer layer 104 may further include surface textures, surface coatings, holes or pores, and any other surface features known in the art to encourage the incorporation of bone tissue; these surface features may inhibit the movement or loosening of the implant assembly 200 within the bore over extended post-implantation periods.

In one aspect, the implant outer layer 104 may be machined, molded, formed, or otherwise manufactured from stainless steel, titanium, ceramic, polymer, composite, bone or other biocompatible materials.

i. Outer Layer External and Cross-sectional Shape

The implant outer layer 104 may have a variety of cross-sectional shapes in various aspects. The cross-sectional shape of the implant outer layer 104 may facilitate the anchoring of the implant outer layer 104 within the bore, may provide one or more locking elements 310 to secure the attachment fitting of the fastener 106, and/or may provide one or more corresponding alignment features to ensure the proper alignment and/or insertion depth of the implant body 102 within the lumen 1402.

The implant outer layer 104 may have a variety of external shapes and cross-sectional profiles without limitation, depending upon the desired properties and uses of the implant outer layer 104. For example, different shapes, sizes, and/or cross-sectional profiles of the implant outer layer 104 may be selected to accommodate various orthopedic surgical areas and/or procedures, patient morphologies, shapes and types of implant bodies 102, shapes and types of fasteners 106, and/or any other suitable criterion.

The implant outer layer 104 may be provided as any external shape without limitation, so long as the implant outer layer 104 is capable of performing all aspects of the outer layer's function. In one aspect, the external cross-sectional profile of the implant outer layer 104 may be selected to fit within the bore formed within the afflicted area of the patient. In this aspect, the external cross-sectional profile may be selected to match a cross-sectional profile of a bore formed using known orthopedic surgical techniques. For example, the external cross-sectional profile of the implant outer layer 104 may be circular to match a bore created by a drill-type surgical bone removal device. In other aspects, the external cross-sectional profile of the implant outer layer 104 may be a non-circular profile to enhance the stability of the outer layer within the bore; for example an implant outer layer 104 with a triangular external cross-sectional profile, as illustrated in FIG. 19, may impart a resistance to twisting within the bore during subsequent use. Non-limiting examples of non-circular cross-sectional profiles include elliptical, semi-circular, rectangular, triangular, any other polygonal geometry, and any other non-circular geometry.

Referring again to FIG. 19, the cross-sectional profile of the implant outer layer 104 includes the lumen 1402 for receiving the implant body 102 in various aspects. The cross-sectional profile of the lumen wall 1906 that forms the lumen 1402 may be selected independently of the external cross-sectional profile of the implant outer layer 104. The cross-sectional profile of the lumen wall 1906 may be selected to match the cross-sectional profile of the implant body 102. In an aspect, the cross-sectional profile of the lumen wall 1906 may be relatively constant along the length of the implant outer layer 104 to facilitate the insertion of the implant body 102 during the formation of the implant assembly 200. In another aspect (not shown), the cross-sectional profile of the lumen wall 1906 may be wider at the outer layer proximal end 1902 and narrower at the outer layer distal end 1904. In this aspect, the narrower cross-sectional profile at the outer layer distal end 1904 may limit the degree of insertion of the implant body 102 to a predetermined distance in the implant assembly 200.

In another aspect, the lumen wall 1906 may include at least one alignment feature to ensure that the implant body 102 is contained within the implant outer layer 104 at a predetermined orientation and/or insertion distance. In this aspect, the alignment features included in the lumen wall 1906 may be selected to be compatible with the corresponding alignment features included on the body external surface 306 of the implant body 102. Non-limiting examples of suitable alignment features included in or on the lumen wall 1906 include longitudinal ridges, longitudinal grooves, extendable pins, pin receptacles, threaded receptacles, and any other suitable alignment feature known in the art. For example, the lumen wall 1906 may include a longitudinal ridge 1804, illustrated in FIG. 19, which may be situated within the longitudinal groove 404 of the implant body 102B when the implant body 102 is inserted and/or contained within the implant outer layer 104 to maintain the desired alignment.

ii. Tool Fitting

In an aspect, the implant outer layer 104 may include a tool fitting for releasably connecting an end of the retaining rod 110 to the outer layer proximal end 402 of the implant outer layer 104. The tool fitting may include, but is not limited to a threaded fitting 1910, a hexagonal connection, or indentations 2002A-2002D for interlocking with corresponding tines 2004A-2004D on the retaining rod 110. The implant outer layer 104 may connect with the retaining rod 110 to accurately situate the implant outer layer 104 within the bore formed at the surgical site and to fix the implant outer layer 104 in place while the fastener 106 is implanted.

Figure 20:
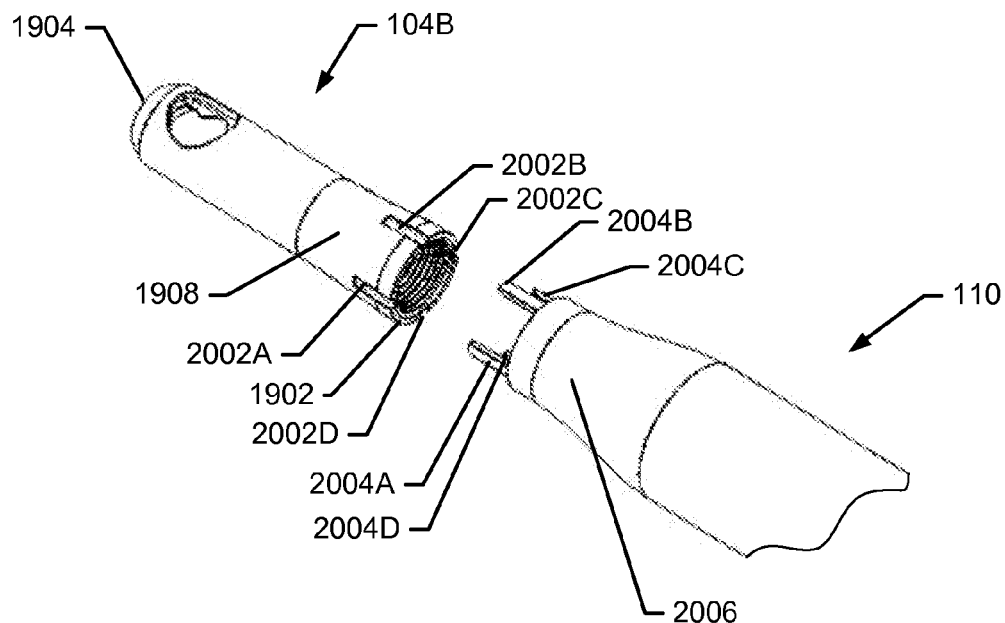
FIG. 20 is an exploded perspective view of a tool fitting with indentations and a corresponding end of a retaining rod.
Figure 21:
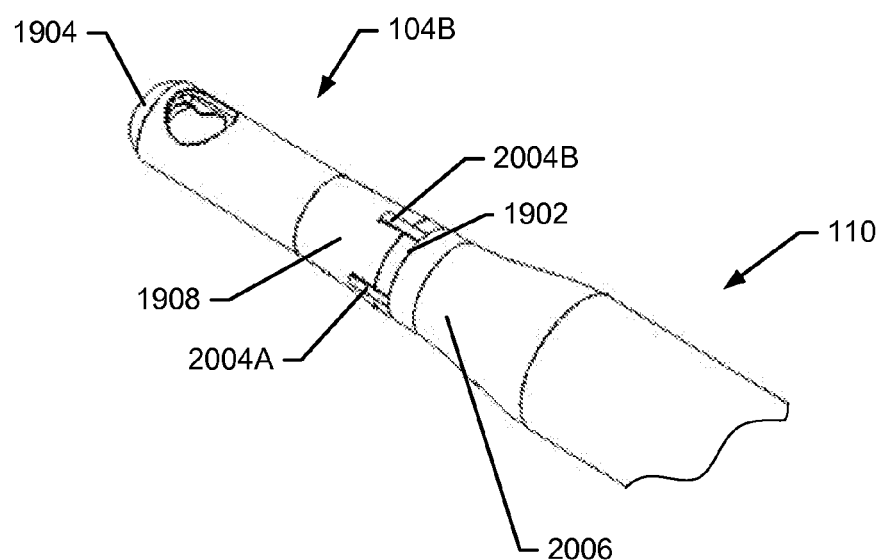
FIG. 21 is a proximal perspective view of an implant body and end of a retaining rod in an interlocked arrangement.

For example, the outer layer may include a tool fitting in the form of a threaded fitting 1910, as illustrated in FIG. 19. In another example, illustrated as a perspective view in FIG. 20, the implant outer layer 104B may include a tool fitting in the form of indentations 2002A-2002D formed within the external surface 1908 of the implant outer layer 104B to reversibly attach to the end 2006 of the retaining rod 110 during formation of the implant assembly 200. In this aspect, the indentations 2002A-2002D may be situated and dimensioned to engage corresponding tines 2004A-2004D projecting from the end 2006 of the retaining rod 110 in a reversibly interlocked arrangement. FIG. 21 is a perspective view illustrating the implant body 102 and the end 2006 of the retaining rod 110 in the interlocked arrangement.

iii. Fastener Opening or Fitting

Referring back to FIG. 2, the implant outer layer 104 may be open at both the proximal and distal ends. In this aspect, the distal end of the implant body 102 may project from the implant outer layer 104, exposing the locking element 310 formed within the implant body 102. The fastener 106 may attach directly to the exposed locking element 310 within the implant body 102 without mechanical interference from the implant outer layer 104.

Figure 22:
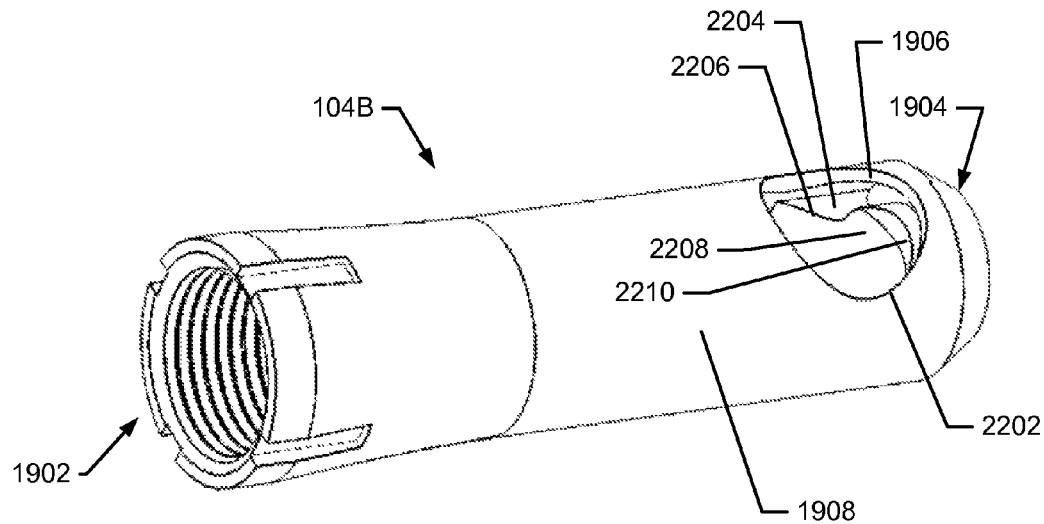
FIG. 22 is a proximal perspective view of an implant outer layer showing a fastener opening.

FIG. 22 is a perspective view of an implant outer layer 104B showing a fastener opening 2202 in another aspect. In this aspect, the lumen 1402 of the outer layer 104B is closed at the outer layer distal end 1904. As a result, the implant body 102 (not shown) fits completely within the lumen 1402. The implant outer layer 104B may include a fastener opening 2202 formed through the lumen wall 1906 to provide access to the locking element 310 of the implant body 102. The fastener opening 2202 may be formed near the outer layer distal end 1904 and extend from the external surface 1908 into the lumen 1402. The fastener opening 2202 may be situated in alignment with the corresponding locking elements 310 on the implant body 102 (not shown) to allow the fastener 106 access to the corresponding locking element 310 of the implant body 102 through the implant outer layer 104.

The implant outer layer 104 may further include additional locking elements that mechanically engage with the fastener 106 along with the locking elements 310 formed within the implant body 102 to stabilize and/or immobilize the fastener 106 (not shown) within the implant assembly 200. Referring back to FIG. 22, the implant outer layer 104B may further include additional locking elements in the form of a lock slot 2204 formed within the lumen 1402 of the implant outer layer 104B in an aspect. The lock slot 2204 may define a wider region 2206 for receiving an attachment fitting of a fastener 106 at its widest diameter, as well as a narrower region 2208 to securely contain a narrower region of an attachment fitting of the fastener 106 in cooperation with the locking elements 310 of the implant body 102. The additional locking elements may further include contoured surfaces, such as a curved face 2210 illustrated in FIG. 22 at the distal end of the lumen 1402. In an aspect, the curved face 2210 may be shaped to correspond with the curvature of an attachment fitting 2810 of the fastener 106 to enhance the locked engagement formed between the attachment fitting 2810 of the fastener 106, the locking element(s) 310 of the implant body 102, and the additional locking element(s) of the implant outer layer 104. A detailed description of the locked engagement of the fastener 106 within the implant outer layer 104 and/or the implant body 102 is provided herein below.

In other aspects, the fastener opening 2202 may include additional locking elements in additional forms including, but not limited to: threaded fittings, self-locking retaining rings, and divoted fittings similar to those described herein above in association with the locking element of the implant body 102.

Figure 23:
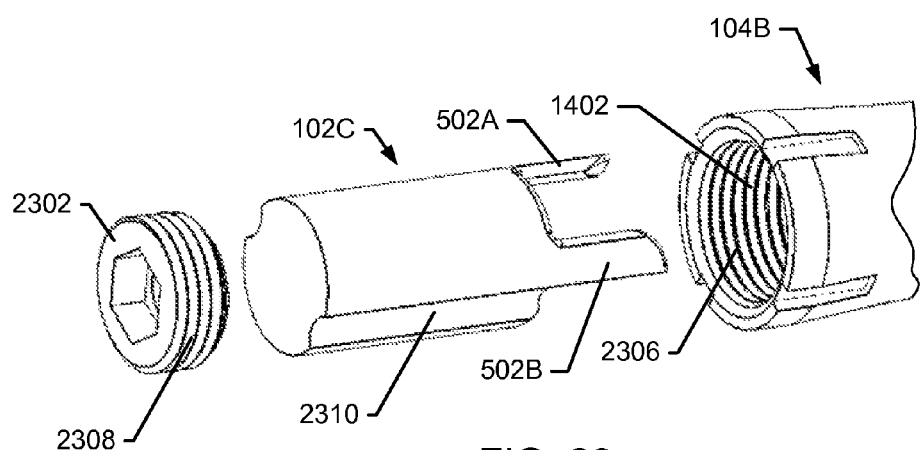
FIG. 23 is an exploded perspective view of an implant outer layer with a fastener opening and a solid implant body.

The implant outer layer 104 may further include a mechanism to lock the implant outer layer 104 to the implant body 102. FIG. 23 is an exploded view illustrating the implant outer layer 104B illustrated previously in FIG. 22, as well as the implant body 102C previously illustrated in FIG. 5. In this aspect, the implant body 102C may be inserted into the lumen 1402 of the implant outer layer 104B, followed by a threaded plug 2302. The threaded plug 2302 includes circumferential threads 2308 that mesh with the threads of a threaded receptacle 2306 within the implant outer layer 104B. The threaded plug 2302 may be advanced within the threaded receptacle 2306 thereby pushing the implant body 102C further within the lumen 1402 ahead of the threaded plug 2302. The advancement of the threaded plug 2302 may be limited by the contact of the longitudinal projections 502A and 502B of the implant body 102C with the closed distal end of the lumen 1402. In this assembled configuration, illustrated as a perspective view in FIG. 24, the implant body 102C may be mechanically locked into place between the closed distal end of the lumen 1402 and the threaded plug 2302.

iv. Alignment Features

Figure 14:
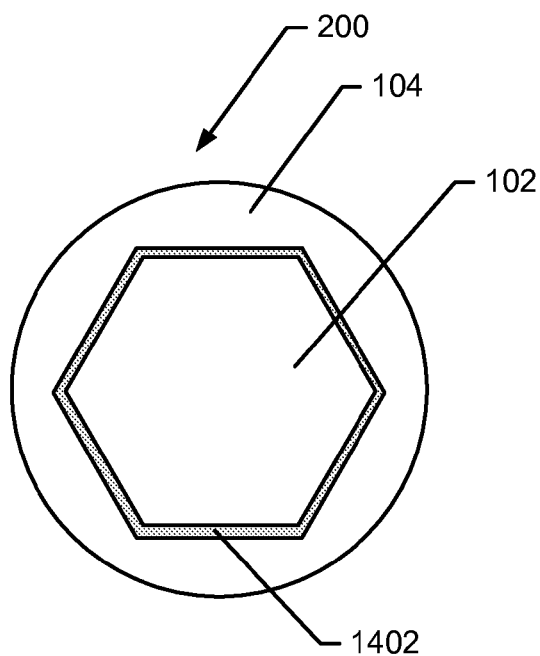
FIG. 14 is a transverse cross-sectional view of a non-circular cross-sectioned implant body fitted within a non-circular cross-sectioned lumen of an implant outer layer.
Figure 17:
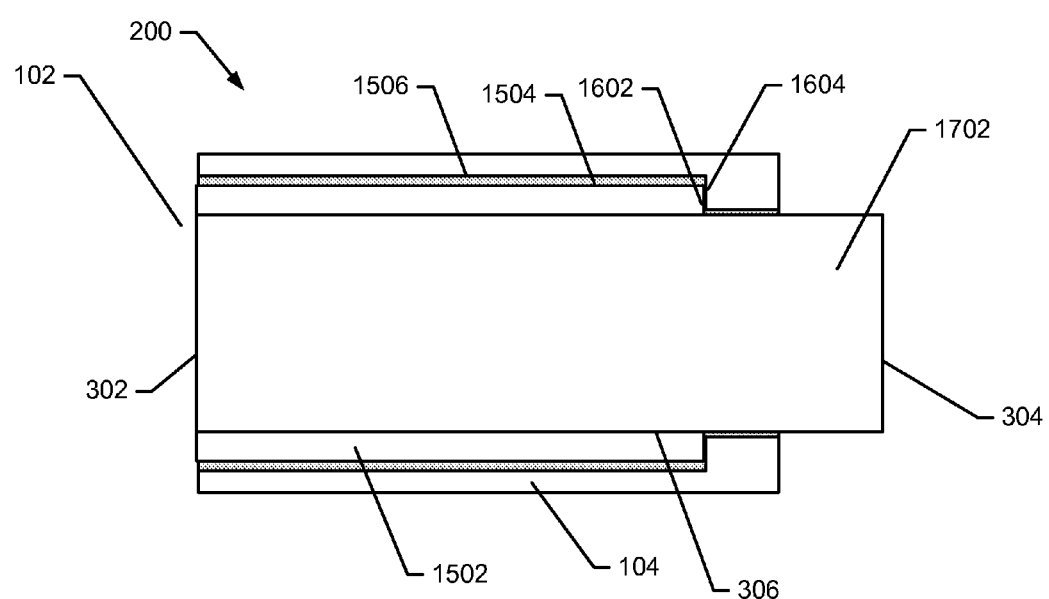
FIG. 17 is a longitudinal cross-sectional view of a protruding end of an implant body limited by a distal stop formed within an implant outer layer.

The implant outer layer 104 may have features on the inner surface 1506 of the lumen 1402 for interacting with corresponding features on the body external surface 306 of the implant body 102, as described previously herein above in association with the description of the alignment features of the implant body 102. In one aspect, the cross-sectional contour of the lumen 1402 may be a non-circular polygon, ellipsoid or any other shape dimensioned to closely fit a correspondingly-contoured implant body 102, as illustrated in FIG. 14. In another aspect, the inner surface 1506 of the lumen 1402 may include ridges or grooves 1504 to interlock with corresponding grooves or ridges 1502 on the body external surface 306 of the implant body 102, as illustrated in FIGS. 15-17. In an additional aspect, the implant outer layer 104 include retractable pins and/or pin receptacles that mechanically interlock with corresponding pin receptacles and/or retractable pins formed or attached to the body external surface 306 of the implant body 102. In yet another aspect, the implant outer layer 104 may further include features such as circumferential threads or threaded receptacles that mechanically intermesh with corresponding threaded receptacles or circumferential threads included in the implant body 102.

v. External Surface Texture

The implant outer layer 104 may further include surface features and/or textures on the external surface 1908. This exposed external surface 1908 may interact with the bone tissue mechanically and/or biologically and may include anti-migration surface features. These anti-migration surface features may assist in preventing the implant assembly 200 from moving or migrating within the afflicted area during prolonged use by the patient.

The implant outer layer 104 may include an anti-migration texture projecting outward from the external surface 1908 and/or other anti-migration surface features. Non-limiting examples of anti-migration surface features include a plurality of projections, a plurality of serrated teeth or ridges, a plurality of perforations, or any other surface feature on the external surface 1908 which may reduce the migration of the implant body 102 and/or implant outer layer 104. The surface features may be unidirectional in an aspect.

In various aspects, the external surface 1908 of the implant outer layer 104 may have a plurality of projections as an anti-migration texture. The plurality of projections may extend to a projection height ranging from about 0.2 mm to about 5 mm from the surface. The plurality of projections may be distributed essentially uniformly over the external surface 1908. The plurality of projections may project essentially perpendicularly from the external surface 1908.

Figure 25:
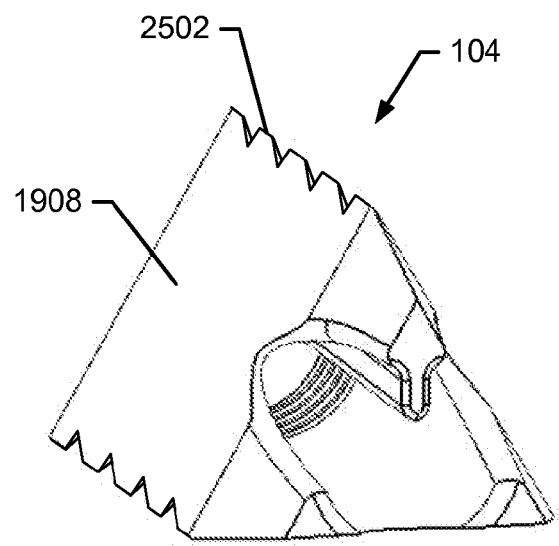
FIG. 25 is a proximal perspective view of an implant outer layer with anti-migration serrated edges.
Figure 26:
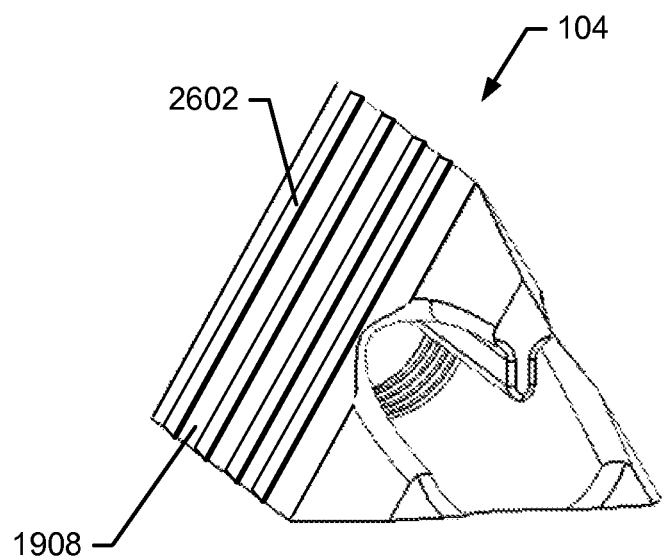
FIG. 26 is a proximal perspective view of an implant outer layer with anti-migration wedge-shaped ridges.

In another aspect, the external surface 1908 may have a plurality of unidirectional serrated teeth or ridges. Each serrated tooth or ridge may include a right triangular cross-section with a base, a side, and an apex. The base of each serrated tooth or ridge may extend perpendicularly from the external surface 1908 to a height ranging from about 0.2 mm to about 5 mm. The side of each serrated tooth or ridge may be coincident with the external surface 1908. The apex of each serrated tooth or ridge may be situated nearer to the outer layer distal end 1904 relative to the base. FIG. 25 is a perspective view of an implant outer layer 104 that includes an anti-migration texture in the form of serrated edges 2502 in one aspect. FIG. 26 is a perspective view of an implant outer layer 104 that includes an anti-migration texture in the form of wedge-shaped ridges 2602 on the external surface 1908 in another aspect.

Figure 27:
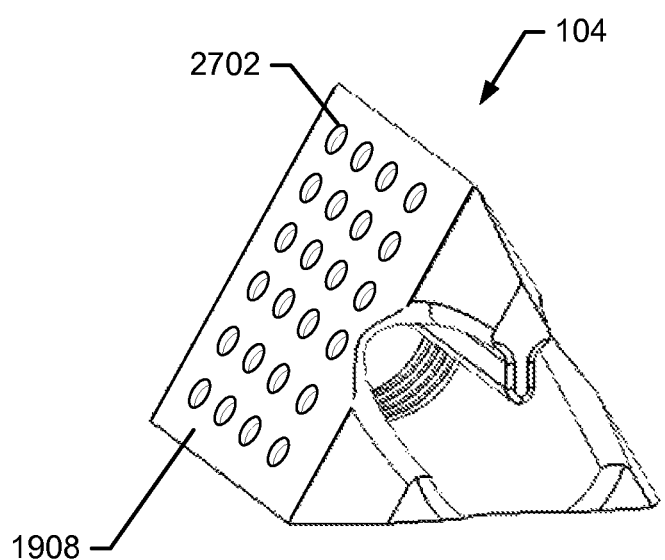
FIG. 27 is a proximal perspective view of an implant outer layer with a plurality of perforations.

The external surface 1908 of the implant outer layer 104 may have a plurality of perforations 2702 that may extend from the external surface 1908 into the lumen 1402. FIG. 27 is a perspective view of an implant outer layer 104 that includes a plurality of perforations 2702 in the external surface 1908 in an aspect. The plurality of perforations 2702 may provide spaces for the incorporation of bone tissue. The plurality of perforations 2702 may be distributed essentially uniformly over the external surface 1908, as illustrated in FIG. 27, or the plurality of perforations 2702 may be distributed in a non-uniform pattern in another aspect. In this other aspect, the plurality of perforations 2702 may be spaced in a closer distribution in close proximity to edges of the outer layer such as the outer layer proximal end 1902, outer layer distal end 1904, or in any other suitable pattern known in the art. The plurality of perforations 2702 may further include a compound suitable for inducing or enhancing a variety of effects to reinforce the fixation of the implant outer layer 104 and associated implant assembly 200 within the bore. Non-limiting examples of suitable effects for reinforcing the fixation of the anchor assembly within the bore include: stimulating the incorporation of bone tissue into the perforations 2702, enhancing the biocompatibility of the implant assembly, enhancing the bonding of the external surface 1908 to the surrounding bone tissue of the bore, and any combination thereof. Non-limiting examples of suitable compounds to include within the plurality of perforations 2702 include: a bone growth factor, a nutrient, bone tissue transplant cells, bone stem cells, anti-rejection compounds, biocompatible bone cement, and/or any other suitable compound in any combination.

In one aspect, the external surface 1908 of the implant outer layer 104 may be treated with a bone growth factor or other compounds to encourage bone tissue growth around the implant assembly 200. In another aspect, the lumen 1402 may be filled with a bone paste material. In this aspect, the bone paste material may be pressed out through the plurality of perforations 2702 when the implant body 102 is inserted into the lumen 1402 during the formation of the implant assembly 200; the bone paste material pressed out of the lumen 1402 may be situated within any voids between the bore and the external surface 1908 of the implant outer layer 104.

c. Fastener

In various aspects, the implant assembly 200 of the orthopedic anchoring system 100 may include an fastener 106 attached at one end to the implant outer layer 104 and/or implant body 102. The fastener 106 may attach in a locked engagement to the implant outer layer 104 and/or implant body 102 at one or more locking elements, forming a robust anchor for an orthopedic procedure, orthopedic device or appliance, or any other related treatment of an afflicted region of a patient.

Figure 28:
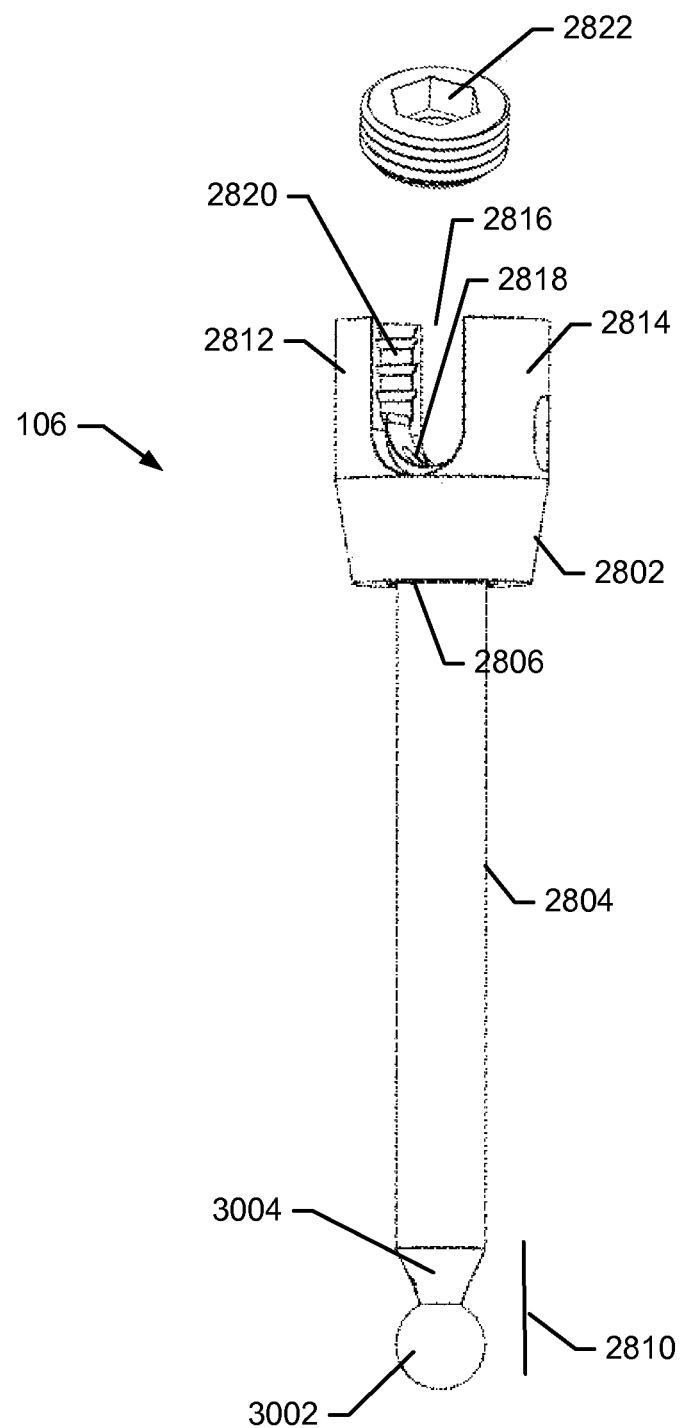
FIG. 28 is an exploded side view of a fastener and threaded compression nut.

FIG. 28 is a side view of a fastener 106 in one aspect. The fastener may include a head 2802, a shaft 2804 including a top end 2806, and an attachment fitting 2810 opposite to the top end 2806. In an aspect, the attachment fitting 2810 may include an end 3002 and a neck 3004. The attachment fitting 2810 may mechanically attach to a corresponding locking element 310 of an implant body 102 and/or a locking element of an implant outer layer 104.

The fastener 106 may be any surgical fastener type suitable for and/or compatible with various orthopedic interventions and treatments known in the art. Non-limiting examples of suitable surgical fasteners include nails, pins, screws, pegs, staples, and any other known surgical fastener type. In one aspect, the fastener 106 may be an orthopedic pedicle screw with a tulip-like head suitable for a variety of orthopedic procedures either in isolation or in combination with other orthopedic devices, appliances, and/or implants including, but not limited to, reinforcing rods, reinforcing wires, reinforcing plates, and any other reinforcing structural element.

In one aspect, the fastener 106 may be machined, molded, formed, or otherwise manufactured from stainless steel, titanium, ceramic, polymer, composite, bone or other biocompatible materials. The material of the fastener 106 may be compatible for continuous contact with the implant body 102 and implant outer layer 104.

i. Head

In one aspect, the fastener 106 may include a head 2802. The head 2802 may be provided in any form known in the art. The particular form of the head 2802 may be selected to be compatible with the orthopedic device or appliance to be implanted within the afflicted region of the patient as part of an orthopedic surgical procedure. Referring back to FIG. 28, the head 2802 may be provided in the form of a tulip-like head in one aspect. In this aspect, the head 2802 may include at least two support elements 2812 and 2814 forming the sides of at least one upward-opening groove 2816. The head 2802 may further include a compression element 2818 forming the bottom surface of the groove 2816. The inner surfaces of the at least two support elements 2812 and 2814 may further form a threaded fitting 2820 into which a threaded compression nut 2822 may be inserted during use.

In this aspect, the head 2802 may be attached to the top end 2806 of the shaft 2804 such that the head 2802 may rotate freely about a longitudinal axis of the shaft 2804, but may not otherwise translate or rotate. In use, an elongate reinforcing element such as a rod (not shown) may be situated within the groove 2816. The compression nut 2822 may be situated within the threaded fitting 2820 and advanced until the reinforcing element is held fixed between the compression nut 2822 and the compression element 2818. In another aspect, the introduction of a compressive force onto the compression element 2818 by the compression nut 2822 via the reinforcement element may further introduce a holding force within the attachment of the head 2802 to the top end 2806 of the shaft 2804 such that the head 2802 may no longer rotate freely.

Figure 29:
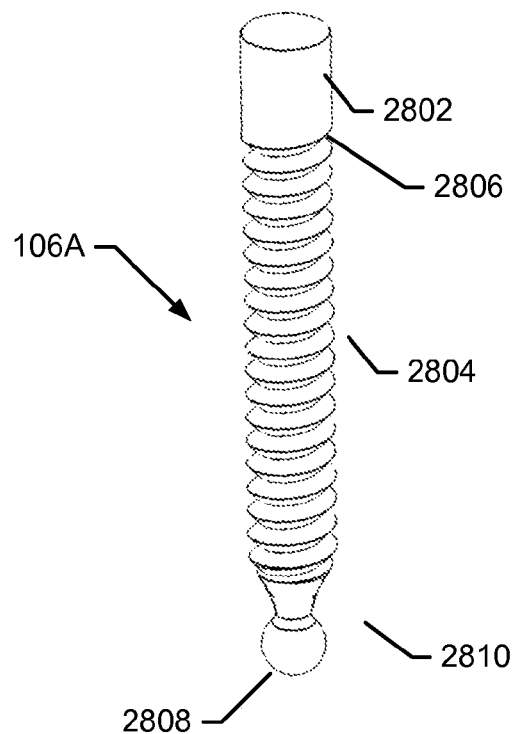
FIG. 29 is a side view of a fastener with a peg-like head.

FIG. 29 is a side view of a fastener 106A in another aspect. In this aspect, the head 2802 of the fastener 106A may be a peg-like head. In this aspect, the head 2802 may be in the form of a cylinder attached in a fixed engagement to the top end 2806 of the shaft 2804. In other aspects, the peg-like head may be modified with raised circumferential rings, circumferential depressions (not shown), radial bores, or any other fitting suitable for forming an interlocked mechanical engagement with a corresponding element of an orthopedic device or appliance.

ii. Shaft

Referring back to FIG. 28, the shaft 2804 of the fastener 106 includes the top end 2806 attached to the head 2802 and the tip 2808 with associated attachment fitting 2810. The shaft 2804 may be unthreaded, as illustrated in FIG. 28, or the shaft may be threaded, as illustrated in FIG. 29. The shaft 2804 may have a transverse cross-sectional profile that is any known profile, including, but not limited to, circular as illustrated in FIG. 28, semicircular, elliptical, polygonal including triangular, square, rectangular, and hexagonal.

In an aspect, the fastener 106 may be any suitable length for use in an orthopedic surgical procedure. The length of the fastener 106 may be selected based at least one of several factors including, but not limited to the individual patient's morphology, the particular type of surgical procedure in which the fastener is to be used, the anatomical location in which the fastener 106 is to be used, the desired strength or rigidity of the fastener, and any other related selection factor known in the art.

When attached to the implant outer layer 104 and/or implant body 102, the shaft 2804 may extend away from the implant body 102 at any angle ranging from about 0° to about 20° relative to a plane perpendicular to the central axis 308. The angle or range of angles at which the shaft 2804 extends away from the implant body 102 may be selected based on the desired surgical use of the fastener 106. In one aspect, the shaft 2804 may extend away from the implant body 102 at a relatively fixed angle within the range described herein previously. In another aspect, the shaft 2804 may extend away from the implant body at an angle that varies freely within any angular sub-range within the range described herein previously.

iii. Tip with Attachment Fitting

In various aspects, the fastener 106 includes an attachment fitting 2810 situated near the tip 2808 for mechanically attaching the fastener 106 to the implant locking element(s) of the implant outer layer 104 and/or implant body 102. The attachment fitting 2810 may form a locked engagement with one or more locking elements within the implant body 102 and implant outer layer 104. In an aspect, the attachment fitting 2810 is provided in a form that is compatible and/or capable of forming a locked engagement with the locking elements of the implant outer layer 104 and/or implant body 102. The attachment fitting 2810 may allow the fastener 106 to lock into place in a fixed engagement or an engagement with limited movement once attached to the implant outer layer 104 and/or implant body 102.

The attachment fitting 2810 may be provided in any known form without limitation, so long as the attachment fitting 2810 is compatible with the locking elements of the implant outer layer 104 and/or implant body 102. Non-limiting examples of suitable attachment fittings include a ball end, a rounded end, and a cone end.

Figure 30:
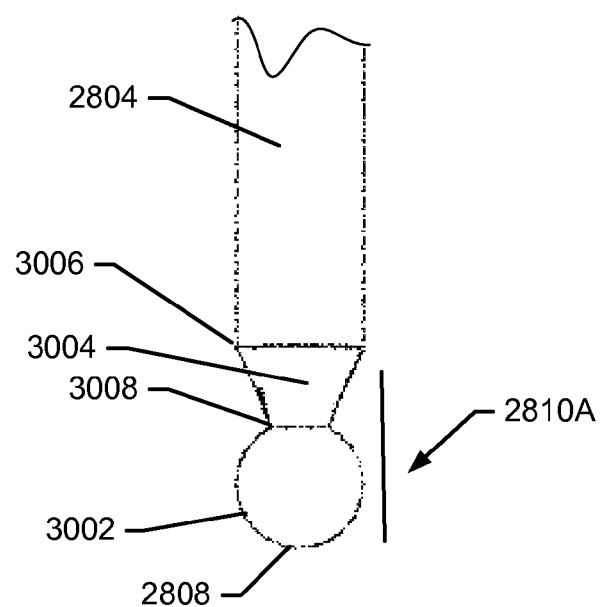
FIG. 30 is a side detail view of a fastener with a ball fitting.

The attachment fitting 2810 may be provided in the form of a ball fitting in one aspect. FIG. 30 is a side view of a ball fitting 2810A. The ball fitting 2810A may include a spherically-shaped end 3002 and a tapered neck 3004 that includes a wide neck end 3006 and opposite narrow neck end 3008. In this aspect, the wide neck end 3006 is attached to the shaft 2804 and the narrow neck end 3008 is attached to the spherically-shaped end 3002. The wide neck end 3006 may have a diameter that is essentially equal to the cross-sectional diameter of the shaft 2804, and the narrow neck end 3008 may have a narrow end diameter that may be at least 10% smaller than the cross-sectional diameter of the shaft 2804. In other aspects, the neck may not be tapered but instead may have a constant diameter at least 10% smaller than the cross-sectional diameter of the shaft 2804. The ball fitting 2810A may be used in combination with any form of shaft 2804 including, but not limited to, a threaded shaft as illustrated in FIG. 28 and an unthreaded shaft as illustrated in FIG. 29.

Figure 31:
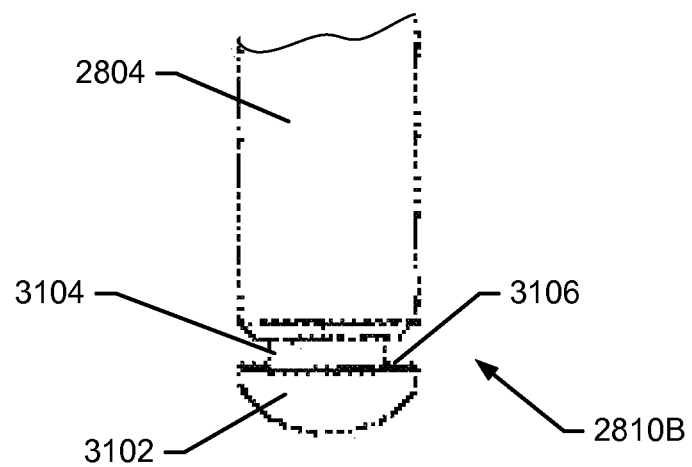
FIG. 31 is a side detail view of a fastener with a rounded fitting.

The attachment fitting 2810 may be a rounded fitting. FIG. 31 is a side view showing a rounded fitting 2810B in one aspect. The rounded fitting 2810B may include a rounded end 3102 and a neck 3104. The neck 3104 may be a narrow cylindrical section attached to the flat face 3106 of the rounded end 3102 and to the shaft 2804 at opposite ends of the neck 3104. The rounded end 3102 may include a spherical section and the flat face 3106. The rounded end 3102 may have a maximum cross-sectional diameter that is essentially equal to the cross-sectional diameter of the shaft 2804. The cross-sectional diameter of the neck 3104 may be at least 10% smaller than the cross-sectional diameter of the shaft 2804.

Figure 32:
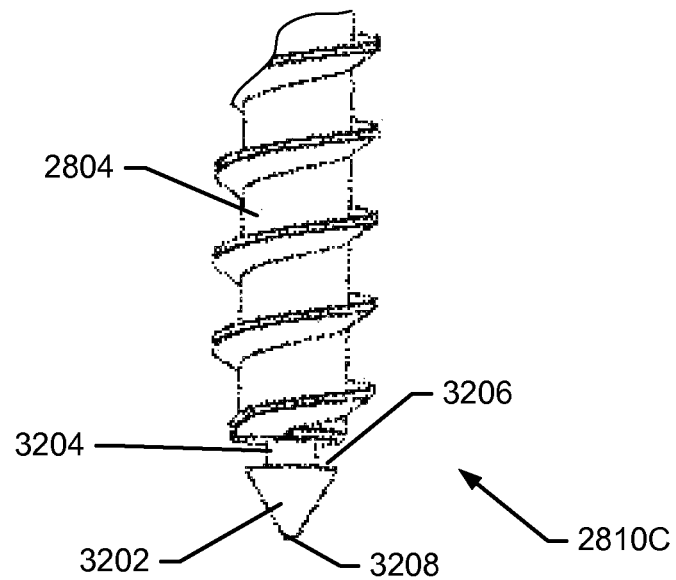
FIG. 32 is a side detail view of a fastener with a cone fitting.

The attachment fitting 2810 may be a cone fitting. FIG. 32 is a side view showing a cone fitting 2810C in one aspect. The cone fitting 2810C may include a conical tip 3202 with a flat face 3206 and a neck 3204. The neck 3204 may be a cylindrical segment attached at one end to the flat face 3206 and attached at the opposite end to the shaft 2804. The cylindrical neck 3204 may have a cross-sectional diameter of at least 10% less than the cross-sectional diameter of the shaft 2804.

Figure 33:
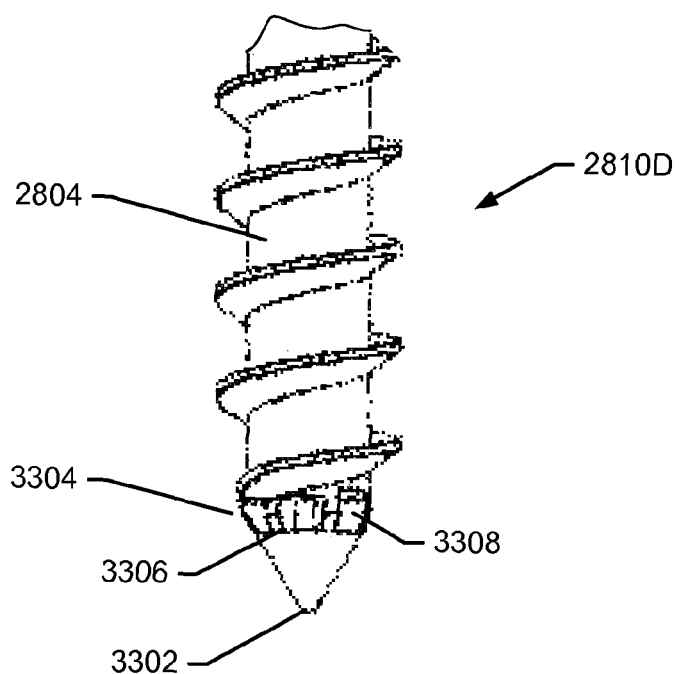
FIG. 33 is a side detail view of a fastener with a divoted fitting.

In another additional aspect, the attachment fitting 2810 may be a divoted fitting. FIG. 33 is a side view showing a divoted fitting 28100 in one aspect. The divoted fitting 28100 may include a conical tip 3302 with a flat face 3306 and a divoted neck 3304. The divoted neck 3304 may be a cylindrical segment attached at one end to the flat face 3306 and attached at the opposite end to the shaft 2804. The cylindrical segment of the divoted neck 3304 may have a cross-sectional diameter that is essentially equal to the cross-sectional diameter of the shaft 2804. From about one to about ten divots 3308 may be formed within the divoted neck 3304. Each divot 3308 may extend from the one end to the opposite end of the divoted neck 3304. The divots 3308 may fit within a divoted locking element (not shown) provided as part of the locking elements on the implant body 102 and/or implant outer layer 104 in an aspect. The divoted locking element may be contoured to mechanically intermesh with the one or more divots 3308 when the fastener 106 is inserted, providing a locked engagement with the divoted fitting 28100.

The attachment fitting 2810 may be provided in any other suitable form without limitation, so long as the attachment fitting 2810 is capable of forming a locked engagement with the one or more locking elements associated with the implant outer layer 104 and/or implant body 102. For example, any attachment fitting 2810 with a non-circular cross-sectional profile, but with an overall tapered profile at the tip 2808 and a reduced-width neck segment similar to the ball fitting 2810A, rounded fitting 2810B, or cone fitting 2810C may be used as an attachment fitting 2810, depending on the particular configuration of the corresponding locking element(s). Non-limiting examples of suitable other attachment fittings include a pyramidal-tipped fitting and a tapered blade-like fitting. In addition, any other attachment fitting profile without limitation may be suitable for use in the fastener 106 so long as the attachment fitting 2810 is capable of forming the locked engagement with the one or more locking elements using any known locking mechanism.

d. Fastener Locking Mechanisms

Any suitable locking mechanism known in the art may be incorporated into the design of the implant assembly 200 without limitation. The locking mechanism may be selected based on any one or more of at least several factors including, but not limited to: the desired orientation of the fastener 106 within the implant assembly 200, the desired degree of allowable movement of the fastener 106 within the implant assembly 200, the ease of attaching the fastener 106 during the formation of the implant assembly 200, and the needed strength of the locked mechanical engagement of the fastener 106 to the implant outer layer 104 and/or implant body 102 within the implant assembly 200.

Figure 34:
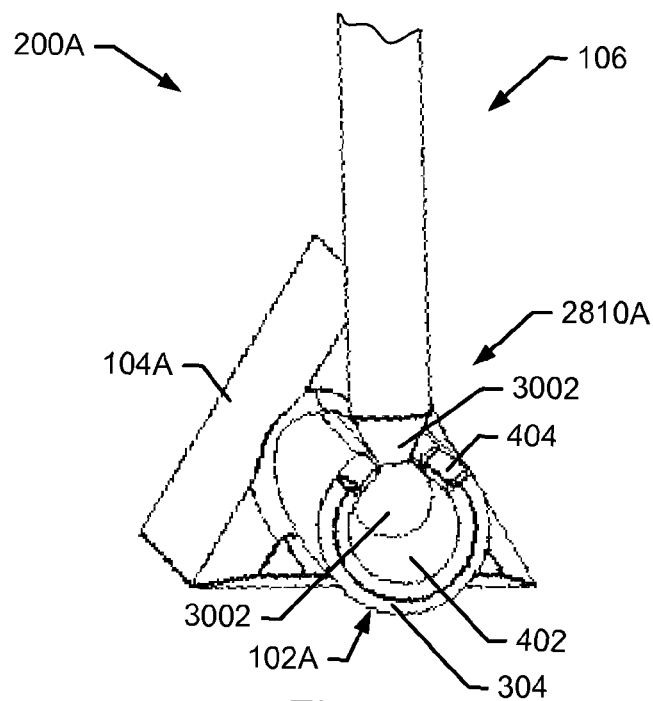
FIG. 34 is a distal perspective view of an implant assembly that includes a slotted implant body and a fastener with a ball fitting, shown assembled to illustrate a locking mechanism.

FIG. 34 is a perspective view of an implant assembly 200A illustrating a locking mechanism in one aspect. The implant assembly 200A in this aspect may include the slotted implant body 102B illustrated previously in FIG. 4, the triangular outer layer 104A illustrated previously in FIG. 19, and the fastener 106 with a ball fitting 2810A illustrated previously in FIG. 30. In this aspect, the fastener 106 and implant outer layer 104A may be implanted into the afflicted region and then the implant body 102A may be inserted such that the longitudinal groove 404 slides over the tapered neck 3004 of the fastener 106. Upon formation of the implant assembly 200A, the spherically-shaped end 3002 may be situated within the body lumen 402 of the implant body 102B, and the tapered neck 3004 may be situated within the longitudinal groove 404. Because the diameter of the spherically-shaped end 3002 is too large to pass through the longitudinal groove 404 and the body distal end 304 of the implant body 102A is butted up against the bottom of the bore formed within the afflicted region of the patient, the fastener 106 is locked into place. In this aspect, the implant outer layer 104A may further limit the movement of the fastener 106 along the length of the implant body 102B.

In this aspect, the rounded profile of the spherically-shaped end 3002 and the relatively open design of the longitudinal groove 404 along the length of the implant body 102B may provide a limited envelope of movement of the fastener 106 within the implant assembly 200 during use. Without being limited to any particular theory, this limited movement may be well-suited for orthopedic surgical applications such as the reinforcement of spinal segments or intervertebral joints that ordinarily undergo limited movements during normal patient activities such as bending or walking. The degree of angular movement of the fastener 106 may be governed by any one or more of at least several factors including, but not limited to: the diameter of the spherically-shaped end 3002 relative to the diameter of the body lumen 402 and/or the width of the longitudinal groove 404, the taper angle of the tapered neck 3004, and various dimensions of the longitudinal groove 404 such as the groove width and the groove depth. The degree of translation of the fastener 106 along the length of the implant body 102B may be governed by any one or more of at least several factors including, but not limited to the distance at which the implant body 102B protrudes from the implant outer layer 104A in the implant assembly 200A. In addition, the fastener 106 may remain free to rotate about the longitudinal axis of the fastener 106 in this aspect.

Figure 35:
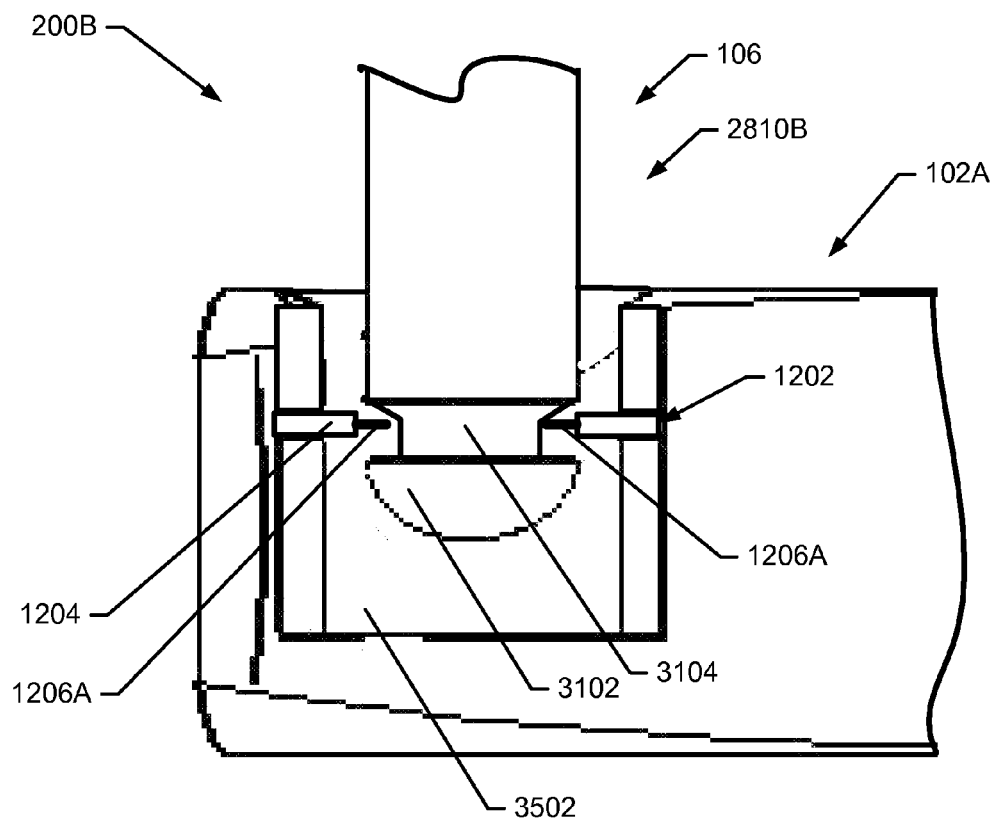
FIG. 35 is a longitudinal cross-sectional view of an implant assembly that includes a solid implant body with a self-locking retaining ring and a fastener with a rounded fitting, shown assembled to illustrate a locking mechanism.

FIG. 35 is a longitudinal cross-sectional view of an implant assembly 200B illustrating a locking mechanism in another aspect. The implant assembly 200B in this aspect may include the solid implant body 102A illustrated previously in FIG. 3 with a self-locking retaining ring 1202, illustrated previously in FIG. 12, and an attached fastener 106 with a rounded fitting 2810B illustrated previously in FIG. 31. In this aspect, the implant outer layer 104 and implant body 102A may be implanted into the afflicted region and the fastener 106 may then be inserted with a force sufficient to penetrate the self-locking retaining ring 1202 with the rounded end 3102. Upon formation of the implant assembly 200B, the rounded end 3102 may be situated within an inner volume 3502 of the implant body 102, and the neck 3104 may be situated between the arcuate members 1206A, 1206B and 1206C (not shown) of the self-locking retaining ring 1202. During insertion of the rounded end 3102 into the self-locking retaining ring 1202, the insertion force reversibly deforms the arcuate members 1206A, 1206B and 1206C downward, resulting in a transient increase in the space between the arcuate members 1206A, 1206B and 1206C to accommodate the insertion of the rounded end 3102. Because the diameter of the rounded end 3102 is too large to pass through the undeflected arcuate members 1206A-1206C without application of a sizeable removal force, the fastener 106 is locked into place. In other aspects, any fastener 106 having a tapered tip and a reduced-diameter neck may be locked into place in this manner including, but not limited to a ball fitting 2810A and a cone fitting 2810C.

In this aspect, the movement of the fastener 106 within the implant assembly 200B may be more restrained relative to the degree of movement afforded by the implant assembly 200A due to the relatively close fit of the self-locking retaining ring 1202 around the neck 3104 of the fastener 106. The degree of movement of the fastener 106 within the implant assembly 200B may be governed by any one or more of at least several factors, including but not limited to: the height and diameter of the neck 3104, the diameter of the opening of the self-locking retaining ring 1202, and the thickness and stiffness of the arcuate members 1206A, 1206B and 1206C. In addition, the fastener 106 may remain free to rotate about the longitudinal axis of the fastener 106 in this aspect.

Figure 36:
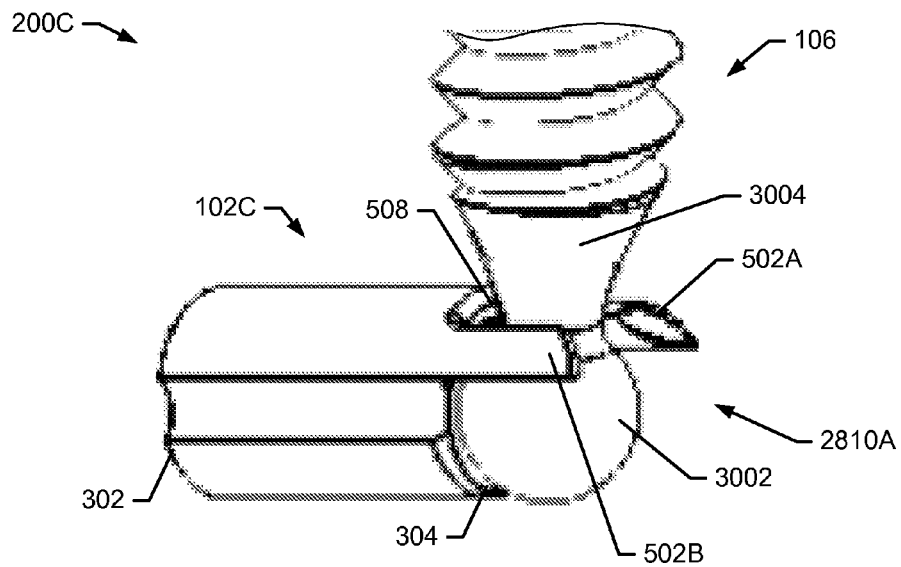
FIG. 36 is a side perspective view of an implant assembly that includes an implant body with longitudinal projections and a fastener with a ball fitting situated within the longitudinal projections.

FIG. 36 is a perspective view of an implant assembly 200C illustrating a locking mechanism in another additional aspect. The implant assembly 200C in this aspect may include the implant body 102C with longitudinal projections 502A and 502B illustrated previously in FIG. 5, the implant outer layer 104B illustrated previously in FIGS. 20-24, and the fastener 106 with a ball fitting 2810A illustrated previously in FIG. 30. The implant outer layer 104 is omitted in FIG. 36 to facilitate visualization of the locking mechanism. In this aspect, the fastener 106 and implant outer layer 104 may be situated within the afflicted area of the patient and then the implant body 102C may be inserted into the implant outer layer 104 as discussed herein previously and illustrated in FIGS. 22-24. The tapered neck 3004 of the fastener 106 may be situated within a slot 508 formed between the pair of longitudinal projections 502A and 502B of the implant body 102C. In addition, the spherically-shaped end 3002 may fit closely within the distal body depression 508 of the implant body 102C.

Figure 24:
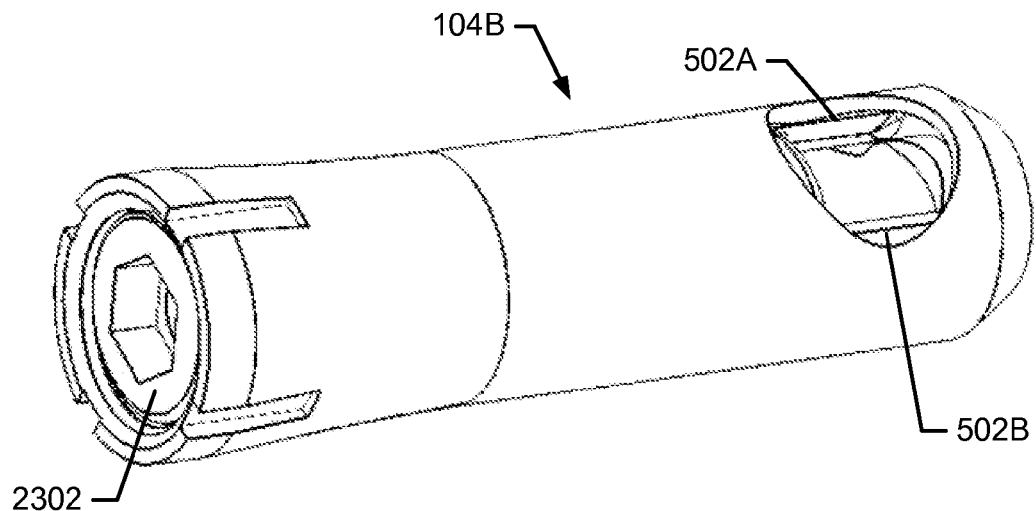
FIG. 24 is a proximal perspective view of an implant body mechanically locked in place within an implant outer layer.
Figure 37:
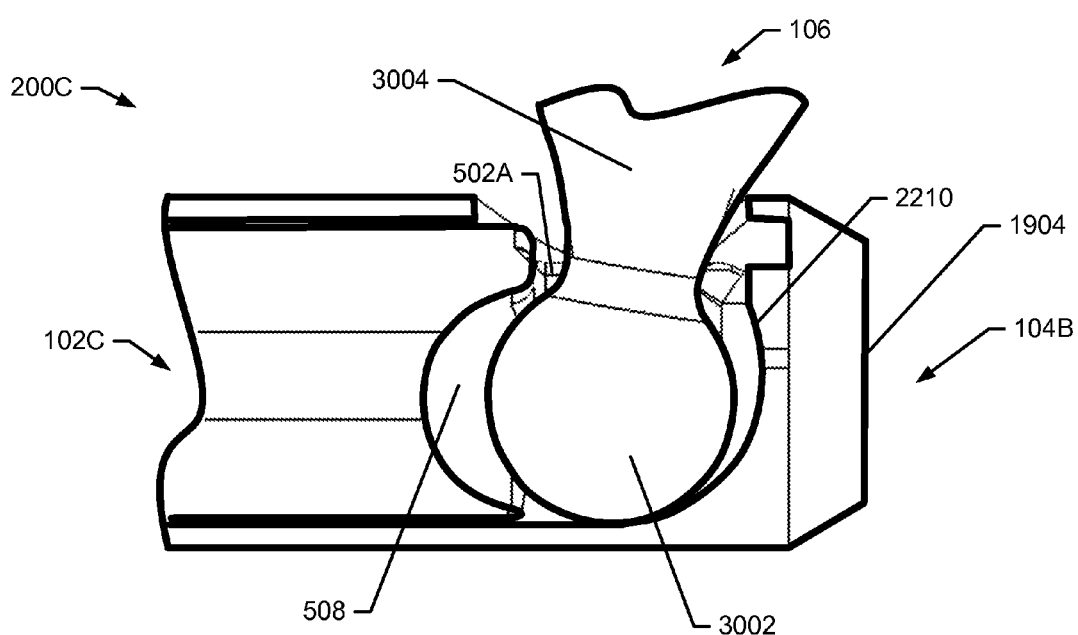
FIG. 37 is a longitudinal cross-sectional view of the implant assembly illustrating the spatial relationships between a ball fitting, an implant body, and an implant outer layer in a locking mechanism.

In this aspect, additional locking elements associated with the implant outer layer 104B may further secure the ball fitting 2810A in place. FIG. 37 is a longitudinal cross-section of the implant assembly 200C illustrating the spatial relationships between the ball fitting 2810A, the implant body 102C, and the implant outer layer 104B. During the formation of the implant assembly 200C, the implant body 102C is inserted within the lumen 1402 of the implant outer layer 104B and shifted toward the outer layer distal end 1904 as illustrated in FIGS. 23-24. When the implant body 102C is fully inserted, the spherically-shaped end 3002 may be compressed between the distal body depression 508 of the implant body 102C and the curved face 2210 of the implant outer layer 104B. As a result, the spherically-shaped end 3002 is secured in a locked configuration within the space formed between the distal body depression 508, the curved face 2210, and the longitudinal projections 502A and 502B.

Prior to compression of the spherically-shaped end 3002 between the distal body depression 508 and the curved face 2210, the fastener 106 may be positioned anywhere within a relatively wide range of movement comparable to the range of movement afforded by the implant assembly 200A described previously. However, the compression of the spherically-shaped end 3002 may render the fastener relatively immobile, even with respect to rotational movements of the fastener 106 about the fastener's longitudinal axis. The tightly locked-in engagement of the fastener 106 in this aspect may be suitable for use in orthopedic surgical treatments in which the efficacy of the treatment may rely upon maintaining a fixed position within the afflicted area.

In another aspect, a fastener 106 with a divoted fitting 28100 may be attached to any implant body that includes a self-locking retaining ring 1202 including, but not limited to implant body 102A illustrated in FIG. 3, implant body 102D illustrated in FIG. 6, and implant body 102E illustrated in FIG. 7. Referring to FIGS. 12 and 33, the one or more divots 3308 may mesh with arcuate members 1206A, 1206B and 1206C, forming a locked engagement. The arcuate members 1206A, 1206B and 1206C may deform to permit insertion of the divoted fitting 28100 into the self-locking retaining ring 1202, but once inserted, the arcuate members 1206A, 1206B and 1206C may mechanically resist the removal of the divoted fitting 28100 from the self-locking retaining ring 1202.

II. Delivery Tool

Referring back to FIG. 1, the orthopedic system 100 may include a delivery tool 300 to implement the preparation of the afflicted region of the patient and the formation of the implant assembly 200. The delivery tool 300 may be designed to perform a variety of surgical procedures associated with the formation of the implant assembly 200 within the afflicted region of the patient. The delivery tool 300 may be used to remove bone or other tissue within the afflicted region of the patient, to form a bore within which the implant outer layer 104 may be inserted, to form a guide hole through which the fastener 106 may be inserted, to obtain visual or other images of the afflicted region, to introduce one or more therapeutic compositions, and any combination thereof.

Figure 38:
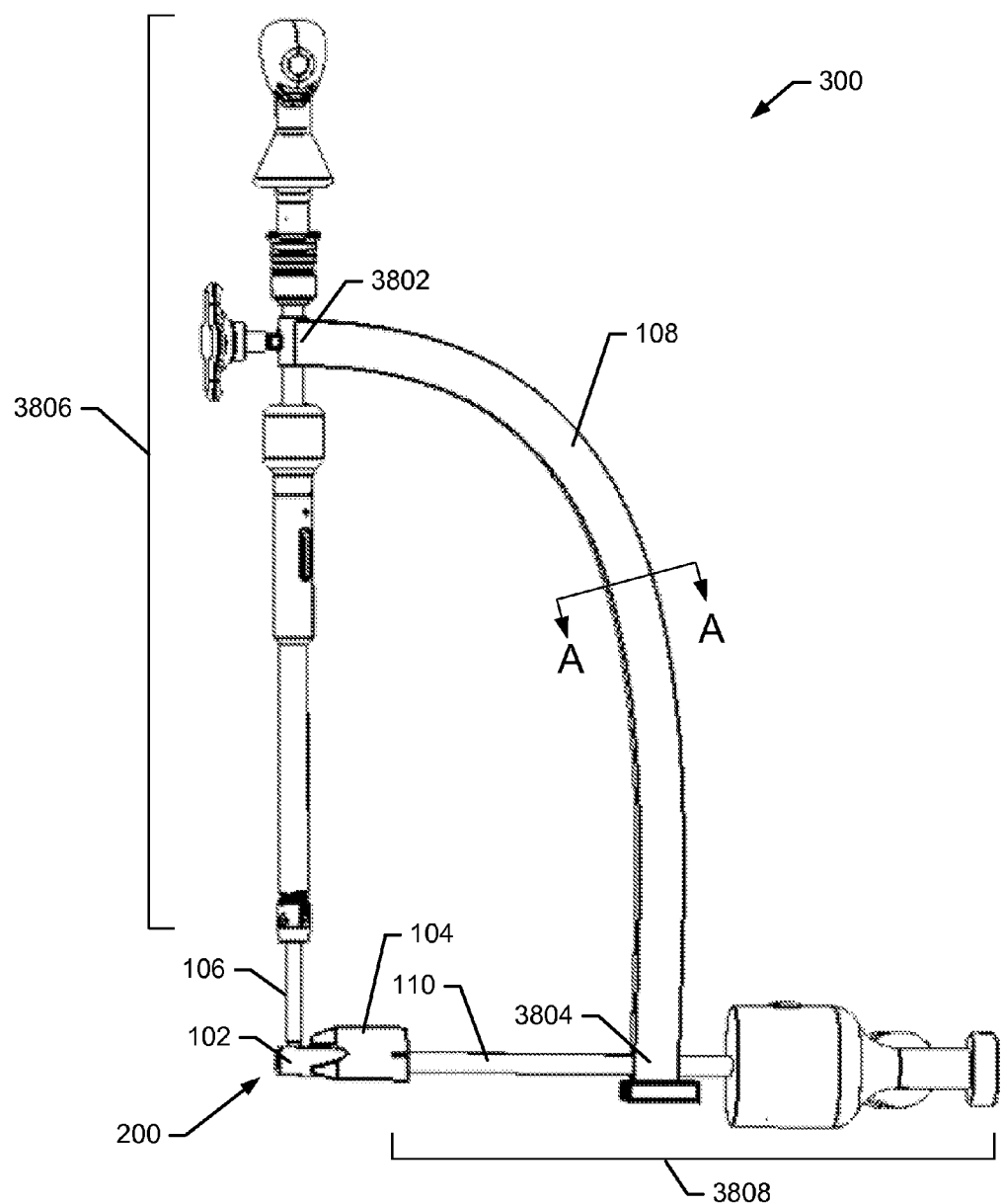
FIG. 38 is a side view of a delivery tool attached to an implant assembly.

FIG. 38 is a side view of the delivery tool 300 attached to an implant assembly 200 in one aspect. The delivery tool 300 may include an elongate targeting arm 108 with a first arm end 3802 and a second arm end 3804 opposite to the first arm end 3802. A fastener guide 3806 may be attached to the targeting arm 108 at the first arm end 3802 and an implant guide 3808 may be attached at the second arm end 3804. The targeting arm 108 maintains the fastener guide 3806 and the implant guide 3808 in a fixed orientation relative to one another, thereby facilitating the preparation of the afflicted area of the patient to receive the implant assembly 200 and implementing the subsequent formation of the implant assembly 200.

Detailed descriptions of various aspects of the delivery tool 300 including the targeting arm 108, fastener guide 3806, and implant guide 3808 are provided herein below.

a. Targeting Arm

Figure 39:
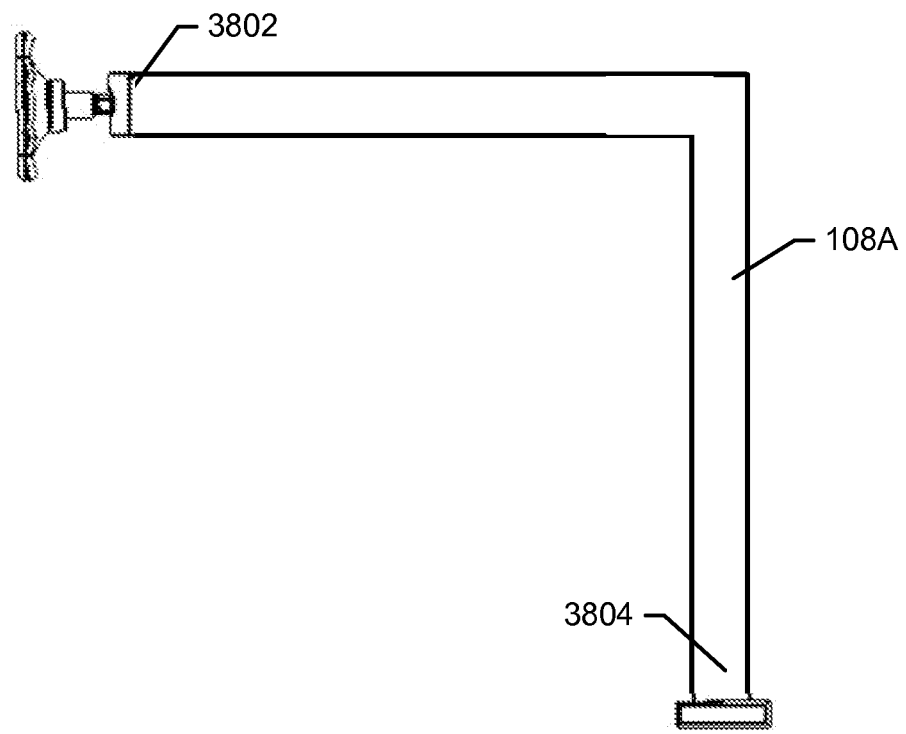
FIG. 39 is a side view of a targeting arm with a right-angle shape.

Referring again to FIG. 38, the targeting arm 108 in this aspect is an elongate element that may be fastened to the fastener guide 3806 at the first arm end 3802 and may further be fastened to the implant guide 3808 at the second arm end 3804. The targeting arm 108 in this aspect is an arcuate elongate element that functions as a robust structural member to maintain the fixed orientation of the fastener guide 3806 and the implant guide 3808 throughout an orthopedic surgical procedure. The targeting arm 108 may possess any known elongate shape without limitation including, but not limited to: a general curved arcuate shape as illustrated in FIG. 38, a circular arc shape, an elliptical arc shape, a polygonal shape, and a right-angle shape. FIG. 39 is a side view of a targeting arm 108A with a right-angle shape.

Figure 40:
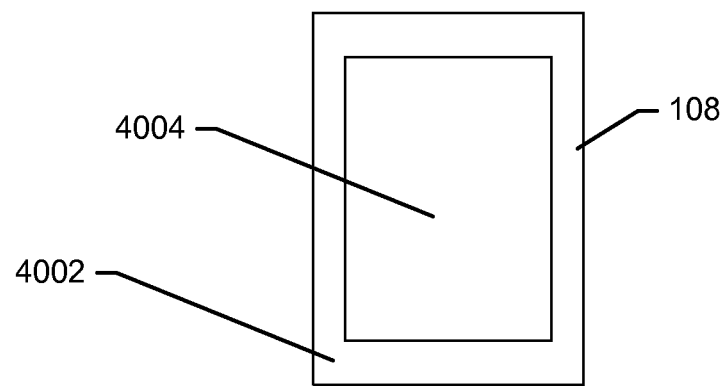
FIG. 40 is a transverse cross-sectional view of a targeting arm of the delivery tool illustrated in FIG. 38 taken at cross-sectional plane A-A.

The cross-sectional profile of the targeting arm 108 may be any profile without limitation. FIG. 40 is a transverse cross-section taken across the cross-sectional plane A-A illustrated in FIG. 38. In this aspect, the cross-sectional profile may be a hollow rectangular profile that includes an outer layer 4002 enclosing an inner lumen 4004. In other aspects, the cross-sectional profile may be a solid section rather than a hollow section. Other non-limiting examples if suitable cross-sectional profiles for the targeting arm 108 include: circular, elliptical, polygonal, triangular, square, rectangular, hexagonal, and any other known closed cross-sectional profile.

In other additional aspects, the cross-sectional profile of the targeting arm 108 may be essentially constant in size and shape along the length of the targeting arm 108, or the cross-sectional shape may vary along the length of the targeting arm 108. For example, the cross-sectional profile of the targeting arm 108 may thicken at the first arm end 3802 and second arm end 3804 to provide structural reinforcement for the attachment of the fastener guide 3806 and the implant guide 3808.

i. Adjustable Targeting Arms

Figure 41A:
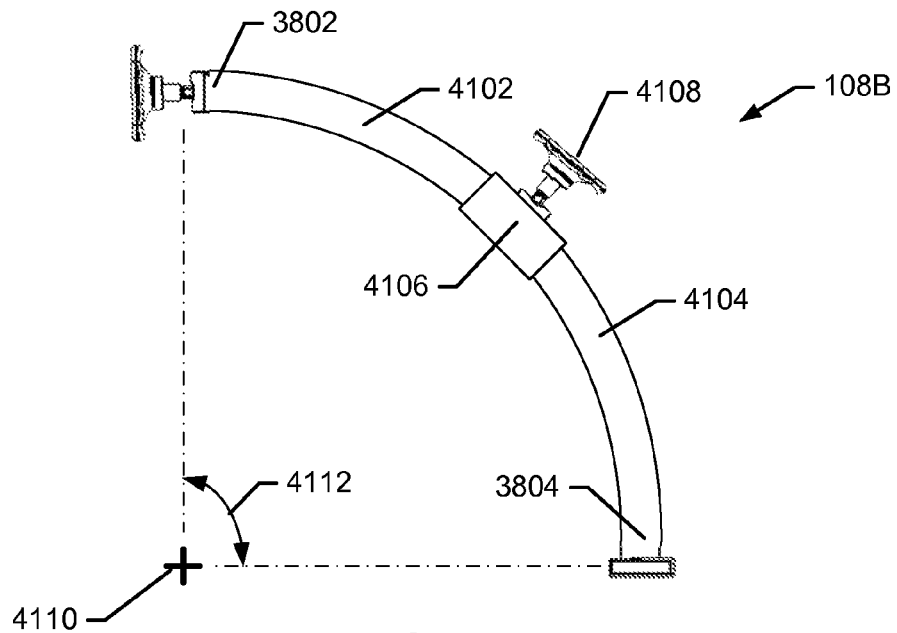
FIGS. 41A and 41B are side views of a telescoping targeting arm with arcuate shape.
Figure 41B:
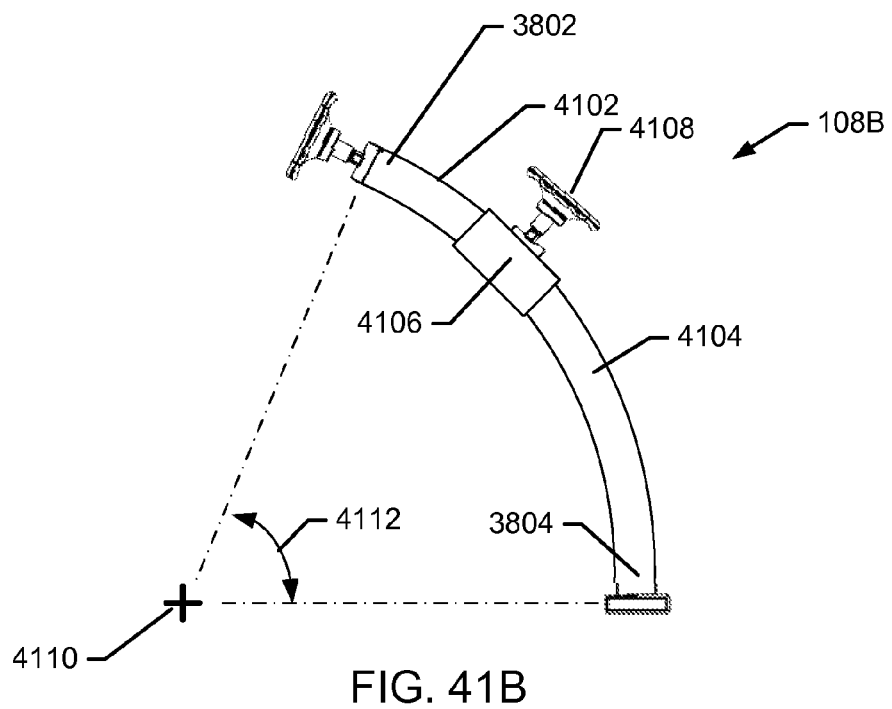

In one aspect, the targeting arm 108 may be provided as a single continuous structural element as illustrated in FIGS. 38 and 39, thereby providing a fixed elongate shape. In another aspect, the targeting arm 108 may be provided in the form of two or more linked structural elements thereby providing an adjustable elongate shape. For example, FIG. 41A and FIG. 41B are side views of a telescoping targeting arm 108B. Referring to FIG. 41A, the targeting arm 108B may include a first section 4102 ending in the first arm end 3802 and a second section 4104 ending in the second arm end 3804; both sections 4102 and 4104 may have matched circular arc shapes with a common center 4110 as illustrated in FIG. 41A. In an aspect, the second section 4104 may have a hollow cross-section with a central lumen (not shown), and the first section 4102 may be shaped and dimensioned to fit within the central lumen by sliding along the arc length of the second section 4104.

FIG. 41B illustrates the targeting arm 108B with a portion of the first section 4102 nested within the central lumen of the second section 4104, resulting in a shorter elongate shape. The second section 4104 includes the second arm end 3804 as well as a sliding attachment fitting 4106 at an end of the second section 4104 opposite to the second arm end 3804. The sliding attachment fitting 4106 may slide along the first section 4102 to adjust the relative position of the first arm end 3802 and second arm end 3804 as illustrated in FIG. 41B. The elongate shape of the targeting arm 108B and the sliding attachment fitting 4106 may be locked into a fixed position using a locking mechanism including, but not limited to, a set screw 4108 as illustrated in FIG. 41A. Any other known locking mechanism may be used to lock the adjustable targeting arm 108B into a locked position including, but not limited to clamps, pegs, compression fittings, and any combination thereof. In this aspect, the shorter elongate shape illustrated in FIG. 41B may result in a change in the angle 4112 between the fastener 106 and/or fastener guide 3806 and the implant body 102 and/or implant guide 3808 (not shown). The adjustability of the targeting arm 108B may further facilitate fine-tuning the entry paths of the various components during formation of the implant assembly 200 to account for variability in patient morphology and/or to avoid injury to vulnerable tissues including, but not limited to, neurons and/or blood vessels.

Figure 42A:
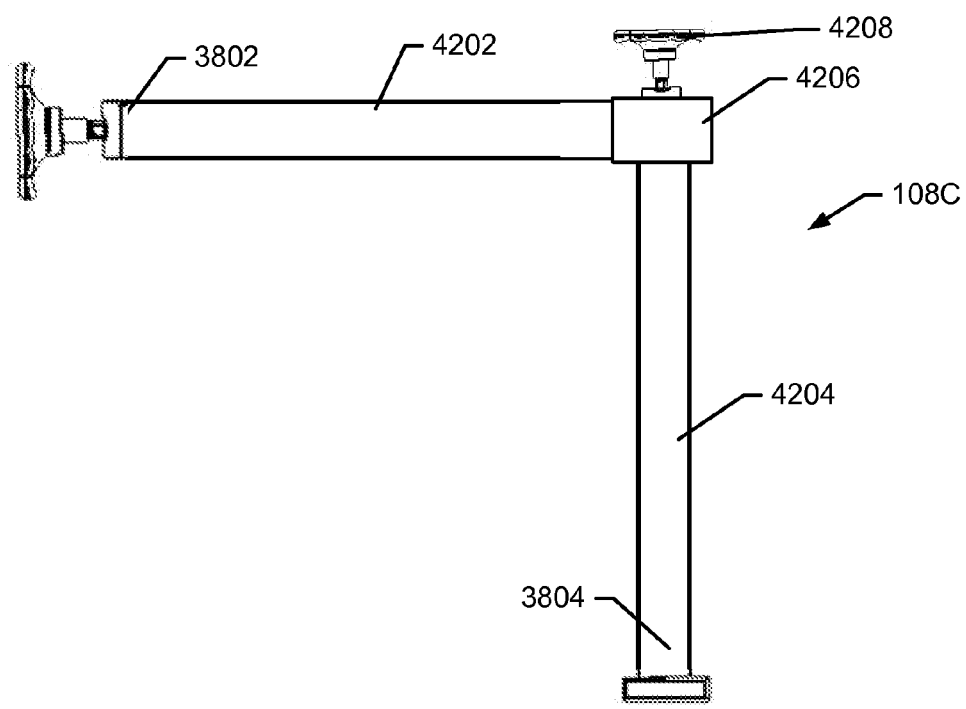
FIGS. 42A and 42B are side views of an adjustable targeting arm with a right-angle shape.
Figure 42B:
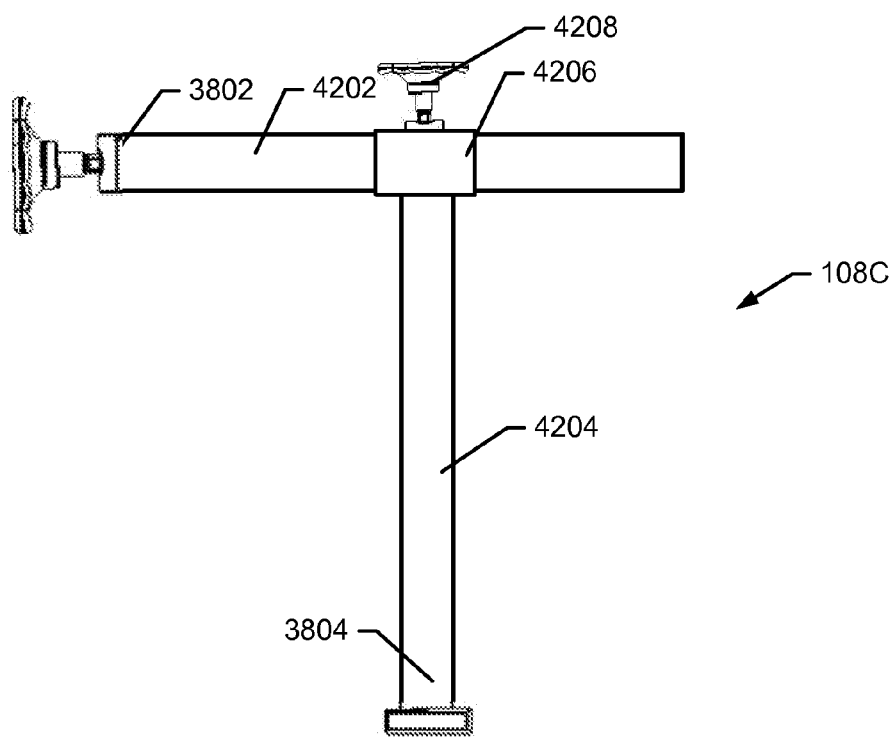

FIGS. 42A and 42B are side views of another adjustable targeting arm 108C in another aspect. In this aspect, the targeting arm 108C includes a straight horizontal segment 4202 and a straight vertical segment 4204. The vertical segment 4204 includes the second arm end 3804 as well as a sliding attachment fitting 4206 at an end of the vertical segment 4204 opposite to the second arm end 3804. The sliding attachment fitting 4206 may slide in a horizontal direction along the horizontal segment 4202 to adjust the relative position of the first arm end 3802 and second arm end 3804 as illustrated in FIG. 42B. The position of the sliding attachment fitting 4206 may be locked into place using any known locking mechanism described previously above including, but not limited to, a set screw 4208 as illustrated in FIG. 42B.

In various other aspects, the targeting arm 108 may be made adjustable by the incorporation of any other adjustable elements known in the art. Non-limiting examples of suitable adjustable elements include: two or more hinged or jointed subsections of the targeting arm 108, two or more telescoping subsections of the targeting arm 108, one or more bendable subsections of the targeting arm 108 having limited deformability, and any combination thereof. In other additional aspects, different sizes of fixed-geometry targeting arms 108 may be used to provide a suitable range of installation tool geometries to account for differences in patient morphologies, differences in orthopedic surgical procedures, and any other variable factor governing the selection of a targeting arm geometry.

ii. Fastener Guide Attachment Fitting

Figure 43A:
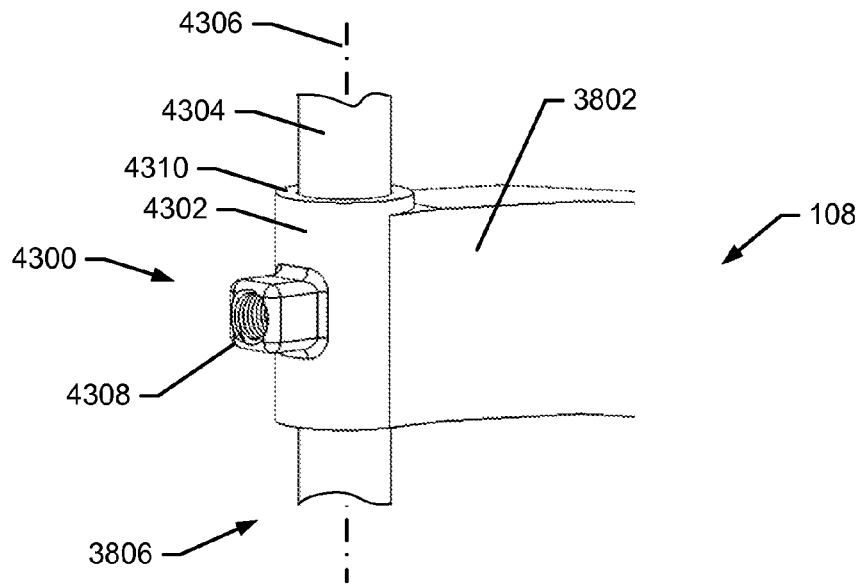
FIGS. 43A and 43B are detailed perspective views of a first end of the targeting arm illustrated in FIG. 38.
Figure 43B:
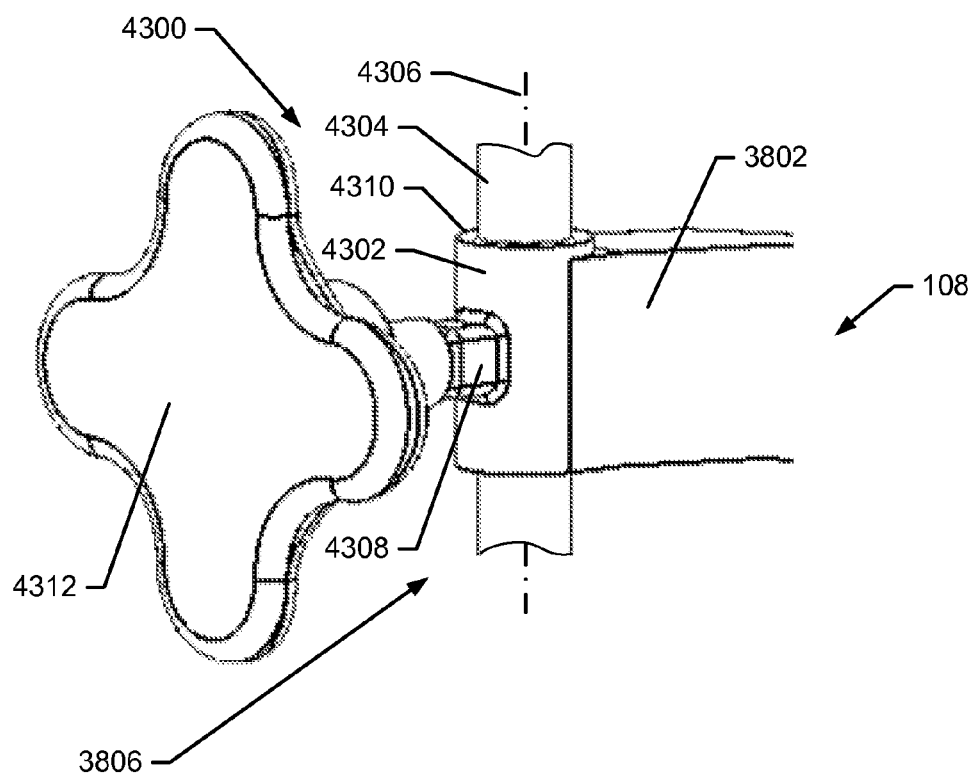

Referring again to FIG. 38, the targeting arm 108 may be attached to the fastener guide 3806 at the first arm end 3802. FIGS. 43A and 43B are close-up perspective views of the first arm end 3802 of the targeting arm 108 illustrated in FIG. 38. As illustrated in FIG. 43A, the first arm end 3802 may include a fastener guide attachment fitting 4300. The fastener guide attachment fitting 4300 may be designed to receive a portion of the fastener guide 3806 such as a fastener guide shaft 4304 in a reversibly locked mechanical engagement. When unlocked, the fastener guide attachment fitting 4300 may allow limited movement of the fastener guide 3806 including, but not limited to, rotation of the fastener guide 3806 about the fastener longitudinal axis 4306 and/or translation of the fastener guide 3806 along the fastener longitudinal axis 4306. However, even when unlocked, the fastener guide attachment fitting 4300 may maintain a fixed orientation between the fastener longitudinal axis 4306 and the implant longitudinal axis (not shown).

The fastener guide attachment fitting 4300 may incorporate any known mechanical attachment elements including a collar 4302 as illustrated in FIG. 43A. In this aspect, the collar 4302 may further include a threaded fitting 4308 that extends through the entire thickness of the collar wall 4310. A set screw 4312 may be advanced through the threaded fitting 4308 until the screw tip (not shown) compresses the fastener guide shaft 4304, thereby locking the fastener guide shaft 4304 in a reversibly locked mechanical engagement.

In other aspects, any other known mechanical elements capable of forming a reversibly locked mechanical engagement may be incorporated into the fastener guide attachment fitting 4300. Non-limiting examples of other mechanical elements suitable for incorporation into the fastener guide attachment fitting 4300 include: collars and one or more set screws; collars and one or more cotter pins, pegs, and or any other insertable elongate element; clamps; bands; compression fittings, and any combination thereof.

iii. Implant Guide Attachment Fitting

Figure 44A:
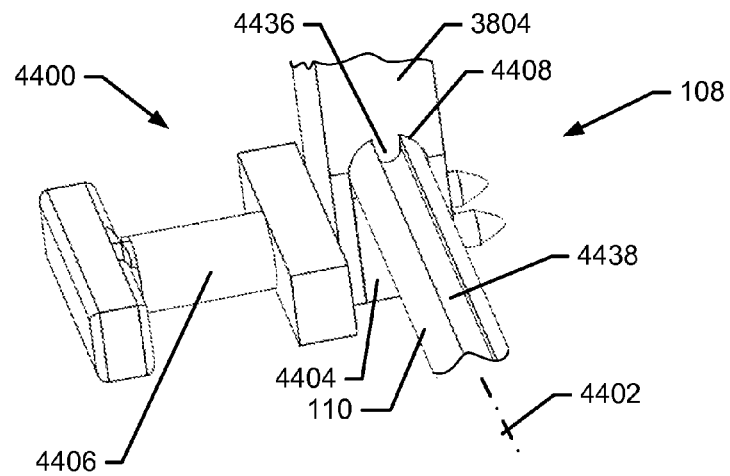
FIG. 44A is a detailed perspective view of a second end of a targeting arm and a retaining rod.

Referring again to FIG. 38, the targeting arm 108 may be attached to the implant guide 3808 at the second arm end 3804. FIG. 44A is a close-up perspective view of the second arm end 3804 of the targeting arm 108 and the retaining rod 110. As illustrated in FIG. 44A, the second arm end 3804 may include an implant guide attachment fitting 4400. The implant guide attachment fitting 4400 may be designed to receive a portion of the implant guide 3808 such as a retaining rod 110 in a reversibly locked mechanical engagement. When unlocked, the implant guide attachment fitting 4400 may allow limited movement of the implant guide 3808 including, but not limited to, the rotation of the retaining rod 110 about the implant longitudinal axis 4402. However, even when unlocked, the implant guide attachment fitting 4400 may maintain a fixed orientation between the implant longitudinal axis 4402 and the fastener longitudinal axis 4306 (not shown).

As illustrated in FIG. 44A, the implant guide attachment fitting 4400 may include a guide block 4404 locked into place by a pin assembly 4406. Together, the guide block 4404 and the second arm end 3804 form a channel 4408 within which a section of the retaining rod 110 may be locked in place. The channel 4408 is typically shaped and dimensioned to closely fit the cross-sectional profile and dimensions of the retaining rod 110. The channel 4408 may be any cross-sectional shape without limitation. In one aspect, the channel 4408 may include projections extending radially inward or depressions extending radially outward from the implant longitudinal axis 4402, discrete pins and/or pin receptacles, or any other feature known in the art for securing a section of an elongate member and/or inhibiting translation and/or rotation of the elongate member. For example, the channel 4408 may include a downward-projecting finger 4436 formed within the second arm end 3804 of the targeting arm 108 that fits closely within a groove 4438 extending longitudinally along at least a section of the retaining rod 110 as illustrated in FIG. 44A.

Figure 44B:
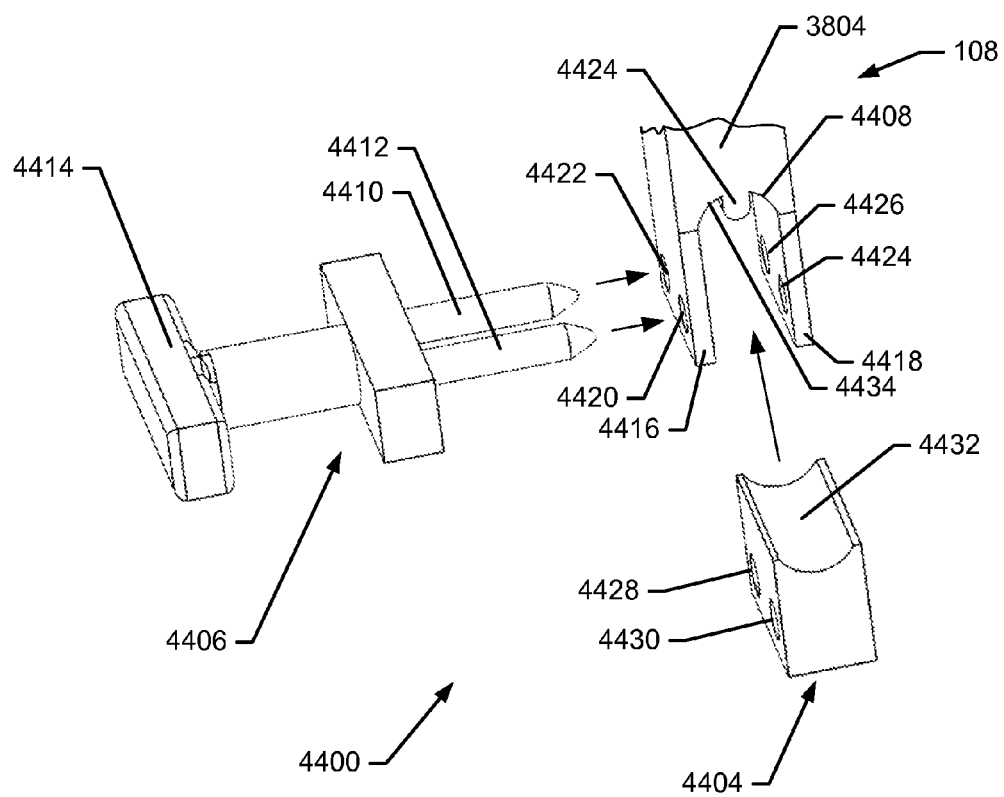
FIG. 44B is an exploded perspective view of the implant guide attachment fitting illustrated in FIG. 44A.

FIG. 44B is an exploded perspective view of the implant guide attachment fitting 4400 illustrated in FIG. 44A. The pin assembly 4406 may include a pair of pins 4410 and 4412 projecting from a pin handle 4414. The second arm end 3804 may include a pair of flanges 4416 and 4418 projecting downward from the second arm end 3804. A first pair of holes 4420 and 4422 may be formed in the first flange 4416 and a second pair of holes 4424 and 4426 may be formed in the second flange 4418 that extend through the full width of the flanges 4416 and 4418. Holes 4420 and 4424 are aligned and dimensioned to receive pin 4412; holes 4422 and 4426 are similarly aligned and dimensioned.

The guide block 4404 may be shaped and dimensioned to fit snugly between the flanges 4416 and 4418. An upper surface 4432 may be shaped and dimensioned to match the cross-sectional profile of a lower portion of the retaining rod 110. Together, the lower surface 4434 of the second arm end 3804 and the upper surface 4432 of the guide block 4404 may define the channel 4408. In one aspect, the lower surface 4434 and/or upper surface 4432 may further include a surface texture to inhibit slipping of the retaining rod 110 when the implant guide attachment fitting 4400 is in a locked mechanical engagement with the retaining rod 110.

The guide block 4404 may further include a pair of holes 4428 and 4430 that extend through the width of the guide block 4404 and align with holes 4422/4426 and 4420/4424 respectively to receive pins 4410 and 4412 during assembly of the implant guide attachment fitting 4400. In one aspect, the holes 4428 and 4430 on the guiding block 4404 may be situated such that the upper surface 4432 may compress the retaining rod 110 against the lower surface 4434 of the second arm end 3804 when the pin assembly 4406 is inserted though the flanges 4416/4418 and the guide block 4404. In this aspect, the compression may be sufficient to result in a friction fit to hold the retaining rod 110 locked into place.

In other aspects, any other known mechanical elements capable of forming a reversibly locked mechanical engagement may be incorporated into the implant guide attachment fitting 4400. Non-limiting examples of other mechanical elements suitable for incorporation into the implant guide attachment fitting 4400 include: collars and one or more set screws; collars and one or more cotter pins, pegs, and or any other insertable elongate element; clamps; bands; compression fittings, and any combination thereof.

b. Fastener Guide

Referring again to FIG. 38, the delivery tool 300 may include a fastener guide 3806 fastened to the first arm end 3802 of the targeting arm 108. The fastener guide 3806 may be used to prepare the afflicted region of the patient for the insertion of a fastener 106 and to implement the delivery and attachment of the fastener 106 as part of the formation of the implant assembly 200. In various aspects, the preparation of the afflicted region of the patient may include drilling, cutting, grinding, or otherwise removing intervening tissues such as connective tissues and bone tissues to facilitate the subsequent insertion of the fastener 106. The preparation of the afflicted region of the patient may further include obtaining images of the afflicted region before, during, and/or after the insertion of the fastener 106. The delivery and attachment of the fastener 106 may further include standard surgical fastener insertion techniques known in the art including, but not limited to the insertion and withdrawal of a trocar, a guidewire, a drill, a screwdriver, a chisel, and/or any other known surgical tool associated with the delivery and attachment of surgical fasteners. In various aspects, the fastener guide 3806 may be used to perform the surgical procedures associated with insertion and attachment of the fastener 106 to the other elements of the implant assembly 200 while maintaining a precise alignment of the fastener 106 relative to these other elements of the implant assembly 200.

Figure 45:
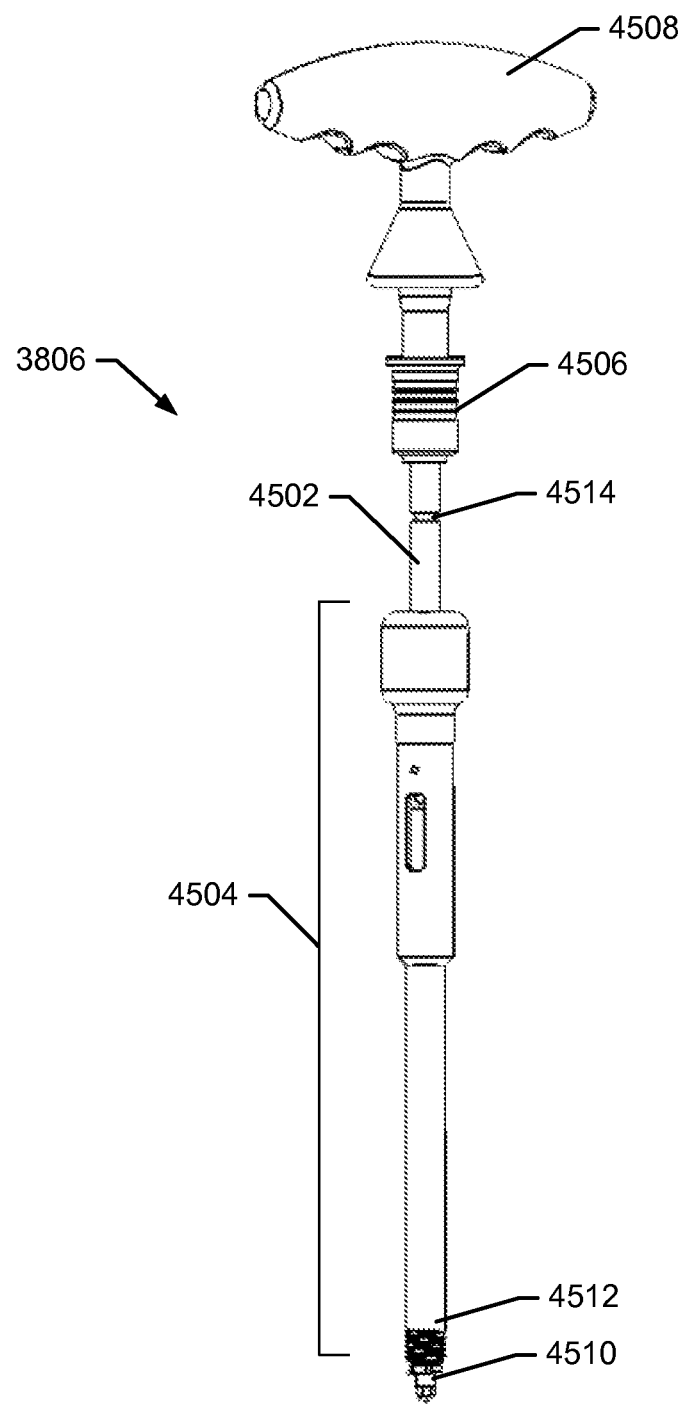
FIG. 45 is a side view of the fastener guide illustrated in FIG. 38.

By way of example, FIG. 45 is a side view of the fastener guide 3806 illustrated in FIG. 38. In this aspect, the fastener guide 3806 may include a bone screw inserter 4502 nested within a threaded sleeve 4504. The proximal end 4506 of the bone screw inserter 4502 may be reversibly attached to a removable handle 4508. The distal end 4510 of the bone screw inserter 4502 may protrude from the distal end 4512 of the threaded sleeve 4504. The bone screw inserter 4502 may further include a circumferential groove 4514 or other fitting element to which the fastener guide attachment fitting 4300 of the targeting arm 108 may attach in a reversible locked engagement. For example, the circumferential groove 4514 may be dimensioned and situated to receive the tip of the set screw 4312 of the fastener guide attachment fitting 4300 as illustrated in FIG. 43B.

i. Bone Screw Inserter

Figure 46:
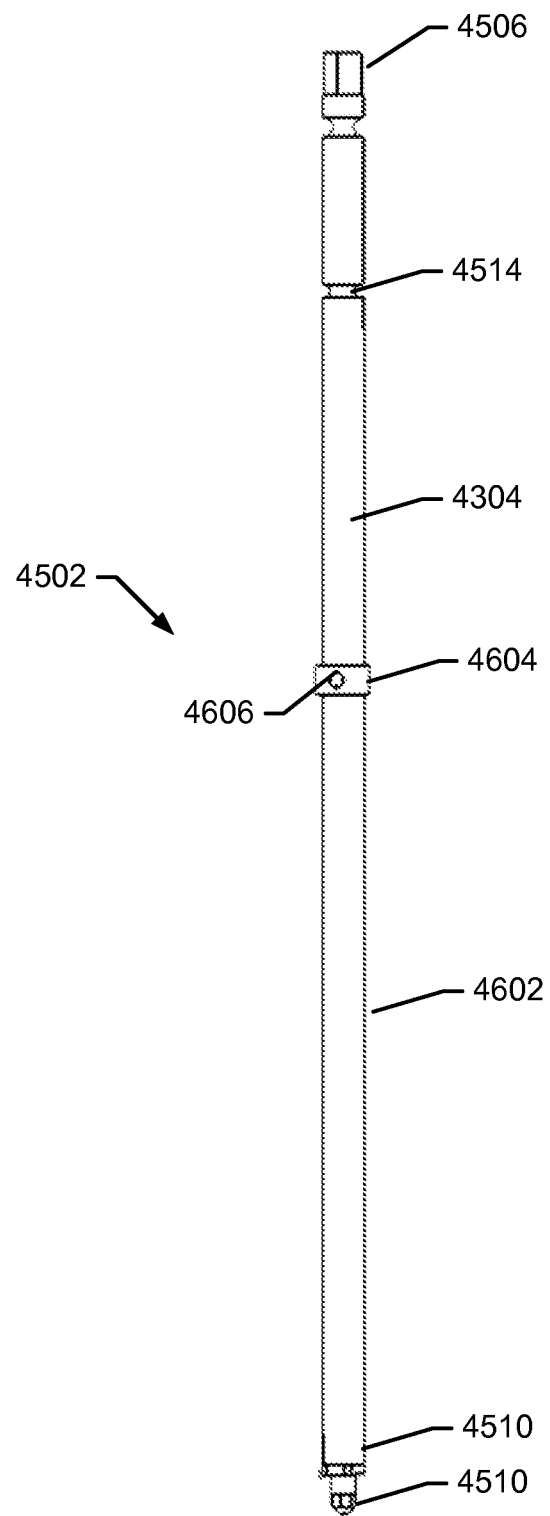
FIG. 46 is a detailed side view of the bone screw inserter illustrated in FIG. 45 with the threaded sleeve and removable handle removed.
Figure 47:
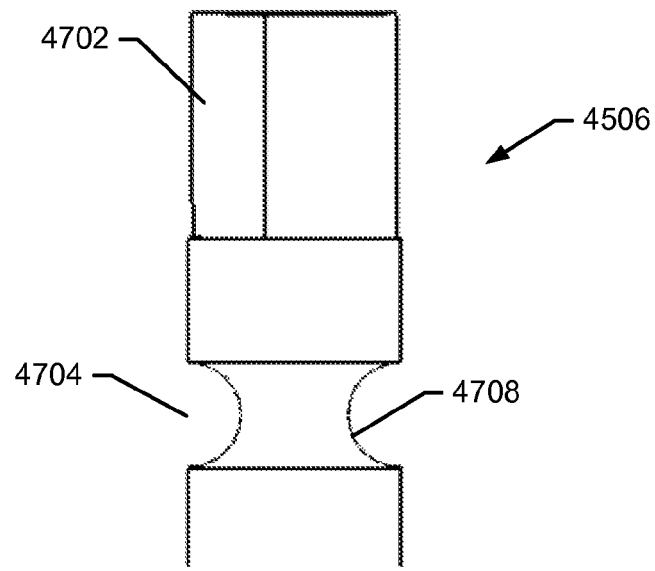
FIG. 47 is a detailed proximal perspective view of the proximal end of the bone screw inserter illustrated in FIG. 46.

FIG. 46 is a side view of the bone screw inserter 4502 illustrated in FIG. 45 with the threaded sleeve 4504 and the removable handle 4508 removed to expose the features of the bone screw inserter 4502. The bone screw inserter 4502 may include a fastener guide shaft 4304 with the proximal end 4506 and the opposite distal end 4510. The proximal end 4506 of the bone screw inserter 4502 may include features that mechanically interlock with corresponding features of the removable handle 4508. FIG. 47 is an enlargement of the side view of the proximal end 4506 of the bone screw inserter 4502 illustrated in FIG. 46.

Figure 48:
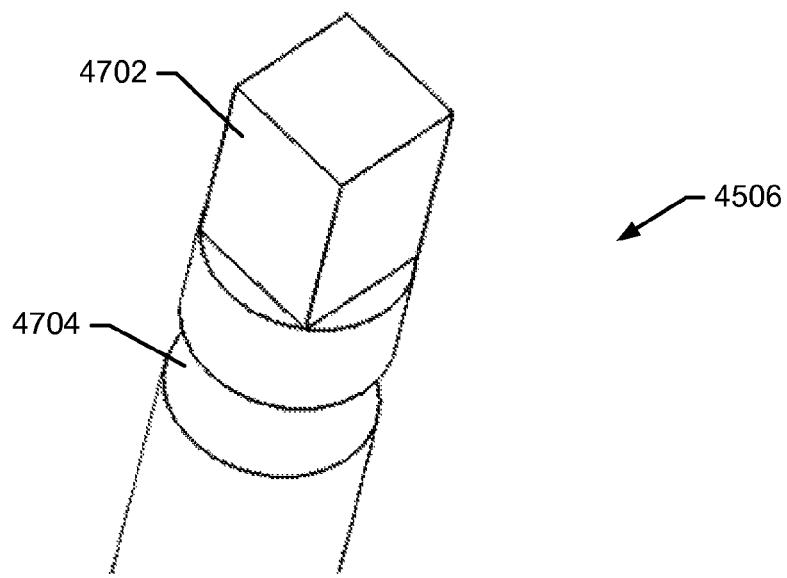
FIG. 48 is a detailed perspective view of a proximal end of a bone screw inserter.

The proximal end 4506 may include a proximal tip segment 4702 having a non-circular cross-sectional profile that transitions to a cylindrical segment 4706 situated between the proximal tip segment 4702 and a second circumferential groove 4704. FIG. 48 is a perspective view of the proximal end 4506 at a scale comparable to the scale of the view illustrated in side view in.

Figure 49:
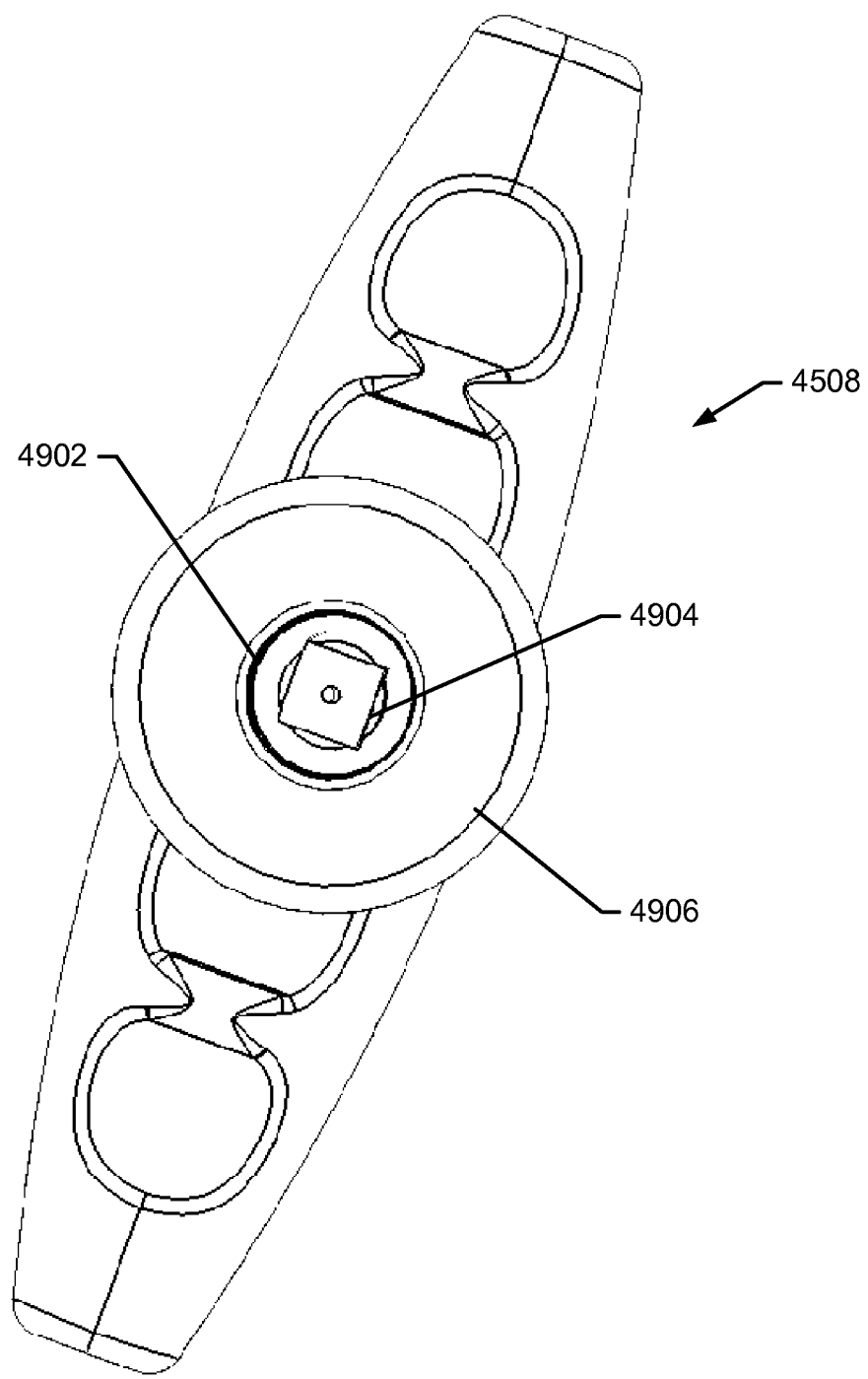
FIG. 49 is a bottom view of a removable handle.

FIG. 47. FIG. 49 is a bottom view of the removable handle 4508. Referring to FIGS. 48 and 49, the proximal tip segment 4702 of the bone screw inserter 4502 fits within a corresponding four-sided fitting 4904 at the bottom of a central bore 4902 formed within a vertical portion 4906 of the removable handle 4508.

Referring back to FIG. 47, the second circumferential groove 4704 includes a groove wall 4708 with a semi-circular cross-sectional profile. This circumferential groove 4704 may be designed to accommodate additional corresponding elements of the removable handle 4508, including but not limited to retaining balls (not shown). A more detailed description of the mechanical interaction of the proximal end of the bone screw inserter 4502 and the removable handle 4508 are provided herein below.

Referring back to FIG. 46, the bone screw inserter 4502 may further include a cylindrical collar 4604 attached to the fastener guide shaft 4304 using a reversibly locking mechanism such as a set screw 4606. In an aspect, the collar 4604 may fit tightly within the threaded sleeve 4504 (not shown). The collar 4604 may inhibit lateral play of the bone screw inserter 4502 within the threaded sleeve 4504 during use, and/or may limit the range of motion of the bone screw inserter 4502 within the bone screw inserter 4502 in the proximal-distal direction. For example, the collar 4604 may be situated in a position on the fastener guide shaft 4304 such that the maximal distal protrusion of the distal end 4510 may be such that the fastener 106 (not shown) interlocks with corresponding locking element of the implant assembly 200 (not shown) without overshooting and/or damaging the corresponding locking element.

Again referring to FIG. 46, the bone screw inserter 4502 may further include a distal end 4510 that includes elements to mechanically interact with the fastener 106 (not shown) during formation of the implant assembly 200 (not shown). As illustrated in FIG. 45, the distal end 4510 of the bone screw inserter 4502 protrudes from the distal end 4512 of the threaded sleeve 4504. The two distal ends 4510 and 4512 and associated features act in concert to situate and install a fastener 106 (not shown) as part of the formation of the implant assembly 200 (not shown). A detailed description of the mechanical interaction of the fastener 106 and distal ends 4510 and 4512 are provided herein below.

Figure 50:
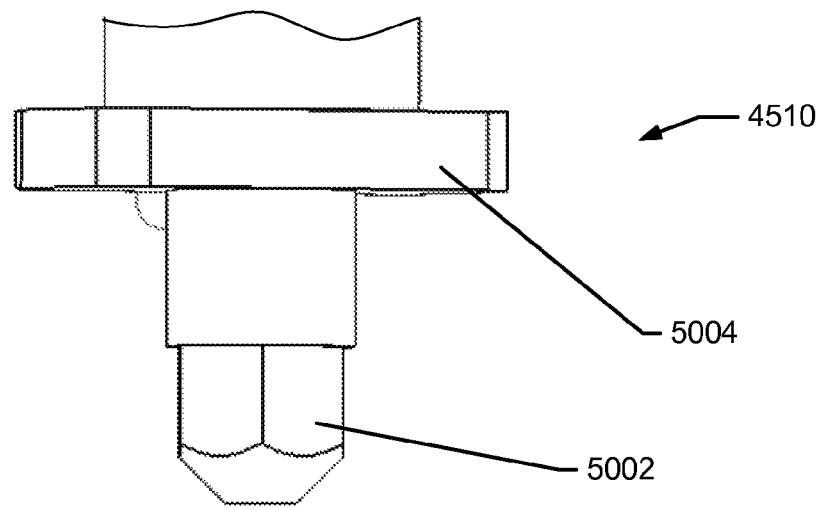
FIG. 50 is a detailed side view of the distal end of the bone screw inserter illustrated in FIG. 46.
Figure 51:
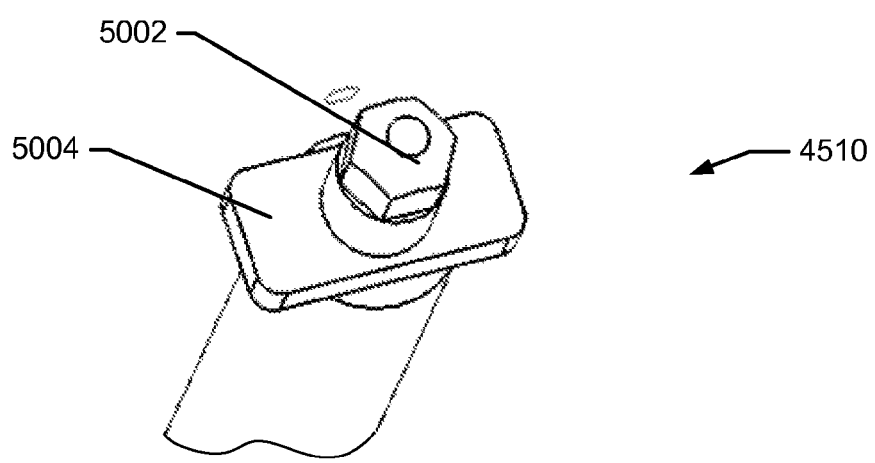
FIG. 51 is a distal perspective view of the distal end of the bone screw inserter illustrated in FIG. 46.

FIG. 50 is a close-up side view of the distal end 4510 of the bone screw inserter 4502 illustrated in FIG. 46. FIG. 51 is a perspective view of the distal end 4510 at a similar scale to the distal end 4510 illustrated in FIG. 50. Referring to FIGS. 50 and 51, the distal end 4510 may include a screwdriver tip 5002 and an additional screw head fitting 5004 situated proximally relative to the screwdriver tip 5002. The screwdriver tip 5002 may have a cross-sectional profile corresponding to any known screw head fitting 5004 including, but not limited to: flat blade profile, Phillips head profile, hexagonal profile as illustrated in FIGS. 50 and 51, star profile, and any other known screwdriver profile.

ii. Removable Handle

Referring back to FIG. 45, the fastener guide 3806 may include a removable handle 4508 in an aspect. In this aspect, the removable handle 4508 may be reversibly attached in a locked mechanical engagement to the proximal end 4506 any fastener guide tool such as the bone screw inserter 4502 as illustrated in FIG. 45. When attached, the removable handle 4508 may be used to twist the bone screw inserter 4502 about the longitudinal axis of the bone screw inserter 4502, to translate the bone screw inserter 4502 along its longitudinal axis in a proximal or distal direction, or to maintain the bone screw inserter 4502 and/or attached fastener 106 (not shown) in a fixed orientation relative to the other elements of the implant assembly 200 (not shown) during the formation of the implant assembly 200.

Figure 52:
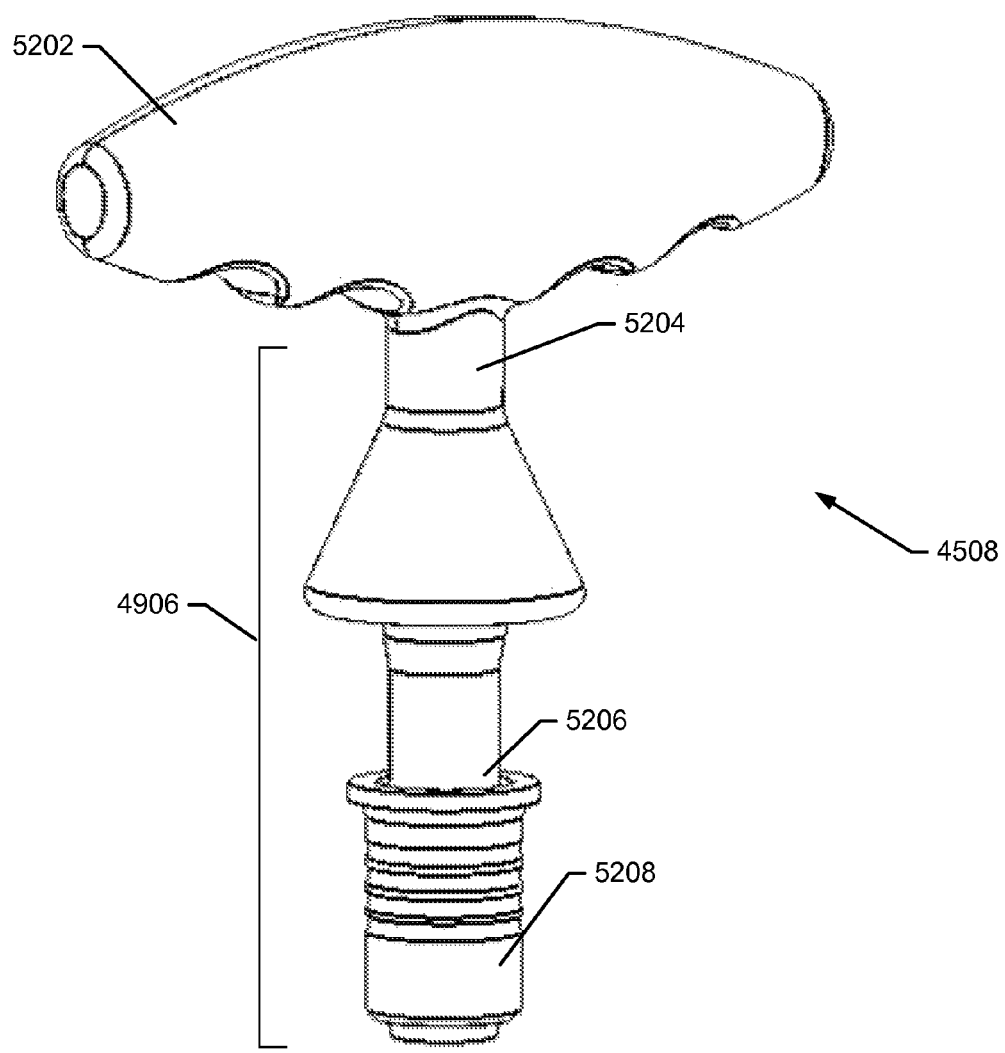
FIG. 52 is an enlarged side view of the removable handle illustrated in FIG. 45 with the threaded sleeve and bone screw inserter removed.

FIG. 52 is an enlarged side view of the removable handle 4508 illustrated in FIG. 45 with the threaded sleeve 4504 and the bone screw inserter 4502 removed to better expose the features of the removable handle 4508. The removable handle 4508 may include a vertical portion 4906 and a grip portion 5202. The grip portion 5202 may be grasped by a single hand and/or two hands by an orthopedic surgeon or other practitioner performing an orthopedic procedure.

In another aspect (not shown), the grip portion 5202 may include additional adaptor elements that may interact with powered actuators that may be used to situate and attach the fastener 106 during the formation of the implant assembly. Non-limiting examples of powered actuators include hydraulic and electromechanical pistons, electrical motors including stepper motors, screwjacks, and any other powered actuator known in the art. In this other aspect, the powered actuators may be operator-controlled and/or automatically controlled. Non-controlling examples of suitable additional adaptor elements include threaded fittings, projecting threaded and unthreaded shafts, gears, and any other adaptor element suitable for establishing a mechanical engagement with an actuator.

Figure 53:
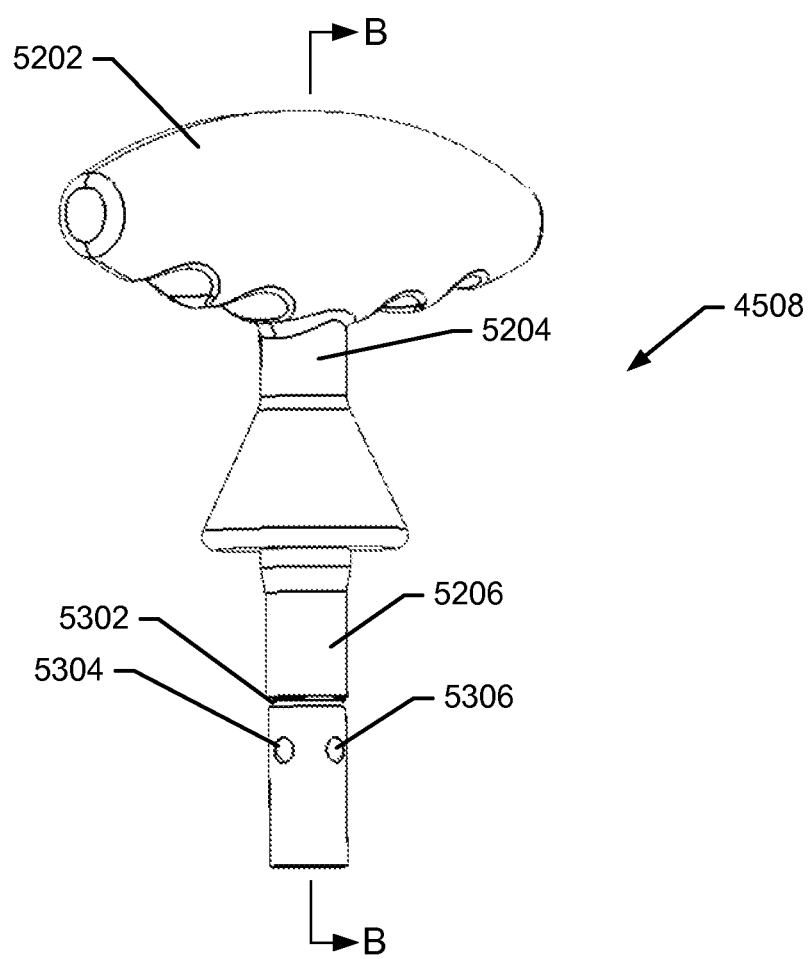
FIG. 53 is a side perspective view of a removable handle with the collar and underlying components removed.

Referring back to FIG. 52, a proximal end 5204 of the vertical portion 4906 may be attached to the grip portion 5202. In addition, a distal end 5206 of the vertical portion 4906 may be situated within a sliding collar 5208; the sliding collar 5208 may be used to lock and unlock the removable handle 4508 from the proximal end 4506 of the bone screw inserter 4502. FIG. 53 is a perspective view of the removable handle with the collar 5208 and underlying components removed to expose the underlying distal end 5206 of the removable handle 4508. The distal end 5206 may further include a circumferential groove 5302 and a pair of holes 5304 and 5306 to contain a pair of retaining bearings (not shown). The external cross-sectional profile of the distal end 5206 may be any shape without limitation including, but not limited to the circular profile illustrated in FIG. 53 and FIG. 49.

Figure 54:
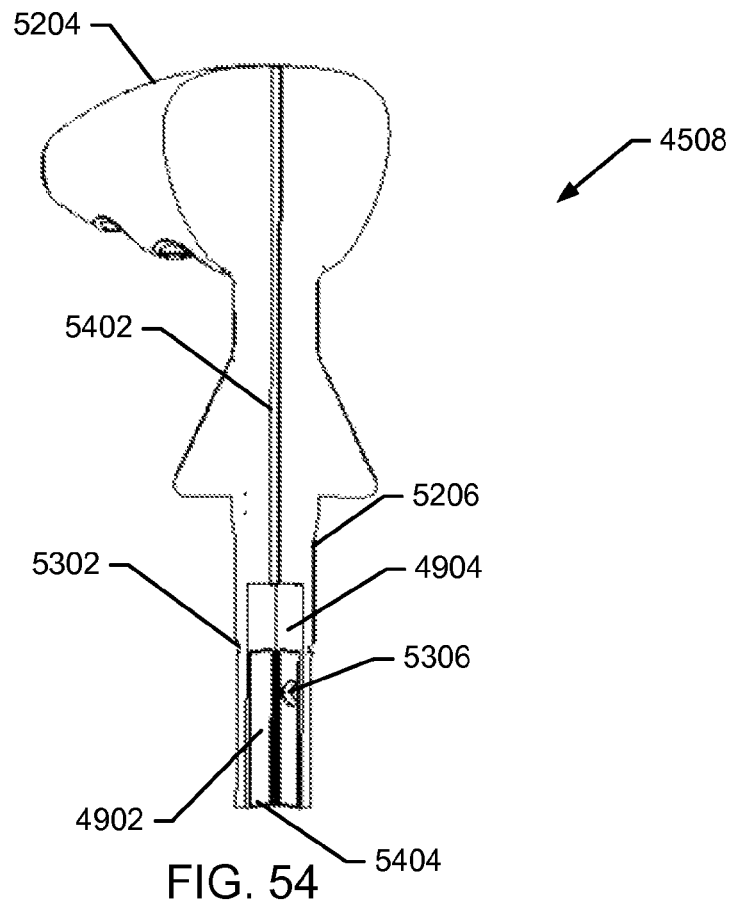
FIG. 54 is a longitudinal cross-sectional view of a removable handle taken at the plane B-B denoted in FIG. 53 and with the collar and underlying components removed.

FIG. 54 is a cross-sectional view taken at the plane B-B denoted in FIG. 53. The central bore 4902 is situated within the distal end 5206 that opens to a channel 5402 proximally and to the distal face 5404 distally. The most proximal region of the central bore 4902, situated most deeply within the bore, forms the four-sided fitting 4904 that receives the square proximal tip segment 4702 (not shown). In addition, the holes 5306 and 5304 (not shown) extend from the central bore 4902 to the outer surface of the removable handle 4508. The hollow channel 5402 is situated within the grip portion 5202 and may extend from the proximal end 5204 of the grip portion 5202 to the four-sided fitting 4904 within the central bore 4902. The channel 5402 may be used to introduce guidewires, optical fibers, drill bits, and any other known device or element suitable for use in an orthopedic procedure.

Figure 55:
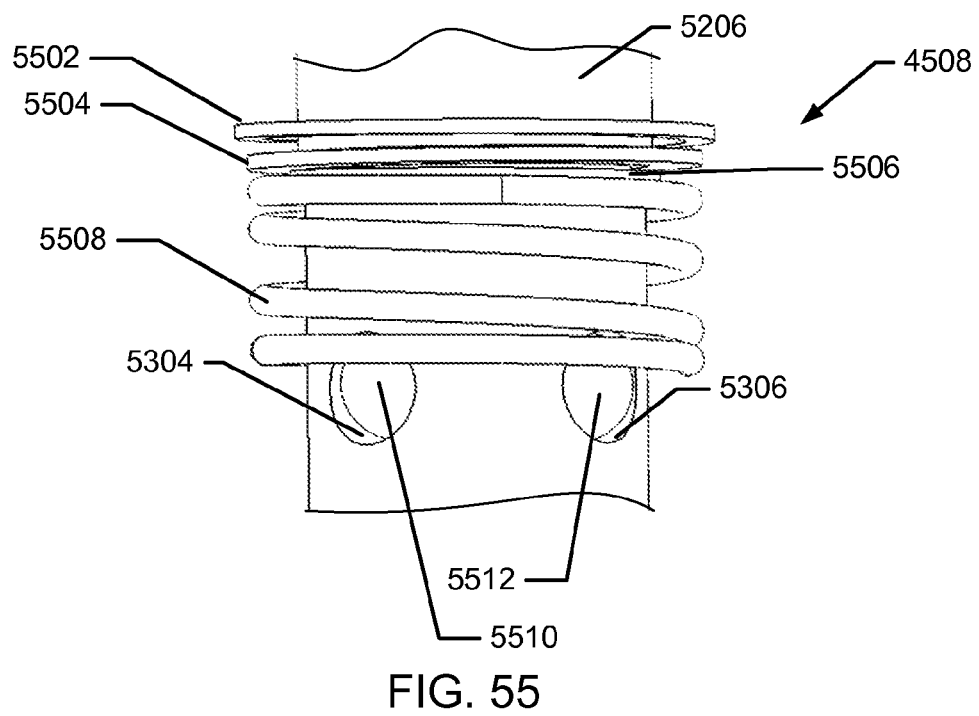
FIG. 55 is a detailed side view of a distal end of a handle with a sliding collar removed.

FIG. 55 is a close-up side view of the distal end 5206 of the removable handle 4508 with the sliding collar 5208 removed to expose the underlying elements of the locking mechanism of the removable handle 4508. In this aspect, a large lock washer coil 5502 is situated just proximal to the circumferential groove 5302 illustrated in FIGS. 53 and 54. A lock washer 5504 is situated within the circumferential groove adjacent in the distal direction to the large lock washer coil 5502. A small lock washer coil 5506 is situated adjacent to the lock washer 5504 opposite to the large lock washer coil 5502, and a spring 5508 is situated adjacent to the small lock washer coil 5506 opposite to the lock washer 5504. Retaining bearings 5510 and 5512 are situated within holes 5304 and 5406, respectively, such that the retaining bearings 5510 and 5512 protrude into the central bore 4902 distal to the four-sided fitting illustrated in FIG. 54.

Figure 56:
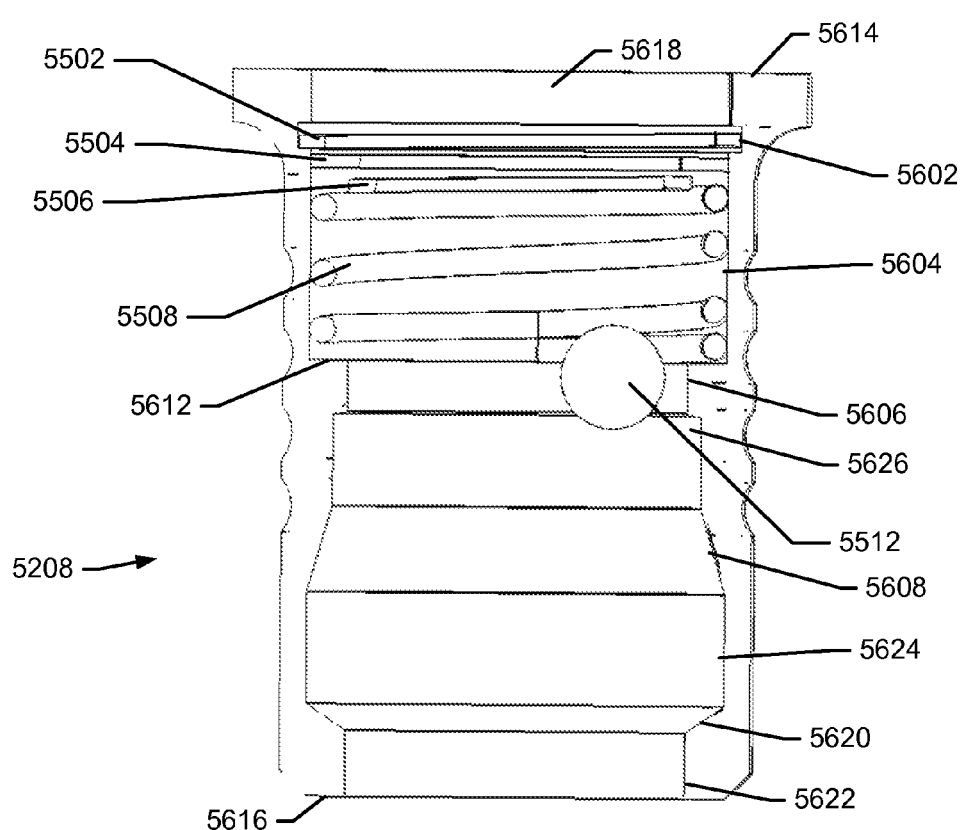
FIG. 56 is a longitudinal cross-sectional view taken through the collar and underlying components illustrated in FIG. 52 with the distal portion of the handle removed.

FIG. 56 is a longitudinal cross-section taken through the collar 5208 and underlying components illustrated in FIG. 52 with the distal end 5206 of the removable handle 4508 removed to enhance the visualization of the orientation of the underlying components within the inner surface of the collar 5208. The collar 5208 in this aspect contains a series of lumen segments arranged in order from the proximal end 5614 to the distal end 5616 of the collar 5208, a large-diameter proximal opening segment 5618, an expanded circumferential groove segment 5602, a large-diameter spring segment 5604, a smaller-diameter restriction segment 5606, an expansion section 5608 with a smaller-diameter proximal end 5626 and a larger-diameter distal end 5624, a second distal restriction section 5620, and a smaller-diameter distal opening section 5622.

In this aspect, the large lock washer coil 5502 is situated within the circumferential groove segment 5602, and the lock washer 5504, the small lock washer coil 5506, and the spring 5508 are situated within the large-diameter spring segment 5604. The retaining bearings 5510 and 5512 (not shown) are situated in various segments depending on the locked or unlocked condition of the collar 5208 including, but not limited to, the smaller-diameter restriction segment 5606 in the locked condition and within the expansion section 5608 in the unlocked condition.

Figure 57:
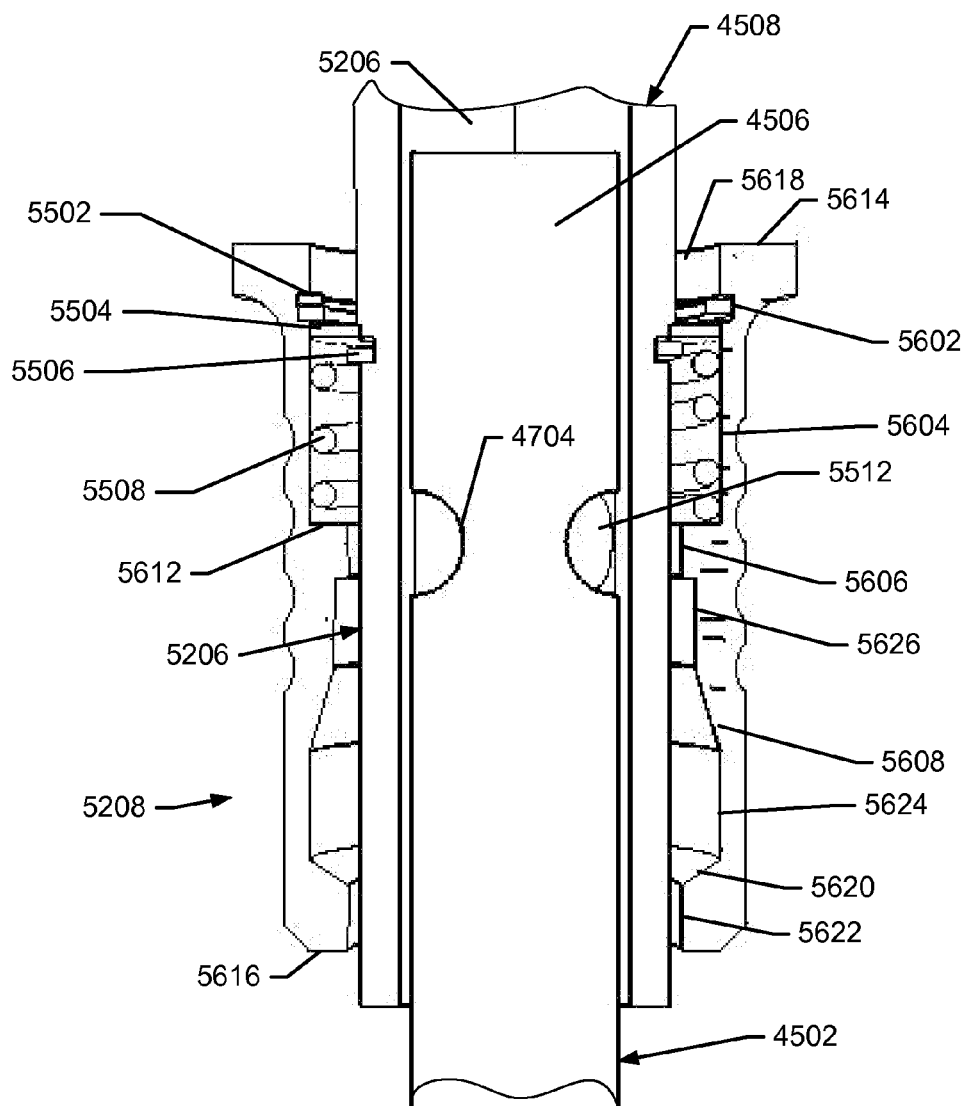
FIG. 57 is a longitudinal cross-sectional view taken through a collar and underlying components, a distal end of a handle, and a proximal end of a bone screw inserter.

FIG. 57 is a longitudinal cross-section similar to FIG. 56 taken through the collar 5208 and underlying components as well as the distal end 5206 of the removable handle 4508 and the proximal end 4506 of the bone screw inserter 4502. In the locked position, the retaining bearings 5510/5512 may be situated within the smaller-diameter restriction segment 5606 of the collar 5208, thereby forcing the retaining bearings 5510/5512 into the circumferential groove 4704 of the bone screw inserter 4502, thereby locking the bone screw inserter 4502 in place within the removable handle 4508. To unlock the bone screw inserter 4502 from the removable handle 4508, the collar 5208 may be displaced in a proximal (upward) direction, thereby situating the retaining bearings 5510/5512 within the larger-diameter distal end 5624. When the bone screw inserter 4502 is slid distally (downward) out of the removable handle 4508, the retaining bearings 5510/5512 may now fall out of the circumferential groove 4704, allowing the removal of the bone screw inserter 4502. Because the spring 5508 is compressed between the lock washer 5504 and a shoulder 5612 within the large-diameter spring segment 5604, the collar 5208 passively returns to a locked position when the spring 5508 extends to the uncompressed position illustrated in FIG. 57.

iii. Threaded Sleeve

Figure 58:
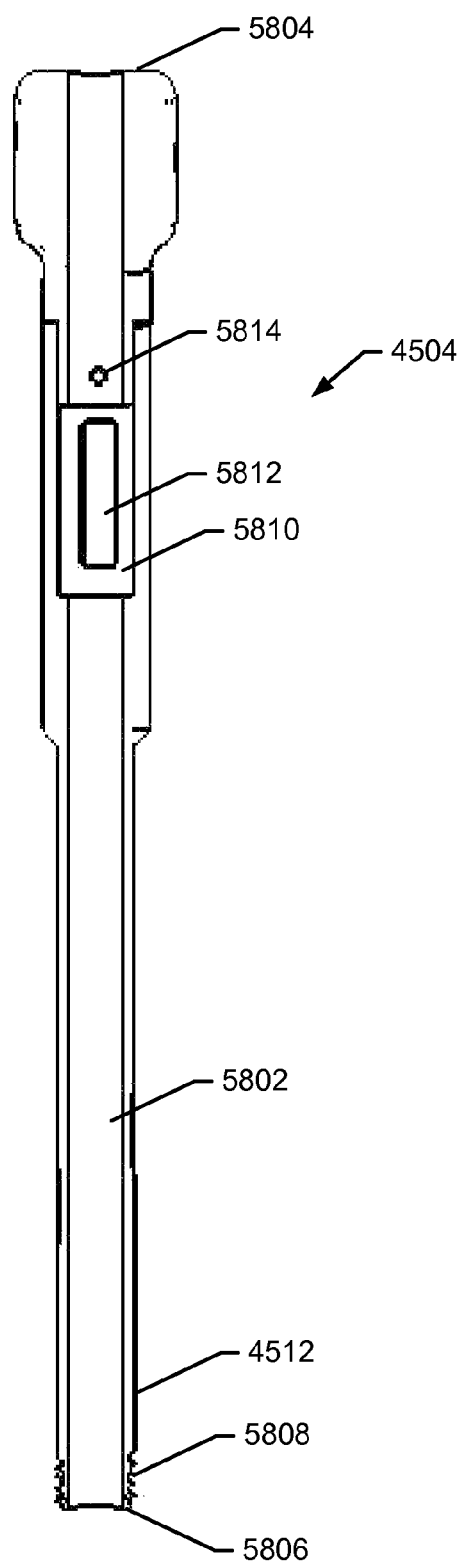
FIG. 58 is a longitudinal cross-section of a threaded sleeve taken in a plane approximately parallel with the drawing plane of FIG. 45 and coincident with a longitudinal axis of a threaded sleeve.

Referring back to FIG. 45, the fastener guide 3806 may include a threaded sleeve 4504 in an aspect. In this aspect, the bone screw inserter 4502 may be situated within the threaded sleeve 4504 such that the distal end 4510 of the bone screw inserter 4502 protrudes from the distal end 4512 of the threaded sleeve 4504. FIG. 58 is a longitudinal cross-section of the threaded sleeve 4504 taken in a plane approximately parallel with the drawing plane of FIG. 45 and coincident with the longitudinal axis of the threaded sleeve 4504. The bone screw inserter 4502 was removed from this cross-section to expose the internal features of the threaded sleeve 4504 in this aspect.

As illustrated in FIG. 58, the threaded sleeve 4504 encloses a constant-diameter channel 5802 that runs the full length of the threaded sleeve 4504 and opens at the proximal face 5804 and at the distal face 5806. The cross-sectional profile and diameter of the channel 5802 may be selected to closely fit the outer cross-sectional profile of the fastener guide shaft 4304 of the bone screw inserter 4502. The distal end 4512 of the threaded sleeve 4504 may end in a threaded end 5808.

The threaded sleeve 4504 further encloses a larger-diameter expanded channel segment 5810. The cross-sectional diameter of the expanded channel segment 5810 may be selected to accommodate the outer diameter of the collar 4604 attached to the fastener guide shaft 4304 of the bone screw inserter 4502. The smaller diameter of the channel 5802 situated proximally and distally to the expanded channel segment 5810 cannot accommodate the outer diameter of the collar 4604 thereby restraining the movement of the collar 4604 and the attached bone screw inserter 4502 to within the expanded channel segment 5810.

The expanded channel segment 5810 may further include one or more windows 5812 opening to the outside of the threaded sleeve 4504 to provide a visual indication of the position and movements of the collar 4604 within the threaded sleeve 4504. In an aspect, a pair of windows 5812 may be situated in a diametrically opposed orientation. In another aspect (not shown), the fastener guide shaft 4304 may include radially projecting arms that project through the one or more windows. For example, if an orthopedic nail is selected as the fastener 106, the projecting arms may be used to produce a significant distally-directed force on the fastener guide shaft 4304 to hammer the orthopedic nail into place in the implant assembly 200.

The channel 5802 may further include one or more holes 5814 opening to the outside of the threaded sleeve 4504. In one aspect (not shown), a pair of diametrically opposed holes may be included to provide access for a locking pin, set screw, or other mechanical locking element to lock the fastener guide shaft 4304 into a fixed position within the threaded sleeve 4504. In this aspect, the mechanical locking element would enter the threaded sleeve 4504 through a first hole 5814A, pass through a second hole formed within the fastener guide shaft 4304, and exit the threaded sleeve 4504 through a third hole 5814B situated diametrically opposite to the first hole 5814A.

Figure 59:
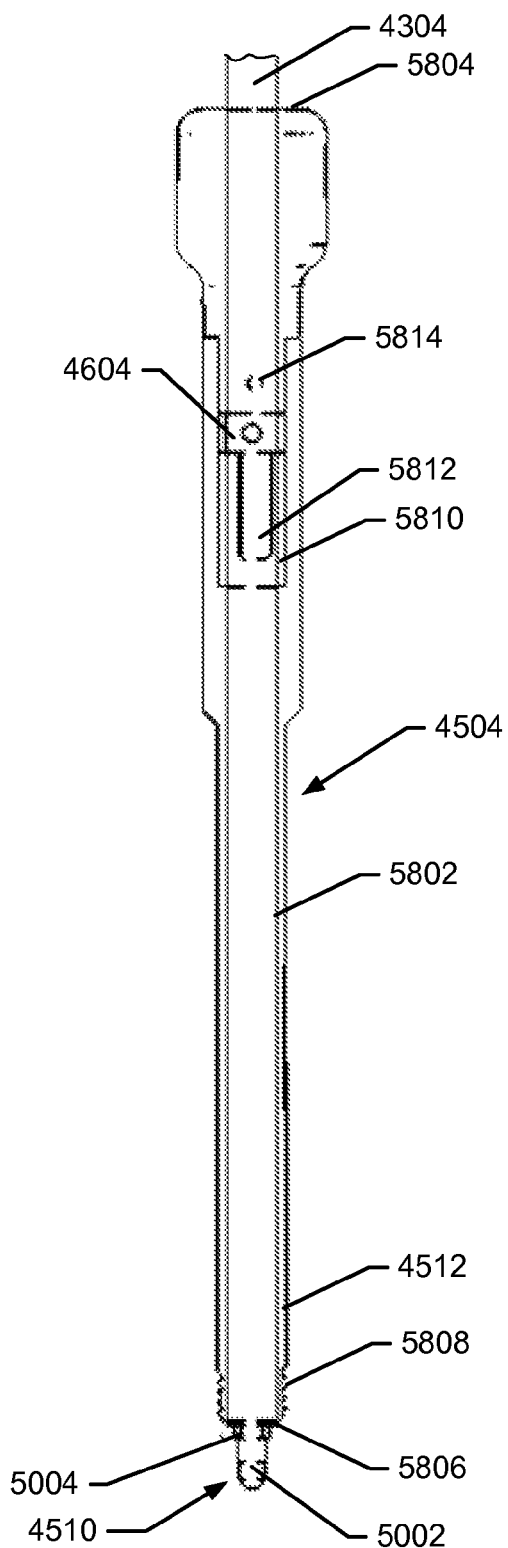
FIG. 59 is a longitudinal cross-sectional view of FIG. 58 with the bone screw inserter included.

FIG. 59 is the same longitudinal cross-sectional view of the threaded sleeve 4504 illustrated in FIG. 58 with the bone screw inserter 4502 included to illustrate the spatial relationship of the elements of the bone screw inserter 4502 within the threaded sleeve 4504. The fastener guide shaft 4304 of the bone screw inserter 4502 is situated within the central channel 5802 of the threaded sleeve 4504; the fastener guide shaft 4304 of the bone screw inserter 4502 protrudes proximally from the proximal face 5804 and the distal end 4510 of the bone screw inserter 4502 distally from the distal face 5806 of the threaded sleeve 4504. The collar 4604 attached to the bone screw inserter 4502 is situated within the expanded channel segment 5810 of the threaded sleeve 4504.

Figure 60:
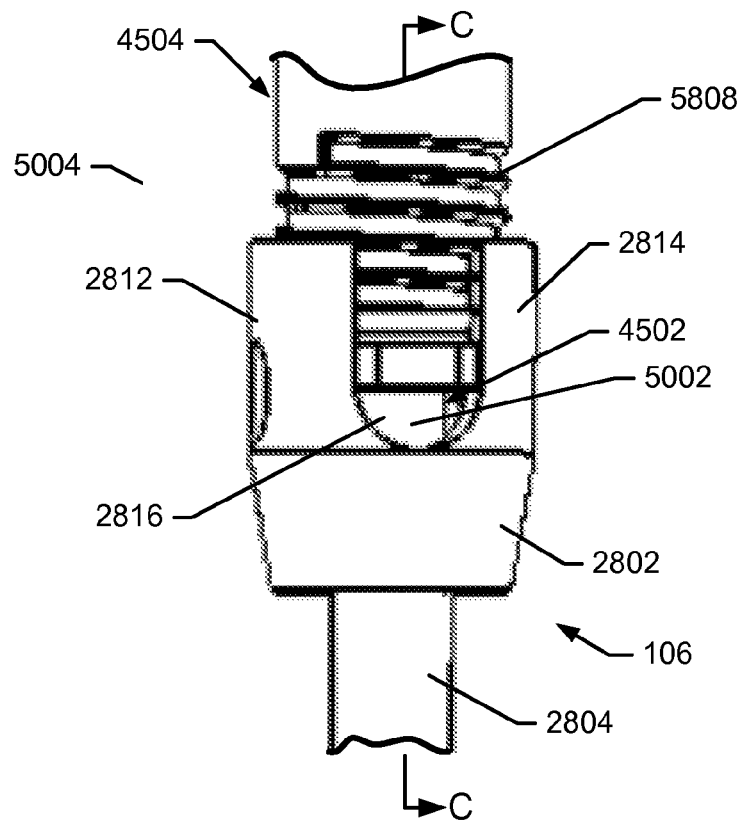
FIG. 60 is a side view of a head of a fastener attached to a bone screw inserter and threaded sleeve.
Figure 61:
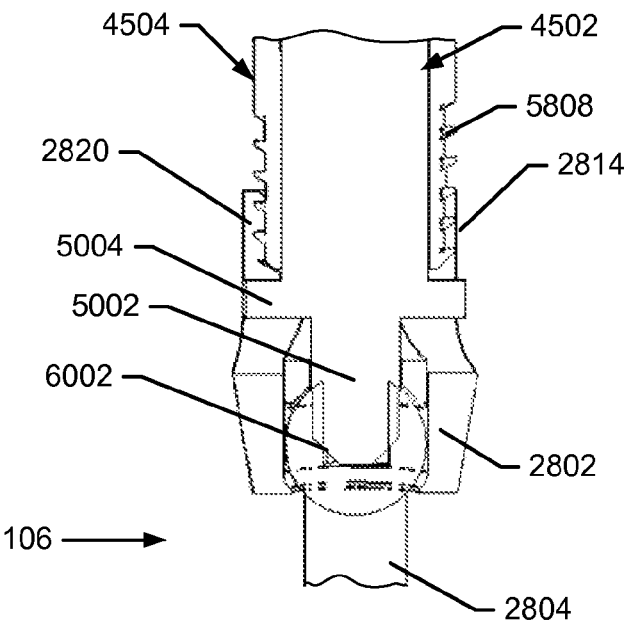
FIG. 61 is a detailed cross-sectional view of a head of a fastener attached to a bone screw inserter and threaded sleeve taken along the plane C-C illustrated in FIG. 60.

In an aspect, the threaded end 5808 of the threaded sleeve 4504 and the screwdriver tip 5002 and screw head fitting 5004 of the bone screw inserter 4502 cooperatively attach reversibly to the head of a fastener 106 (not shown) in a mechanically locked engagement during the formation of the implant assembly 200 (not shown). FIG. 60 is a side view of the head 2802 of a fastener 106 attached to the bone screw inserter 4502 and the threaded sleeve 4504. FIG. 61 is a cross-sectional view taken along the plane C-C illustrated in FIG. 60.

Referring to FIGS. 60 and 61, the screwdriver tip 5002 is situated within a corresponding screwdriver fitting 6002 formed within the head 2802 of the fastener 106, and the screw head fitting 5004 is situated within the upward-opening groove 2816 formed within the support elements 2812 and 2814 of the fastener head 2802. The threaded end 5808 of the threaded sleeve 4504 is advanced into the threaded fitting 2820 formed within the support elements 2812 and 2814 of the fastener head 2802.

c. Implant Guide

Referring again to FIG. 38, the delivery tool 300 may include an implant guide 3808 fastened to the second arm end 3804 of the targeting arm 108. The implant guide 3808 may be used to prepare a bore within the afflicted region of the patient, to insert the implant outer layer 104 and implant body 102 into the bore and to help implement the attachment of the fastener 106 as part of the formation of the implant assembly 200. In various aspects, the preparation of the bore within the afflicted region of the patient may include drilling, cutting, grinding, or otherwise removing intervening tissues such as connective tissues and bone tissues to facilitate the subsequent insertion of the implant outer layer 104 and implant body 102. The preparation of the bore within the afflicted region of the patient may further include obtaining images of the afflicted region before, during, and/or after the insertion of the implant outer layer 104 and implant body 102. The delivery and placement of the implant outer layer 104 and implant body 102 may further include standard surgical fastener insertion techniques known in the art including, but not limited to the insertion and withdrawal of a trocar, a guidewire, a drill, a screwdriver, a chisel, and/or any other known surgical tool associated with the delivery and attachment of surgical implants. In various aspects, the implant guide 3808 may be used to perform the surgical procedures associated with delivery and placement of the implant outer layer 104 and implant body 102 within the bore, and the attachment of the implant outer layer 104 and/or implant body 102 to the fastener 106 during the formation of the implant assembly 200 while maintaining a precise alignment of the fastener 106 relative to the implant outer layer 104 and implant body 102.

Figure 62:
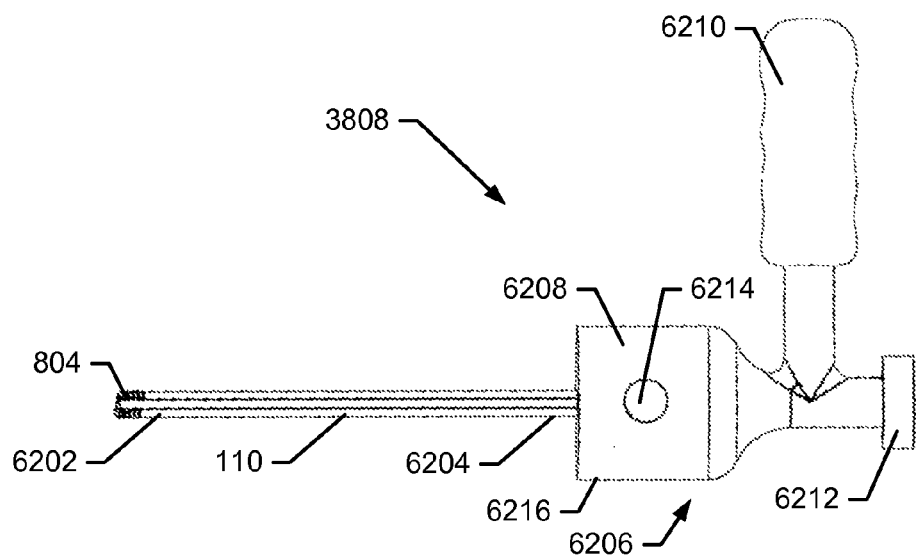
FIG. 62 is a side view of an implant guide.

By way of example, FIG. 62 is a top view of the implant guide 3808 illustrated in FIG. 38. In this aspect, the implant guide 3808 includes a retaining rod 110 with a distal rod end 6202 and a proximal rod end 6204 attached to a robust implant guide handle 6206. In this aspect, the implant guide handle 6206 includes a handle body 6208, a grip 6210 projecting essentially perpendicularly from the handle body 6208, and a proximal access port 6212. The handle body 6208 may contain various internal locking elements (not shown) within a handle body housing 6216 to provide a reversible locked mechanical engagement of the proximal rod end 6204 within the handle body 6208. In this aspect, this reversible locked mechanical engagement may be unlocked by depressing a button 6214 and sliding the proximal rod end 6204 out of the handle body 6208.

Figure 63:
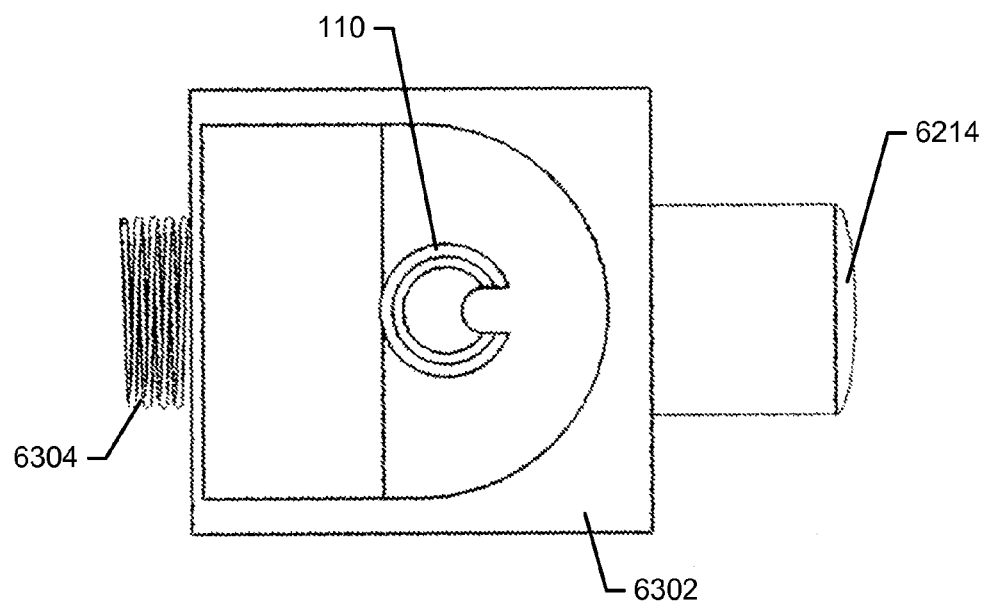
FIG. 63 is a detailed proximal side view of an implant guide with handle body housing, grip, and proximal access port removed.

FIG. 63 is a proximal side view of the implant guide 3808 in which the handle body housing 6216, grip 6210, and proximal access port 6212 are removed to expose the internal locking elements. In this aspect, the internal locking elements may include a sliding block 6302 attached to the button 6214 at one end and operably attached to a bias spring 6304 which biases the position of the sliding block 6302 in the direction of the button 6214, causing the button 6214 to protrude from the handle body housing 6216 as illustrated in FIG. 62.

Figure 64:
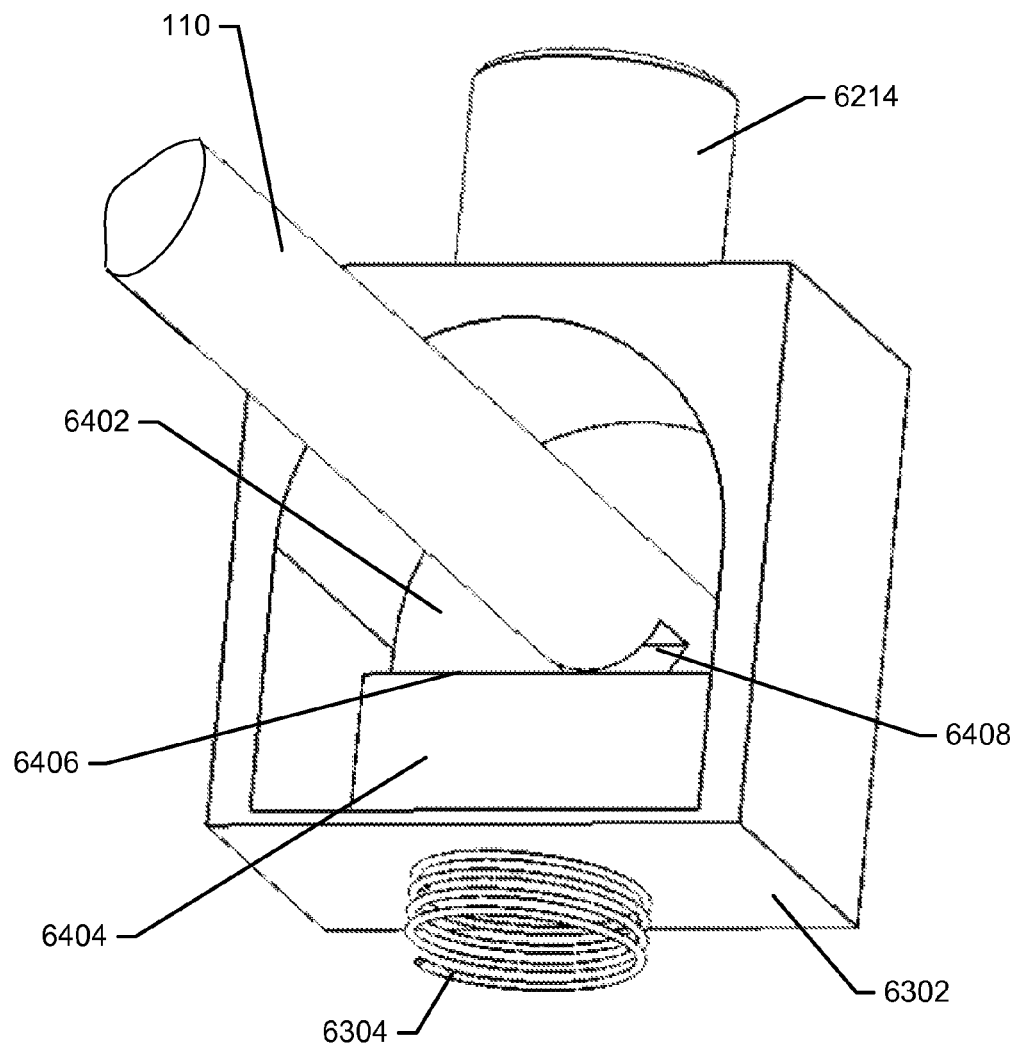
FIG. 64 is a detailed proximal perspective view of an implant guide with handle body housing, grip, and proximal access port removed.

FIG. 64 is a perspective view of the locking elements illustrated in FIG. 63. The sliding block 6302 may enclose an internal volume 6402 containing a blade element 6404 extending the width of the internal volume 6402. When the sliding block 6302 is biased toward the button 6214 by the force generated by the bias spring 6304, the blade edge 6406 is pressed into a notch 6408 formed into the material of the retaining rod 110 to form the locked engagement. When the button 6214 is depressed, the sliding block 6302 shifts toward the bias spring 6304, thereby shifting the blade edge 6406 out of the notch 6408, allowing the removal of the retaining rod 110 from the implant guide handle 6206.

In various other aspects, any other known reversible locking mechanism may be used attach the retaining rod 110 within the implant guide handle 6206. Non-limiting examples of suitable locking mechanisms include collars with one or more set screws, pins, pegs, and/or any other insertable elongate element; clamps; bands; compression fittings; and any combination thereof.

Figure 65:
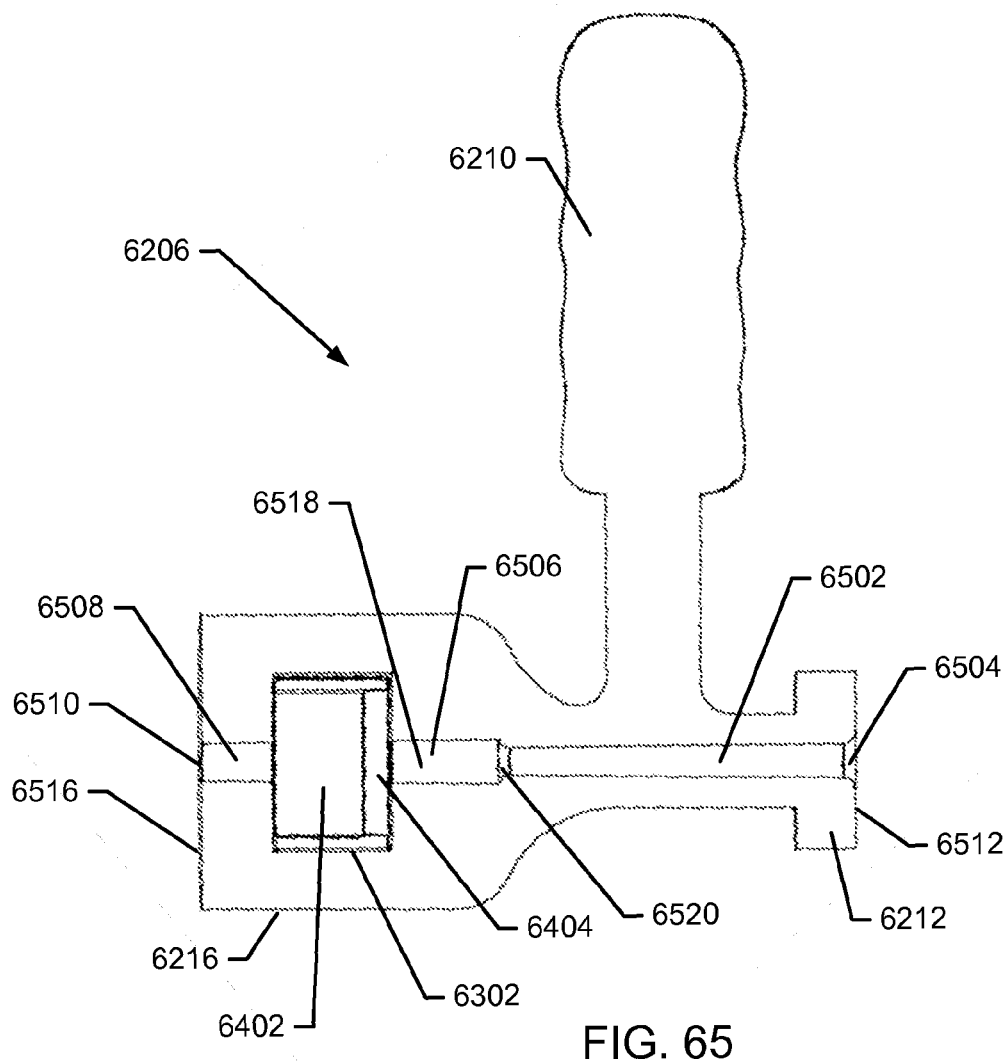
FIG. 65 is a lateral cross-sectional view of the implant guide handle illustrated in FIG. 62 taken in the drawing plane of FIG. 62.

FIG. 65 is a cross-sectional view of the implant guide handle 6206 illustrated in FIG. 62 taken in the drawing plane. The retaining rod 110 is removed in FIG. 65 to expose the internal cavities of the implant guide handle 6206. The sliding block 6302 and blade element 6404 are contained within the handle body housing 6216 as described herein previously. In addition, the handle body housing 6216 contains a channel 6518 that extends the entire length of the implant guide handle 6206, opening at a proximal opening 6504 in the proximal handle face 6512 as well as at a distal opening 6510 in the distal handle face 6516. The channel 6518 may include one or more sections including, but not limited to: a distal channel segment 6508 situated between the distal face 6518 and the internal volume 6402 enclosed by the sliding block 6302; a central channel segment 6506 situated between the internal volume 6402 and a proximal channel segment 6502; and the proximal channel element 6502 ending at the proximal opening 6504. In this aspect, the distal channel segment 6508 and the central channel segment 6506 may have a cross-sectional profile that is matched to the exterior cross-sectional profile of the retaining rod 110 such that the retaining rod fits closely within the channel segments 6506 and 6508. The proximal channel segment may have a cross-sectional profile that is smaller than the corresponding exterior cross-sectional profile of the retaining rod 110; the proximal end of the central channel segment 6506 may end in a contraction 6520 that limits the insertion distance of the retaining rod 110.

Referring back to FIG. 62, the distal rod end 6202 of the retaining rod 110 may terminate in a retaining rod distal end 804 designed to operatively connect to various tool fittings (not shown) associated with the implant body 102 and/or implant outer layer 104 in a reversible locked engagement. Various aspects of the retaining rod distal end 804 were described herein previously in association with FIGS. 8-11 and FIGS. 20-21. For example, the retaining rod distal end 804 may be provided as a threaded tip that may be advanced into corresponding threaded receptacles formed within the implant body 102 and/or the implant outer layer 106 (not shown). Any other suitable reversible locking mechanism may be incorporated into the retaining rod distal end 804 without limitation.

Figure 66:
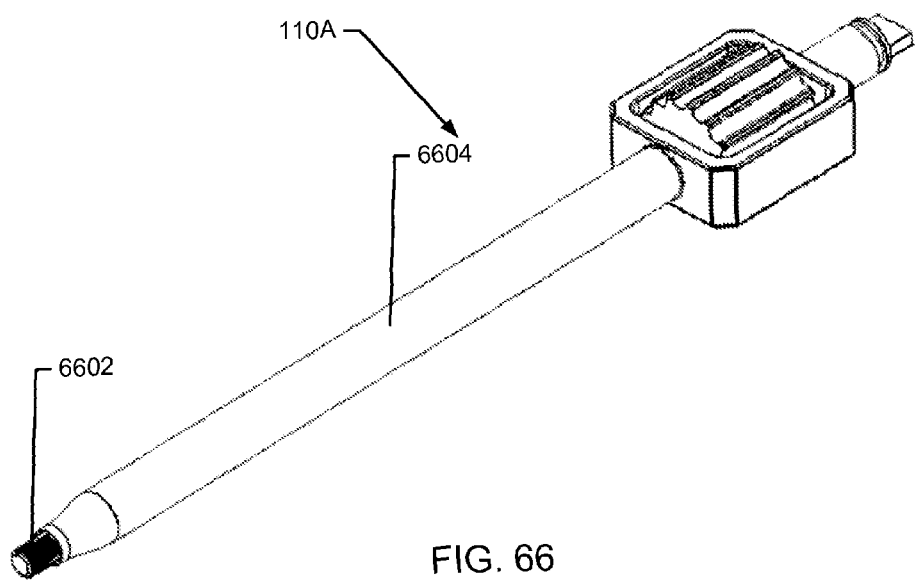
FIG. 66 is a distal perspective view of a dual-element retaining rod.
Figure 67:
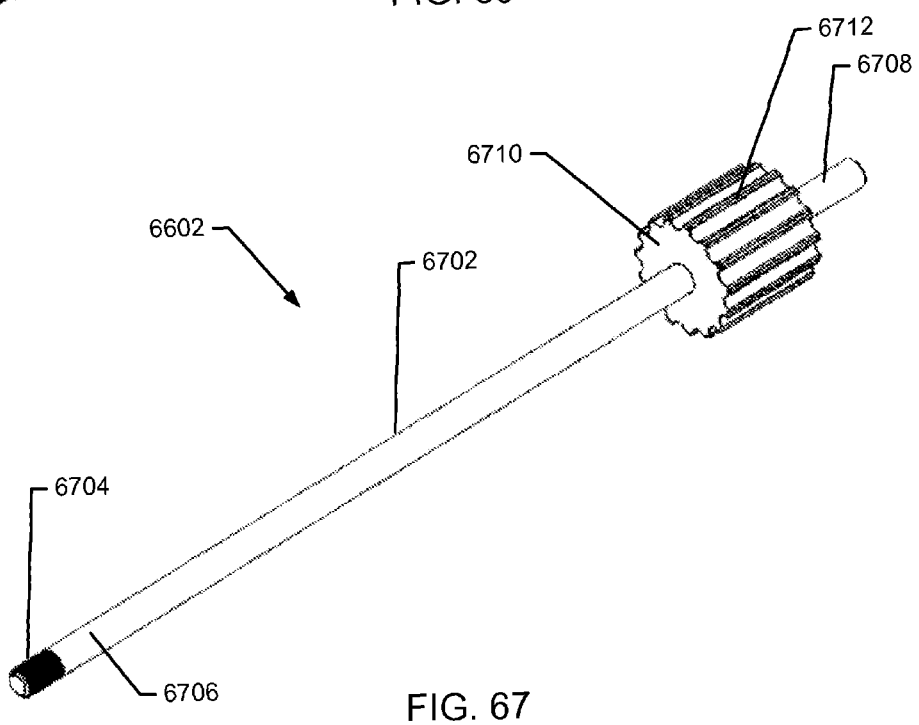
FIG. 67 is a distal perspective view of a central shaft of a dual-element retaining rod.
Figure 68:
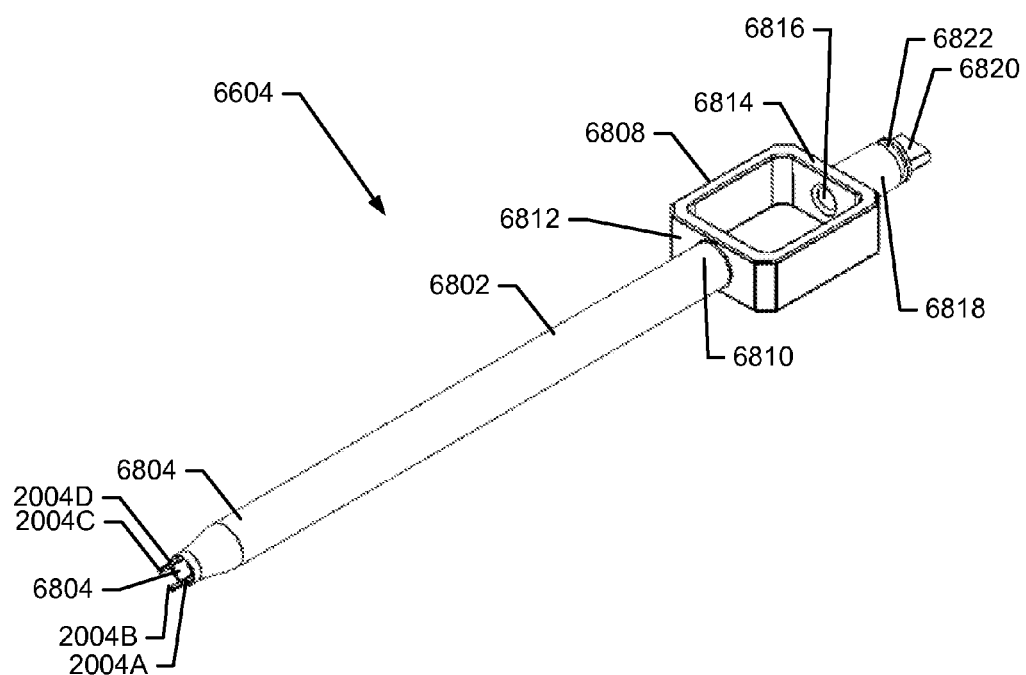
FIG. 68 is a distal perspective view of an outer sleeve of a dual-element retaining rod.

FIG. 66 is a perspective view of a dual-element retaining rod 110A in another aspect. In this aspect, the dual-element retaining rod 110A includes a central shaft 6602 nested within an outer sleeve 6604. A perspective view of the central shaft 6602 only is illustrated in FIG. 67, and a perspective view of the outer sleeve 6604 only is illustrated in FIG. 68 expose the features of the individual elements. Referring to FIGS. 66-68, the central shaft 6602 may include an elongate rod 6702 with a threaded tip 6704 situated at the distal rod end 6706. A proximal end 6708 may be extend through a channel formed within a cylindrical knob 6710 attached using a set screw, pin, or any other known method of fixing a cylindrical knob to a shaft. The cylindrical knob may be provided with a surface texture such as raised ridges 6712 as illustrated in FIGS. 66-67, or other surface textures such as knurling to facilitate the twisting of the central shaft 6602 within the outer sleeve 6604.

The outer sleeve 6604 includes a hollow cylindrical tube 6802 at with tines 2004A-2004D (see FIG. 20) projecting distally from the distal tube end 6804. The tines 2004A-2004D may interlock with corresponding indentations in the implant outer layer 104 as illustrated in FIGS. 20-21.

Referring back to FIGS. 66-68, the hollow cylindrical tube 6802 encloses a central channel (not shown) that opens at the distal end in a distal opening 6806. The threaded tip 6704 of the central shaft 6602 protrudes distally from this distal opening 6806.

The outer sleeve 6604 also includes a frame 6808 attached at one end to a proximal end 6810 of the hollow cylindrical tube 6802. The distal edge 6812 of the frame 6808 contains an opening aligned with the central channel of the hollow cylindrical tube 6802 to allow the insertion of the proximal end 6708 of the central shaft 6602. The proximal edge 6814 of the frame 6808 contains a blind fitting 6816 to receive the proximal end 6708 of the central shaft 6602. The outer sleeve 6604 further includes a cylindrical proximal handle attachment fitting 6818 attached to the proximal edge 6814 of the frame 6808 opposite to the blind fitting 6816. The handle attachment fitting 6818 may include features for attaching to a handle (not shown) similar to the implant guide handle 6206 described previously herein in connection with FIGS. 62-65. The attachment features may include a blade-like element 6820 protruding proximally from the attachment fitting 6818, a circumferential groove 6822, and any other attachment feature known in the art in any combination.

III. Methods of Treatment Using Orthopedic Anchoring System

In various aspects, the orthopedic anchoring system 100 described herein may be used to implement a variety of orthopedic surgical methods. Non-limiting examples of suitable orthopedic surgical methods include: vertebral reinforcement or immobilization devices; intervertebral joint reinforcement or immobilization devices; internal fixation devices; and any other orthopedic appliances or orthopedic applications known in the art.

Figure 69:
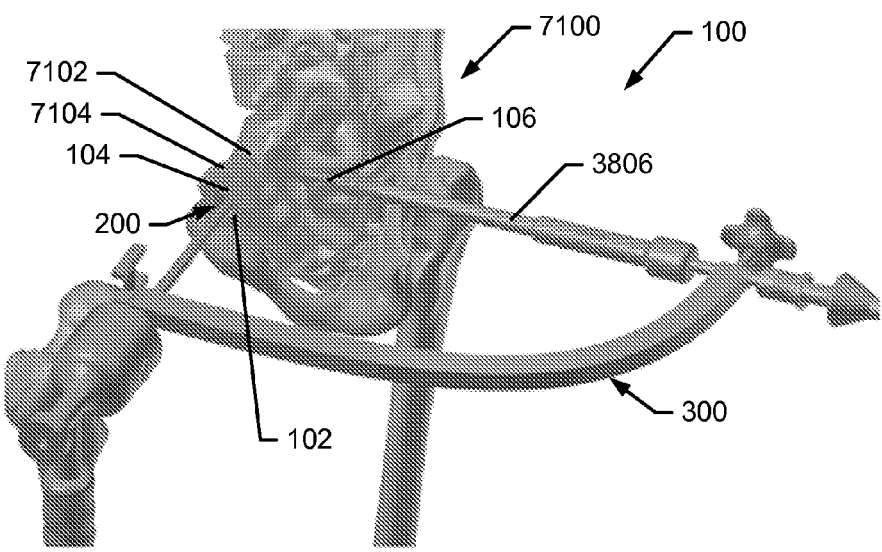
FIG. 69 is an illustration of a simulated orthopedic procedure to stabilize a sacroiliac joint using an orthopedic anchoring system, viewed from a craniolateral and posterior vantage.

FIG. 69 is an illustration of a simulated orthopedic procedure to stabilize a sacroiliac joint using the orthopedic anchoring system 100 in an aspect. In this aspect, the delivery tool 300 is used to situate an implant outer layer 104 within a bore formed within the sacrum 6902 and ileum 6904 of a patient. A fastener 106 is then introduced through the ileum 6904 at a predetermined penetration distance and orientation by the fastener guide 3806. The implant body 102 is then inserted through the outer layer 104 to lock the fastener 106 in place to produce the implant assembly 200. The implant assembly 200 was described previously herein and was illustrated in FIG. 34.

Figure 70:
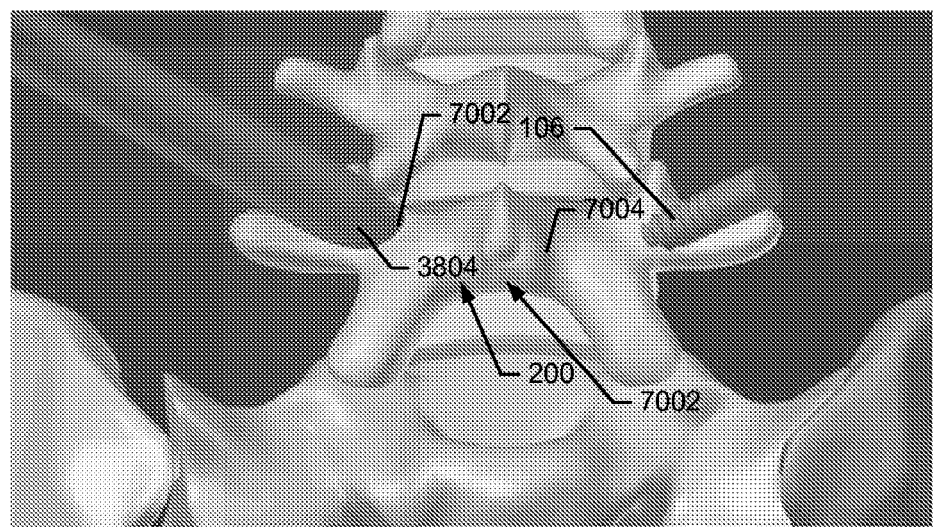
FIG. 70 is an illustration of a simulated orthopedic procedure to provide an anchor for an orthopedic appliance using an orthopedic anchoring system viewed from a posteriocaudal vantage.

FIG. 70 is an illustration of a simulated orthopedic procedure to provide an anchor for an orthopedic appliance using the orthopedic anchoring system 100. The implant assembly 200 was described herein previously and illustrated in FIGS. 22-24 and FIGS. 36-37. In this aspect, the implant outer layer (not visible) is inserted into a bore 7004 formed within a vertebral arch 7002 using the implant guide 3808. A fastener 106 is then introduced through the vertebral arch 7002 at a predetermined penetration distance and orientation by the fastener guide 3806 (not shown). The implant body 102 (not visible) is then inserted through the outer layer 104 followed by a threaded plug 2302 (not visible) using the implant guide 3808 to lock the fastener 106 in place to produce the implant assembly 200.

Figure 71:
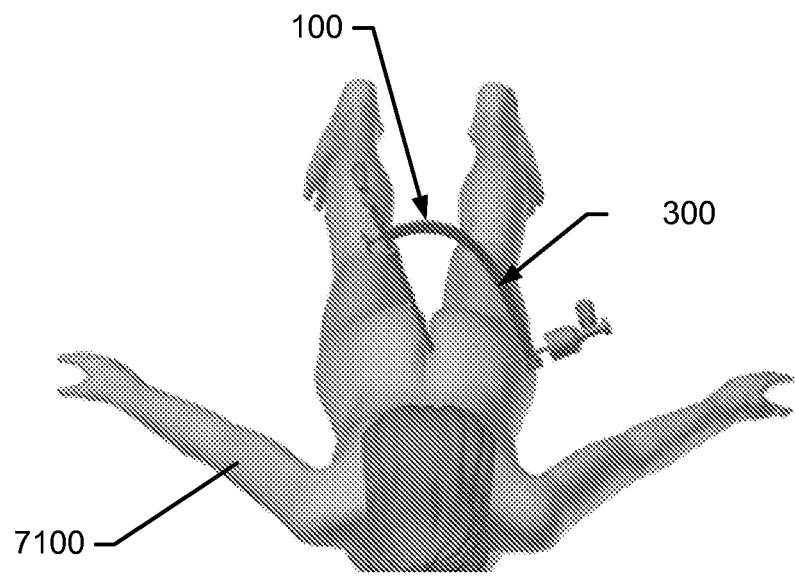
FIG. 71 is an illustration of an orthopedic anchoring system situated on a patient, viewed from a cranioposterior vantage.
Figure 72:
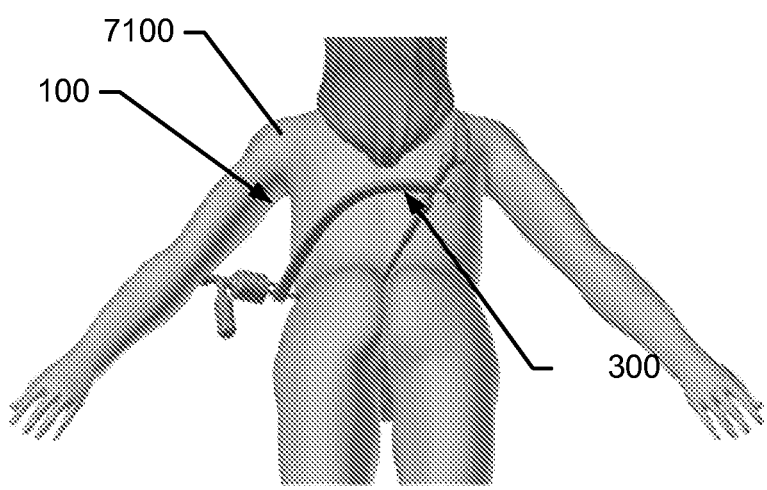
FIG. 72 is an illustration of an orthopedic anchoring system situated on a patient, viewed from a posteriocaudal vantage.

FIGS. 71 and 72 are posteriocaudal and posteriocranial perspective views illustrating the orthopedic anchoring system 100 situated on a patient 7100 as part of the procedure used to produce the implant assembly 200 in an afflicted area. In various aspects, the implant outer layer 104 is situated into position on the patient 7100 for the desired procedure. The positioning of the delivery tool 300 may be confirmed using any suitable medical imaging method including, but not limited to fluoroscopy, CT scanning, X-ray imaging, and any other suitable medical imaging method. In various aspects, the delivery tool 300 may be adjusted to compensate for variations in the morphology of individual patients, using any of the targeting arm adjustment means described herein previously.

Figure 73:
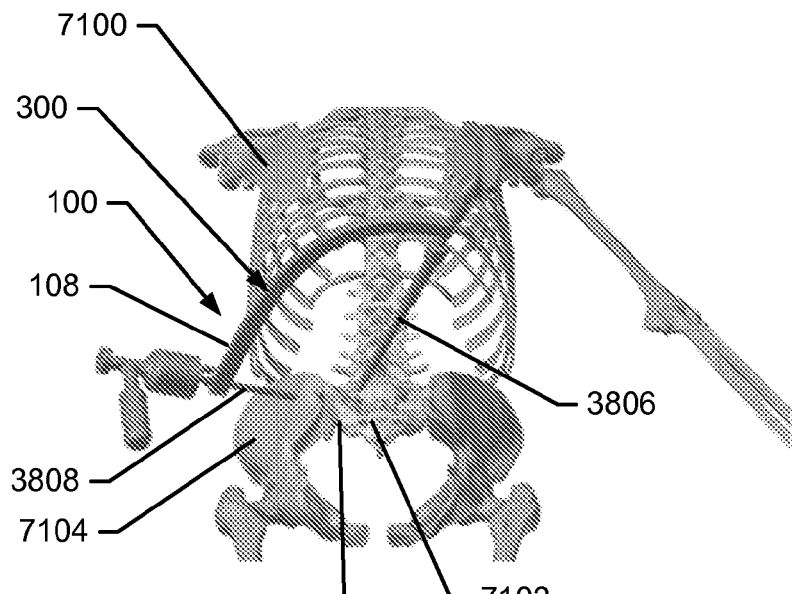
FIG. 73 is an illustration of an orthopedic anchoring system situated on a patient, viewed from a posteriocaudal vantage, with all soft tissues removed.
Figure 74:
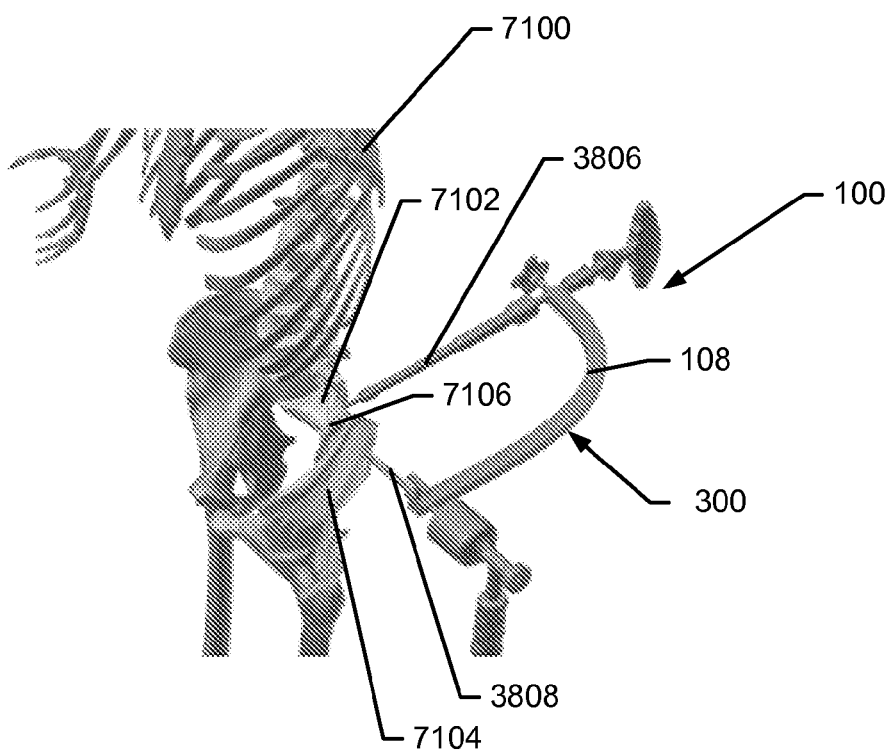
FIG. 74 is an illustration of an orthopedic anchoring system situated on a patient, viewed from an anteriolateral/cranial vantage, with all soft tissues removed.

FIGS. 73 and 74 are posteriocranial and anteriolateral perspective views illustrating the orthopedic anchoring system 100 situated on a patient 7100 for which the soft tissue has been removed to reveal the positions and orientations at which the fastener guide 3806 and the implant guide 3808 enter the sacrum 7102 and ileum 7104, respectively during a procedure to stabilize the sacroiliac joint 7106 of the patient 7100 in one aspect of the method. Once in position, the delivery tool 300 maintains the fastener guide 3806 and the implant guide 3808 in a fixed geometric arrangement relative to one another, ensuring precise alignment of the fastener 106, the implant outer layer 104, and the implant body 102 during the surgical procedure. In addition, the cutting paths of various surgical tools used to prepare the bore to receive the implant outer layer and the hole to receive the fastener 106 are maintained in appropriate alignment with the eventual insertion paths of the components of the implant assembly 200 using the delivery tool 300.

FIG. 69 is an illustration of a simulated orthopedic procedure to stabilize an sacroiliac joint of a patient 7100 using the orthopedic anchoring system 100 in one aspect. The ileum 7104 has been partially removed in FIG. 69 to facilitate visualization of the arrangement of the elements of the orthopedic anchoring system 100. In this aspect, the delivery tool 300 may be used to situate an implant outer layer 104 within a bore formed within the sacrum 7102 and ileum 7104 of a patient 7100 using the implant guide 3808. A fastener 106 is then introduced through the ileum 7104 at a predetermined penetration distance and orientation by the fastener guide 3806. The implant body 102 may then be inserted through the outer layer 104 to lock the fastener 106 in place to produce the implant assembly 200. The implant assembly 200 was described previously herein previously and was illustrated in FIG. 34.

Figure 75:
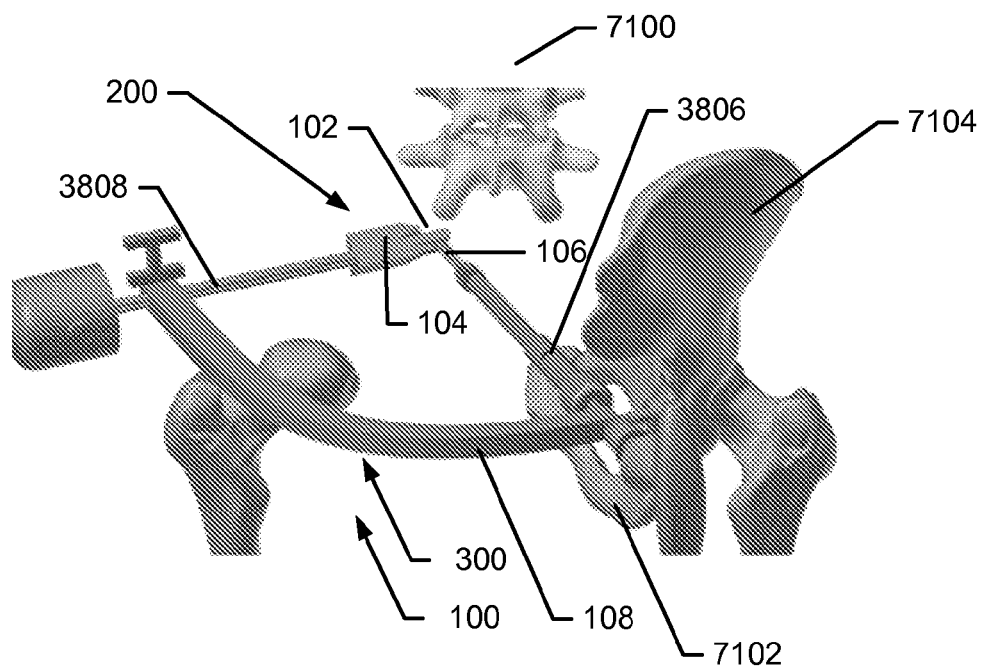
FIG. 75 is an illustration of an orthopedic anchoring system situated on a patient, viewed from a posteriolateral/cranial vantage, with all soft tissues and the patient's left ilium removed.
Figure 76:
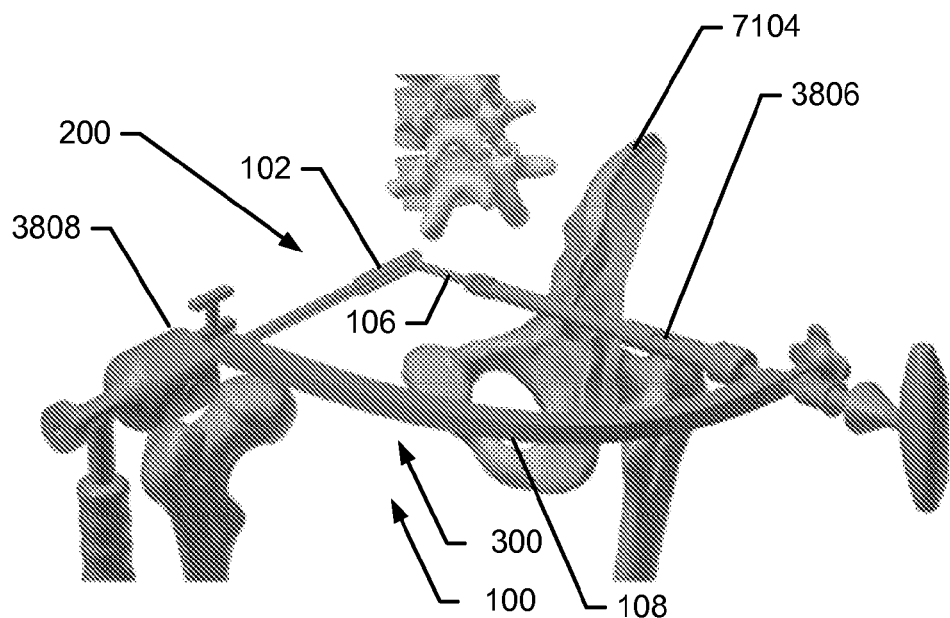
FIG. 76 is an illustration of an orthopedic anchoring system situated on a patient, viewed from a posteriolateral/cranial vantage, with all soft tissues and the patient's left ilium, sacrum, and L5 vertebra removed, and the implant outer layer of an implant assembly removed.
Figure 77:
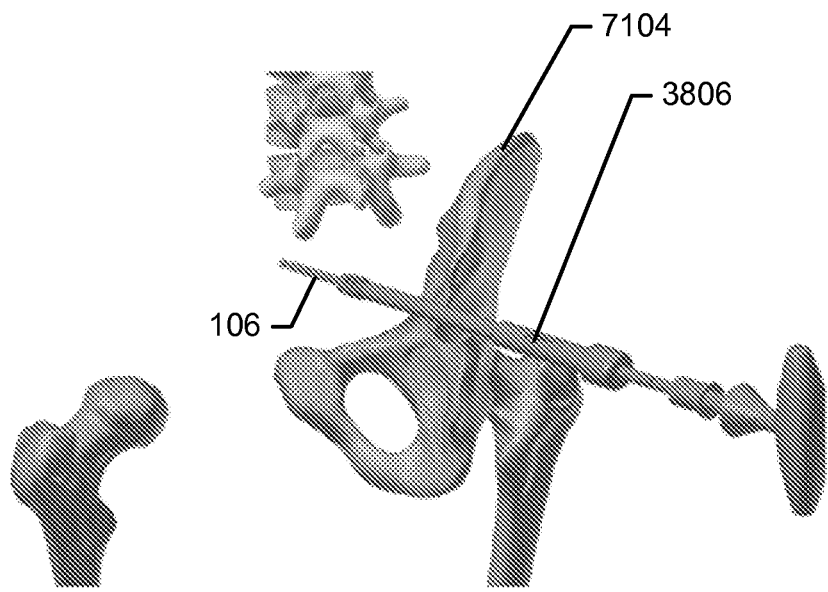
FIG. 77 is an illustration of an orthopedic anchoring system situated on a patient, viewed from a posteriolateral/cranial vantage, with all soft tissues and the patient's left ilium, sacrum, and L5 vertebra removed, as well as the targeting arm, implant guide arm, implant body and implant outer layer removed.

FIGS. 75-80 are additional illustrations of the simulated orthopedic procedure to stabilize an sacroiliac joint using the orthopedic anchoring system 100 in the preceding aspect; all figures are posterior perspective views. FIG. 75 is a view of the procedure with both the sacrum 7102 and the afflicted ileum 7104 of the patient 7100 removed to enhance the visualization of the spatial arrangement of the implant body 102, the implant outer layer 104, and the fastener 106 of the implant assembly 200. FIG. 76 is a similar view to FIG. 75, with the implant outer layer 104 removed to illustrate the mechanical link between the fastener 106 and the implant body 102, and the significance of the alignment of these elements made possible by the fastener guide 3806 and the implant guide 3808 of the delivery device 300. FIG. 77 is a similar view to FIG. 76, with the implant guide 3808 and targeting arm 108 of the delivery device 300 removed to show the fastener guide 3806 and attached fastener 106.

Figure 78:
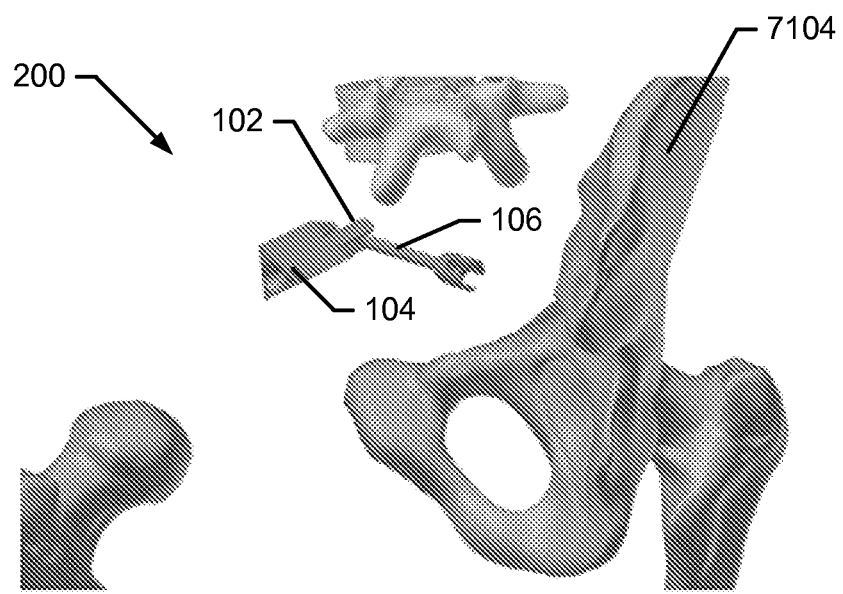
FIG. 78 is an illustration of an implant assembly situated on a patient, viewed from a posteriolateral/cranial vantage, with all soft tissues and the patient's left ilium, sacrum, and L5 vertebra removed.
Figure 79:
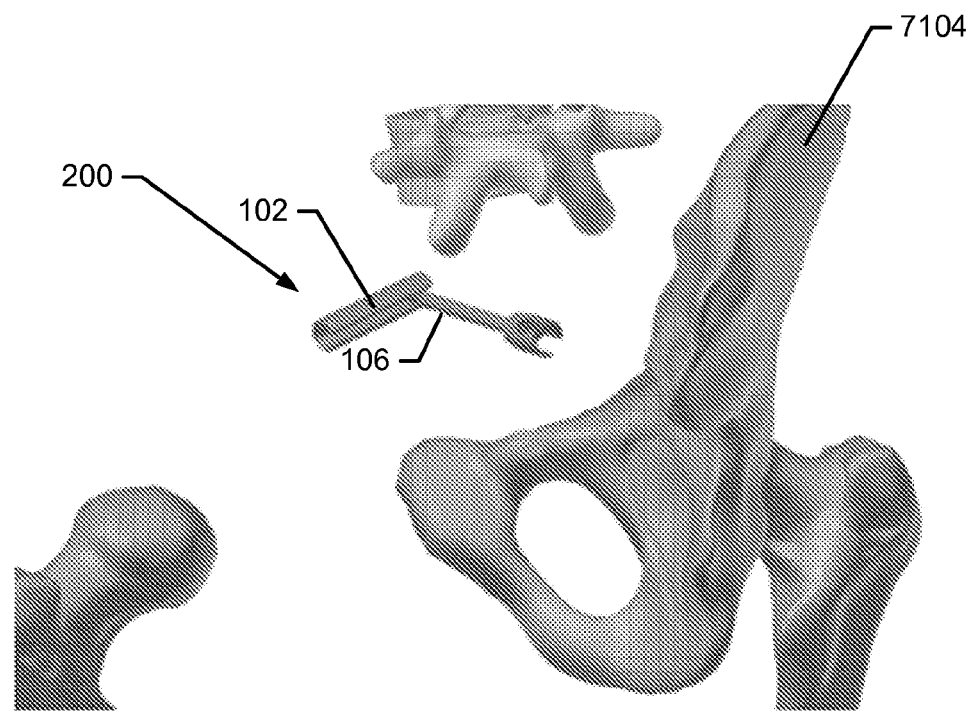
FIG. 79 is an illustration of an implant assembly with the implant outer layer removed situated on a patient, viewed from a posteriolateral/cranial vantage, with all soft tissues and the patient's left ilium, sacrum, and L5 vertebra removed.
Figure 80:
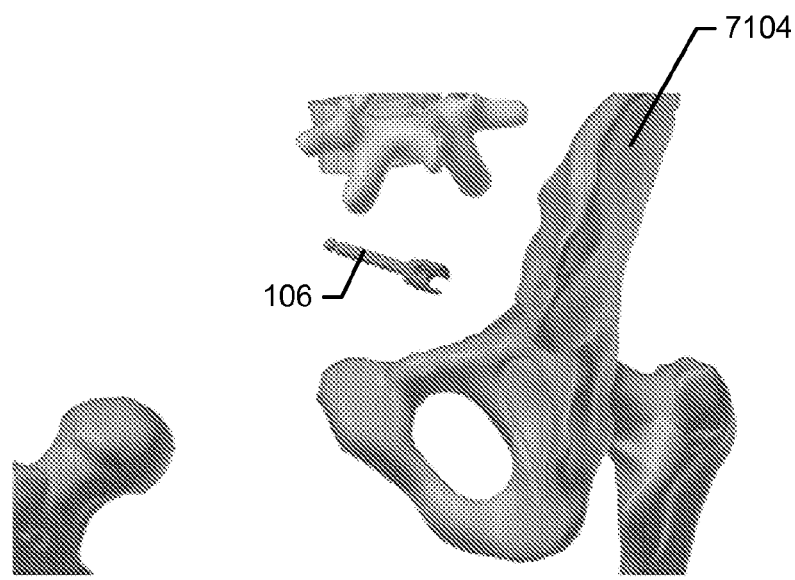
FIG. 80 is an illustration of a fastener of an implant situated on a patient, viewed from a posteriolateral/cranial vantage, with all soft tissues and the patient's left ilium, sacrum, and L5 vertebra removed.

FIG. 78 is a similar view to previous FIGS. 75-77, but with the delivery device 300 removed to reveal the spatial arrangement of the implant body 102, the implant outer layer 104, and the fastener 106 of the implant assembly 200. The implant outer layer 104 is additionally removed in FIG. 79 to reveal the spatial arrangement of the implant body 102 and attached fastener 106 of the implant assembly 200. FIG. 80 additionally removes the implant body 102, the implant outer layer 104, and the fastener 106 of the implant assembly 200 to reveal the alignment of the fastener 106 in this simulated orthopedic procedure.

In addition to stabilization of a sacroiliac joint or intravertebral joints, the implant assembly 200 may be used as a robust anchor to provide support for other orthopedic stabilization appliances. FIG. 70 is an illustration of a simulated orthopedic procedure to provide an anchor for an orthopedic appliance using the orthopedic anchoring system 100 in another aspect. The implant assembly 200 was described herein previously and illustrated in FIGS. 22-24 and FIGS. 36-37. In this aspect, the implant outer layer (not visible) is inserted into a bore 7004 formed within a vertebral arch 7002 using the implant guide 3808; in this aspect the vertebral arch 7002 is a part of the $5^{th}$ lumbar vertebra 7006. A fastener 106 may then be introduced through the vertebral arch 7002 at a predetermined penetration distance and orientation by the fastener guide 3806 (not shown). The implant body 102 (not visible) is then inserted through the outer layer 104 followed by a threaded plug 2302 (not visible) using the implant guide 3808 to lock the fastener 106 in place to produce the implant assembly 200.

In the various aspects of the methods described previously herein, the fastener 106, the implant outer layer 104 and implant body 102 may be implanted in any possible sequence without limitation. The particular sequence of elements implanted in any aspect of the method may be influenced by one or more factors including, but not limited to: the particular orthopedic surgical procedure to be performed, the location and condition of the tissues in the afflicted area, and the particular design of the elements of the implant assembly 200 as described previously herein.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An orthopedic anchoring system comprising:
   an implant assembly comprising:
   an implant body comprising at least a portion of a locking element comprising a slot having lateral sides formed in the implant body;
   an implant outer layer comprising a longitudinal axis and a lumen extending parallel to the longitudinal axis, wherein the lumen is configured to receive at least a portion of the implant body within the lumen; and
   a fastener comprising an attachment feature configured to mechanically interlock with the locking element in a force-fit mechanical engagement, the attachment feature comprising a fastener distal end attached to the fastener by a contracted neck region, wherein the fastener distal end is configured to be forced through the slot to produce the force-fit mechanical engagement between the lateral sides of the slot and the fastener distal end;

a delivery tool comprising:
  an implant guide configured to releasably couple to at least one of the implant body or the implant outer layer; and
  a fastener guide operably coupled to the implant guide and configured to deliver the attachment feature of the fastener to the locking element;
wherein a final manufactured configuration of the delivery tool and a final manufactured configuration of the implant assembly are such that, when the system is assembled such that the implant guide is releasably coupled to at least one of the implant body or the implant outer layer, a delivery arrangement automatically exists such that the fastener guide is correctly oriented to deliver the attachment feature to the locking element.

2. The system of claim 1, wherein in being coupled together, the implant guide and fastener guide form an angle relative to each other, and the angle is non-adjustable.

3. The system of claim 1, wherein the locking element is situated near a distal end of the implant body.

4. The system of claim 3, wherein the implant outer layer further comprises a fastener opening configured to provide a path through which the attachment feature passes to engage the locking element in a force-fit mechanical engagement.

5. The system of claim 1, wherein the implant outer layer further comprises a first alignment feature and the implant body further comprises an second alignment feature, wherein the first alignment feature is configured to operatively connect to the second alignment feature, resulting in a predetermined angular alignment of the implant body within the lumen about a rotational axis aligned parallel to the longitudinal axis and situated along a centerline of the implant body.

6. The system of claim 5, wherein:
  the first alignment feature comprises a first non-circular cross-sectional profile,
  the second alignment feature comprises a second non-circular cross-sectional profile corresponding to the first non-circular cross-sectional profile, and
  the first non-circular cross-sectional profile and the second non-circular cross-sectional profile are aligned only at the predetermined angular alignment.

7. The system of claim 5, wherein:
  the first alignment feature is chosen from a longitudinal ridge or groove formed on an outer surface of the implant body and aligned with the longitudinal axis;
  the second alignment feature is chosen from corresponding longitudinal groove or ridge formed on an inner surface defining the lumen of the implant outer layer and aligned with the longitudinal axis; and
  the longitudinal ridge or groove meshes with the corresponding longitudinal groove or ridge as the implant body is advanced distally into the lumen only at the predetermined angular alignment.

8. The system of claim 1, wherein the delivery tool further comprises a targeting arm comprising a first arm end and an opposite second arm end, wherein the first arm end is configured to releasably attach the fastener guide and the second arm end is configured to releasably attach the implant guide to operatively couple the fastener guide and the implant guide.

9. The system of claim 8, wherein the targeting arm comprises a fixed structural element configured to operatively couple the fastener guide and the implant guide at a non-adjustable angle relative to each other.

10. The system of claim 1, wherein a pair of longitudinal projections comprises the lateral sides and forms the slot between the pair of longitudinal projections, wherein the fastener distal end is configured to be forced through the slot to produce the force-fit mechanical engagement between the pair of longitudinal projections and the fastener distal end.

11. The system of claim 1, wherein the fastener distal end comprises a ball end.

12. The system of claim 1, wherein the fastener distal end comprises a rounded end.

13. The system of claim 1, wherein the fastener distal end comprises a cone end.

14. An orthopedic anchoring system comprising:
  an implant assembly comprising:
    an implant body comprising at least a portion of a locking element comprising a slot formed within the implant body;
    an implant outer layer comprising a longitudinal axis and a lumen extending parallel to the longitudinal axis, wherein the lumen is configured to receive at least a portion of the implant body within the lumen; and
    a fastener comprising an attachment feature configured to mechanically interlock with the locking element in an interference mechanical engagement, the attachment feature comprises a fastener distal end attached to the fastener by contracted neck region, the locking element extending from a distal end of the implant body in a direction parallel with the longitudinal axis, wherein the slot comprises a slot width between a diameter of the neck region and a diameter of the fastener distal end, the slot is configured to receive the neck region of the attachment feature to retain the fastener distal end and to produce the interference mechanical engagement;
  a delivery tool comprising:
    an implant guide configured to releasably couple to at least one of the implant body or the implant outer layer; and
    a fastener guide operably coupled to the implant guide and configured to deliver the attachment feature of the fastener to the locking element;
  wherein a final manufactured configuration of the delivery tool and a final manufactured configuration of the implant assembly are such that, when the system is assembled such that the implant guide is releasably coupled to the implant body, a delivery arrangement automatically exists such that the fastener guide is correctly oriented to deliver the attachment feature to the locking element.

15. The system of claim 14, wherein the fastener is situated in a final fastener position and the implant body is advanced in a distal direction to form the interference mechanical engagement.

16. The system of claim 15, wherein the implant outer layer further comprises a second locking element comprising a fastener opening configured to receive the attachment feature and to produce the interference mechanical engagement cooperatively with the locking element of the implant body when the implant body is advanced distally within the lumen of the implant outer layer.

17. The system of claim 14, wherein:
  the implant outer layer further comprises a first alignment feature and the implant body further comprises an second alignment feature, wherein the first alignment feature is configured to operatively connect to the second alignment feature, resulting in a predetermined angular alignment of the implant body within the lumen about a rotational axis aligned parallel to the longitudinal axis and situated along a centerline of the implant body, the first alignment feature comprises a first non-circular cross-sectional profile, the second alignment feature comprises a second non-circular cross-sectional profile corresponding to the first non-circular cross-sectional profile, and the first non-circular cross-sectional profile and the second non-circular cross-sectional profile are aligned only at the predetermined angular alignment.

18. The system of claim 14, wherein:

the implant outer layer further comprises a first alignment feature and the implant body further comprises an second alignment feature, wherein the first alignment feature is configured to operatively connect to the second alignment feature, resulting in a predetermined angular alignment of the implant body within the lumen about a rotational axis aligned parallel to the longitudinal axis and situated along a centerline of the implant body, the first alignment feature is chosen from a longitudinal ridge or groove formed on an outer surface of the implant body and aligned with the longitudinal axis;

the second alignment feature is chosen from corresponding longitudinal groove or ridge formed on an inner surface defining the lumen of the implant outer layer and aligned with the longitudinal axis; and the longitudinal ridge or groove meshes with the corresponding longitudinal groove or ridge as the implant body is advanced distally into the lumen only at the predetermined angular alignment.

19. The system of claim 5, wherein the attachment feature is configured to mechanically interlock with the locking element in an interference mechanical engagement, and wherein:

the first alignment feature is chosen from a pin or pin receptacle formed on an outer surface of the implant body;

the second alignment feature is chosen from a corresponding pin receptacle or pin formed on an inner surface defining the lumen of the implant outer layer; and wherein when the implant body is actuated within the lumen the locking element is guided in a predetermined orientation as a result of the first alignment feature being operatively connected to the second alignment feature via a meshing of the pin or pin receptacle with the corresponding pin receptacle or pin.

20. The system of claim 14, wherein:

the implant body further comprises a distal region comprising a body depression contoured to a shape of at least a portion of the attachment feature; and wherein when the body depression is compressed against the attachment feature a meshing engagement therebetween comprises the interference mechanical engagement.

21. The system of claim 20, wherein:

the implant outer layer comprises a contoured surface at a distal end of the lumen shaped to correspond with a shape of at least a portion of the attachment feature to enhance a locked engagement formed between the attachment feature of the fastener and the locking element of the implant body.

22. The system of claim 20, wherein:

at least a portion of the attachment feature comprises a spherical shape and the body depression comprises a contour which is a general surface negative of the spherical shape; and wherein the spherical shape of the at least a portion of the attachment feature is configured and dimensioned to fit closely within the body depression.

23. The system of claim 21, wherein:

at least a portion of the attachment feature comprises a spherical shape and the contoured surface at a distal end of the lumen comprises a contour which is a general surface negative of the spherical shape; and wherein the spherical shape of the at least a portion of the attachment feature is configured and dimensioned to fit closely within the contoured surface at a distal end of the lumen.

24. The system of claim 14, wherein the fastener distal end comprises a ball end.

25. The system of claim 14, wherein the fastener distal end comprises a rounded end.

26. The system of claim 14, wherein the fastener distal end comprises a cone end.

27. An orthopedic anchoring system comprising:

an implant assembly comprising:
an implant body comprising at least a portion of a locking element;
an implant outer layer comprising a longitudinal axis and a lumen extending parallel to the longitudinal axis, wherein the lumen is configured to receive at least a portion of the implant body within the lumen, the implant outer layer further comprises a first alignment feature formed on the inner surface of the lumen, an exterior surface, a fastener opening, a fastener opening perimeter; and
a fastener comprising an attachment feature configured to mechanically interlock with the locking element in an interference mechanical engagement, the attachment feature comprising a distal end attached to the fastener by a contracted neck region;

a delivery tool comprising:
an implant guide configured to releasably couple to at least one of the implant body or the implant outer layer; and
a fastener guide operably coupled to the implant guide and configured to deliver the attachment feature of the fastener to the locking element;

wherein a final manufactured configuration of the delivery tool and a final manufactured configuration of the implant assembly are such that, when the system is assembled such that the implant guide is releasably coupled to at least one of the implant body or the implant outer layer, a delivery arrangement automatically exists such that the fastener guide is correctly oriented to deliver the attachment feature to the locking element, wherein the fastener opening communicates between the exterior surface and the lumen through a lumen wall and is configured to provide a path through which the attachment feature passes to engage the locking element in the interference mechanical engagement;

the implant body further comprises a second alignment feature formed on an exterior surface of the implant body configured to operatively engage with the first alignment feature;

the locking element comprises a slot formed through the implant body at a distal region of the implant body, wherein the slot comprises a first end and a second end opposite the first end, a first slot side and a second slot side opposite the first slot side, each of the first and second slot sides attached to the first end and toward the second slot end, a slot width extending between the first slot side and second slot side near a first slot end and dimensioned to include a width which is between a diameter of the contracted neck region and a diameter of the distal end of the attachment feature of the fastener; and the slot is configured to receive the contracted neck region of the attachment feature to retain the distal end of the attachment feature and to produce the interference mechanical engagement; and wherein, when the implant assembly transitions from a first or open condition to a second or locked condition, the first alignment feature being operatively connected to the second feature results in a predetermined alignment of both the implant body relative to the implant outer layer and the slot relative to a position of the attachment feature when received within the lumen through the fastener opening such that the slot and the attachment feature mechanically interlock once in the second or locked condition, the first or open condition being when the locking element does not engage the attachment feature and the second or locked condition being when the locking element engages the attachment feature.

28. The system of claim 27, wherein:
the fastener further comprises a proximal end, a distal end opposite the proximal end, a threaded shaft extending between the proximal and distal ends, and a head coupled to the proximal end configured to selectively rotate freely relative to the shaft and further configured to couple with an elongate reinforcing element.

29. The system of claim 28, wherein:
the implant outer layer comprising an exterior surface with a transverse cross sectional profile comprising at least three apices.

30. The system of claim 28, wherein:
the first alignment feature comprises a first non-circular cross-sectional profile,
the second alignment feature comprises a second non-circular cross-sectional profile corresponding to the first non-circular cross-sectional profile, and
the first non-circular cross-sectional profile and the second non-circular cross-sectional profile are aligned only at the predetermined alignment.

31. The system of claim 28, wherein:
the first alignment feature is chosen from a longitudinal ridge or groove formed on an outer surface of the implant body and aligned with the longitudinal axis;
the second alignment feature is chosen from corresponding longitudinal groove or ridge formed on an inner surface defining the lumen of the implant outer layer and aligned with the longitudinal axis; and
the longitudinal ridge or groove meshes with the corresponding longitudinal groove or ridge as the implant body is advanced distally into the lumen only at the predetermined alignment.

32. The system of claim 28, wherein:
the first alignment feature is chosen from a pin or pin receptacle formed on an outer surface of the implant body;
the second alignment feature is chosen from corresponding pin receptacle or pin formed on an inner surface defining the lumen of the implant outer layer; and wherein when the implant body is actuated within the lumen the locking element is guided in a predetermined orientation as a result of the first alignment feature being operatively connected to the second alignment feature via a meshing of the pin or pin receptacle with the corresponding pin receptacle or pin.

33. The system of claim 28, wherein:
the implant body further comprises a distal region comprising a body depression contoured to a shape of at least a portion of the attachment feature; and
wherein when the body depression is compressed against the attachment feature a meshing engagement therebetween comprises the interference mechanical engagement.

34. The system of claim 33, wherein:
the implant outer layer comprises a contoured surface at a distal end of the lumen shaped to correspond with the shape of the at least a portion of the attachment feature to enhance a locked engagement formed between the attachment feature of the fastener and the locking element of the implant body.

35. The system of claim 33, wherein:
the at least a portion of the attachment feature comprises a spherical shape and the body depression comprises a contour which is a general surface negative of the spherical shape; and
wherein the spherical shape of the at least a portion of the attachment feature is configured and dimensioned to fit closely within the body depression.

36. The system of claim 34, wherein:
the at least a portion of the attachment feature comprises a spherical shape and the contoured surface at the distal end of the lumen comprises a contour which is a general surface negative of the spherical shape; and
wherein the spherical shape of the at least a portion of the attachment feature is configured and dimensioned to fit closely within the contoured surface at the distal end of the lumen.

37. The system of claim 28, wherein:
the fastener guide is operably coupled to the implant guide via a targeting arm comprising a single continuous structural element having a fixed elongate shape.

38. The system of claim 28, wherein:
the fastener guide is operably coupled to the implant guide via a targeting arm comprising two or more linked structural elements having an adjustable elongate shape.

39. The system of claim 38, wherein:
the targeting arm comprises a telescoping arrangement via the two or more linked structural elements.

40. The system of claim 39, wherein:
the targeting arm comprises a first section ending in a first arm end and a second section ending in a second arm end; both sections having matched circular arc shapes with a common center.

41. The system of claim 40, wherein:
one of the first or second sections comprises a hollow cross-section having a central lumen, and one of the second or first sections is shaped and dimensioned to fit within the central lumen by sliding along an arc length of one of the first or second sections.

42. The system of claim 38, wherein:
the targeting arm further comprises a sliding attachment fitting which permits sliding between the two or more linked structural elements to adjust a relative position thereof.

43. The system of claim 42, wherein:

the targeting arm further comprises a locking mechanism selected from at least one of a set screw, a clamp, a peg, a compression fitting, and any combination thereof and configured such that the elongate shape of the targeting arm and the sliding attachment fitting may be locked into a fixed position when employing the locking mechanism.

44. The system of claim 42, wherein:

the two or more linked structural elements comprises a horizontal segment linked to a vertical segment wherein the arrangement between the horizontal segment and vertical segment result in a sliding in a horizontal direction along the horizontal segment to adjust a relative position of the vertical segment.

45. The system of claim 28, wherein:

the targeting arm comprises two or more hinged or jointed subsections resulting in the delivery arrangement.

46. The system of claim 28, wherein:

the targeting arm comprises one or more bendable subsections having limited deformability resulting in the delivery arrangement.

47. The system of claim 28, wherein:

the fastener guide is operably couple to the implant guide via a targeting arm, the targeting arm attached to the fastener guide at a fastener guide attachment fitting, the fastener guide attachment fitting configured to receive a portion of the fastener guide in a reversibly locked mechanical engagement; wherein when unlocked the fastener guide attachment fitting allows limited movement of the fastener guide including at least one of rotation of the fastener guide about a fastener longitudinal axis and translation of the fastener guide along the fastener longitudinal axis such that even when unlocked the fastener guide attachment fitting is configured to maintain a fixed orientation between the fastener longitudinal axis and the longitudinal axis of the implant outer layer.

48. The system of claim 47, wherein:

the fastener guide attachment fitting comprises a collar having a locking mechanism configured to compresses a fastener guide shaft, thereby locking the fastener guide shaft in a reversibly locked mechanical engagement, the locking mechanism selected from one or more set screws, cotter pins, pegs, clamps, bands, compression fittings, and any combination thereof.

49. The system of claim 28, wherein:

the fastener guide includes a bone screw inserter nested within a sleeve comprising a threaded distal end, a distal end of the bone screw inserter configured to protrude from the threaded distal end of the sleeve, the distal end of the bone screw inserter comprising a screwdriver tip, a screw head fitting positioned proximal the screwdriver tip and wherein the threaded distal end of the sleeve and the screw head fitting of the bone screw inserter are configured to cooperatively reversibly attach to the head of the fastener in a mechanically locked engagement during a formation of the implant assembly and wherein the screwdriver tip is configured to be received within a corresponding screwdriver fitting formed within a portion of the fastener at the proximal end, the screw head fitting configured to be received within an upward-opening groove formed within support elements of the head of the fastener.

50. The system of claim 27, wherein the distal end of the attachment feature comprises a ball end.

51. The system of claim 27, wherein the distal end of the attachment feature comprises a rounded end.

52. The system of claim 27. wherein the distal end of the attachment feature comprises a cone end.

* * * * *

UNITED STATES PATENT AND TRADEMARK OFFICE
CERTIFICATE OF CORRECTION

PATENT NO. : 9,554,909 B2  
APPLICATION NO. : 14/413318  
DATED : January 31, 2017  
INVENTOR(S) : Edward Jeffrey Donner et al.

Page 1 of 1

It is certified that error appears in the above-identified patent and that said Letters Patent is hereby corrected as shown below:

In the Claims

- In Claim 27, Column 47, Line 4, of the issued patent, following the word "end", insert --such that they extend generally parallel to one another away from the first slot end--.

Signed and Sealed this
Thirtieth Day of May, 2017

Michelle K. Lee
*Director of the United States Patent and Trademark Office*